US009183736B2

(12) United States Patent
Sloo et al.

(10) Patent No.: US 9,183,736 B2
(45) Date of Patent: Nov. 10, 2015

(54) SMART-HOME HAZARD DETECTOR PROVIDING SENSOR-BASED DEVICE POSITIONING GUIDANCE

(71) Applicant: Google Inc., Mountain View, CA (US)

(72) Inventors: David Sloo, Menlo Park, CA (US); Kevin Peterson, San Francisco, CA (US); Michael Dixon, Mountain View, CA (US)

(73) Assignee: GOOGLE INC., Mountain View, CA (US)

( * ) Notice: Subject to any disclaimer, the term of this patent is extended or adjusted under 35 U.S.C. 154(b) by 0 days.

(21) Appl. No.: 14/645,216

(22) Filed: Mar. 11, 2015

(65) Prior Publication Data

US 2015/0254970 A1 Sep. 10, 2015

Related U.S. Application Data

(63) Continuation of application No. 14/508,536, filed on Oct. 7, 2014, now Pat. No. 9,019,111.

(60) Provisional application No. 61/887,969, filed on Oct. 7, 2013, provisional application No. 61/887,963, filed on Oct. 7, 2013.

(51) Int. Cl.
*G08B 17/10* (2006.01)
*G08B 29/02* (2006.01)

(52) U.S. Cl.
CPC .................................... *G08B 29/02* (2013.01)

(58) Field of Classification Search
CPC ................................................ G08B 29/02
USPC .................................... 340/628–632; 706/14
See application file for complete search history.

(56) References Cited

U.S. PATENT DOCUMENTS

| | | | | |
|---|---|---|---|---|
| 4,254,414 | A | 3/1981 | Street et al. | |
| 4,313,110 | A | 1/1982 | Subulak et al. | |
| 4,390,869 | A | 6/1983 | Christen et al. | |
| 8,620,841 | B1 * | 12/2013 | Filson et al. | 706/12 |
| 2007/0255522 | A1 | 11/2007 | Gordon et al. | |
| 2010/0052574 | A1 | 3/2010 | Blakeley et al. | |
| 2010/0195810 | A1 | 8/2010 | Mota et al. | |
| 2010/0325074 | A1 | 12/2010 | Ng et al. | |
| 2012/0126975 | A1 | 5/2012 | Gonzales | |
| 2014/0085093 | A1 * | 3/2014 | Mittleman et al. | 340/628 |

FOREIGN PATENT DOCUMENTS

WO 2015/054288 A1 4/2015

OTHER PUBLICATIONS

International Office Action mailed on Dec. 24, 2014 for International Patent Application PCT/US2014/059538 filed on Oct. 7, 2014, all pages.

ISR/WO mailed on Feb. 26, 2015 for International Patent Application PCT/US2014/059538 filed on Oct. 7, 2014, all pages.

* cited by examiner

*Primary Examiner* — Eric M Blount
(74) *Attorney, Agent, or Firm* — Kilpatrick Townsend & Stockton LLP

(57) ABSTRACT

A particular smart hazard detector may itself function as a guide during a process of installation of the same at an installation location. Additionally, the installation location of the particular smart hazard detector may play a central role in how various settings of the smart hazard detector are defined and adjusted over time.

20 Claims, 33 Drawing Sheets

100

Provide input corresponding to a location of installation of a particular hazard detector 102

Implement procedure to advise what features of the hazard detector are recommended based on the location of installation 104

Implement procedure to define alarm conditions of the hazard detector based on the location of installation 106

Implement procedure to guide installation of the hazard detector at the location of installation 108

Implement procedure to modify alarm conditions of the hazard detector based on the location of installation 110

500

508

500

230

500

3100

SMART-HOME HAZARD DETECTOR PROVIDING SENSOR-BASED DEVICE POSITIONING GUIDANCE

CROSS-REFERENCE TO RELATED APPLICATIONS

This application is a continuation of U.S. Nonprovisional application Ser. No. 14/508,536, filed 7 Oct. 2014 and entitled SMART-HOME HAZARD DETECTOR PROVIDING SENSOR-BASED DEVICE POSITIONING GUIDANCE, which claims priority to U.S. Provisional App. Ser. No. 61/887,969, filed 7 Oct. 2013 and entitled USER-FRIENDLY DETECTION UNIT and U.S. Provisional App. Ser. No. 61/887,963, filed 7 Oct. 2013 and entitled HAZARD DETECTION IN A SMART-SENSORED HOME, all of which are hereby incorporated by reference for all intents and purposes.

TECHNICAL FIELD

The present disclosure is directed to or towards systems, devices, methods, and related computer-program products for providing hazard-detection objectives. More particularly, the present disclosure relates to a plurality of devices, including intelligent, multi-sensing, network-connected hazard detection units or smart hazard detectors, such as detectors that incorporate smoke detector features, carbon monoxide detector features and, etc., that communicate with each other and/or with a central server or a cloud-computing system to provide any of a variety of hazard-detection objectives that are useful in smart building and/or smart home environments.

BACKGROUND

Hazard detectors use sensors to detect substances in the air that may be harmful or that may indicate the development of a hazardous situation. For example, carbon monoxide (CO) and radon gas are substances that can be harmful to humans and animals if exposed to high amounts. However, these substances are difficult to detect with the human senses because they are colorless, odorless, and tasteless. A hazard detector can detect the presence of these substances and prevent the harmful effects of exposure by alarming to notify a user. In other instances, a substance such as smoke, while not necessarily harmful in and of itself, can indicate the development of a hazardous situation, such as fire. An early alarm of the presence of such a substance can prevent the hazardous situation from developing or minimize the harmful effects of the situation. Interconnected hazard detectors include detectors that are connected to a network, enabling communication between the detectors or with a central control unit. This provides several advantages over standalone detectors, including the ability to activate multiple alarms when a single detector is triggered. Hazard detectors may be certified under standards defined by governing bodies and/or by companies that perform safety testing, such as Underwriters Laboratories (UL). For example, certain UL standards define thresholds for when smoke detectors and CO detectors should sound an alarm. Certain UL standards also define the required characteristics of the alarm, such as powering requirements and the volume, pitch, and pattern of the alarming sound.

SUMMARY

In general, a particular smart hazard detector may itself function as a guide during a process of installation of the same at an installation location. Additionally, the installation location of the particular smart hazard detector may play a central role in how various settings of the smart hazard detector are defined and adjusted over time.

In an aspect, a method for guiding installation of a hazard detector may include or comprise receiving, by the hazard detector during installation at a particular location within a residence, an input command to test whether an instant placement of the hazard detector would prevent the hazard detector from operating within specification to detect and/or mitigate one or more hazards. The method may include or comprise implementing, by the hazard detector in response to receiving the input command, a test sequence to determine whether the instant placement of the hazard detector would prevent the hazard detector from operating within specification to detect and/or mitigate one or more hazards. The method may include or comprise outputting, by the hazard detector, a particular notification during installation at the particular location when it is determined that the instant placement of the hazard detector would prevent the hazard detector from operating within specification to detect and/or mitigate one or more hazards, based upon readings of at least one component of the hazard detector.

In an aspect, a hazard detector may include or comprise: at least one component to test during installation of the hazard detector at a particular location whether an instant placement of the hazard detector would prevent the hazard detector from operating within specification to detect and/or mitigate one or more hazards; and a processing system, in operative communication with the at least one component, that: determines, based upon readings of the at least one component, whether an instant placement of the hazard detector during installation thereof would prevent the hazard detector from operating within specification to detect and/or mitigate one or more hazards; and when it is determined that the instant placement of the hazard detector would prevent the hazard detector from operating within specification to detect and/or mitigate one or more hazards, causes a notification alert to be output to guide a user during installation of the hazard detector to a suitable installation location for the hazard detector.

In an aspect, a hazard detector may include or comprise: at least one diagnostic component; at least one output device; at least one processor, operatively coupled to the at least one diagnostic component and at least one output device; and a memory operatively coupled with and readable by the at least one processor, and having stored therein processor-readable instructions that, when executed by the at least one processor, cause the at least one processor to: receive, during installation of the hazard detector at a particular location within a residence, an input command to test whether an instant placement of the hazard detector would prevent the hazard detector from operating within specification to detect and/or mitigate one or more hazards; implement a test sequence to determine whether the instant placement of the hazard detector would prevent the hazard detector from operating within specification to detect and/or mitigate one or more hazards; and generate a particular notification, for output by the at least one output device, when it is determined that the instant placement of the hazard detector would prevent the hazard detector from operating within specification to detect and/or mitigate one or more hazards, based upon readings of the at least one diagnostic component.

In an aspect, a hazard detector is presented. The hazard detector may include means for receiving, during installation at a particular location within a residence, an input command to test whether an instant placement of the hazard detector would prevent the hazard detector from operating within specification to detect and/or mitigate one or more hazards. The hazard detector may include means for implementing, in response to receiving the input command, a test sequence to determine whether the instant placement of the hazard detector would prevent the hazard detector from operating within specification to detect and/or mitigate one or more hazards. The hazard detector may include means for outputting a particular notification during installation at the particular location when it is determined that the instant placement of the hazard detector would prevent the hazard detector from operating within specification to detect and/or mitigate one or more hazards, based upon readings of at least one component of the hazard detector.

Other aspects are possible.

DETAILED DESCRIPTION

Aspects of the present disclosure are related to intelligent, multi-sensing, network-connected hazard detection units, or smart hazard detectors, that incorporate smoke detector features, carbon monoxide detector features and, etc., and that communicate with each other and/or with a central server or a cloud-computing system to provide any of a variety of hazard-detection objectives that are useful in smart building and/or smart home environments. More specifically, it is contemplated that a particular smart hazard detector may itself function as a guide during a process of installation of the same at an installation location, and that the installation location of the particular smart hazard detector may play a central role in how various settings of the smart hazard detector are defined and adjusted over time. Although not so limited, an appreciation of the various aspects of the present disclosure may gained in light of the following description in connection with the drawings.

Figure 1:
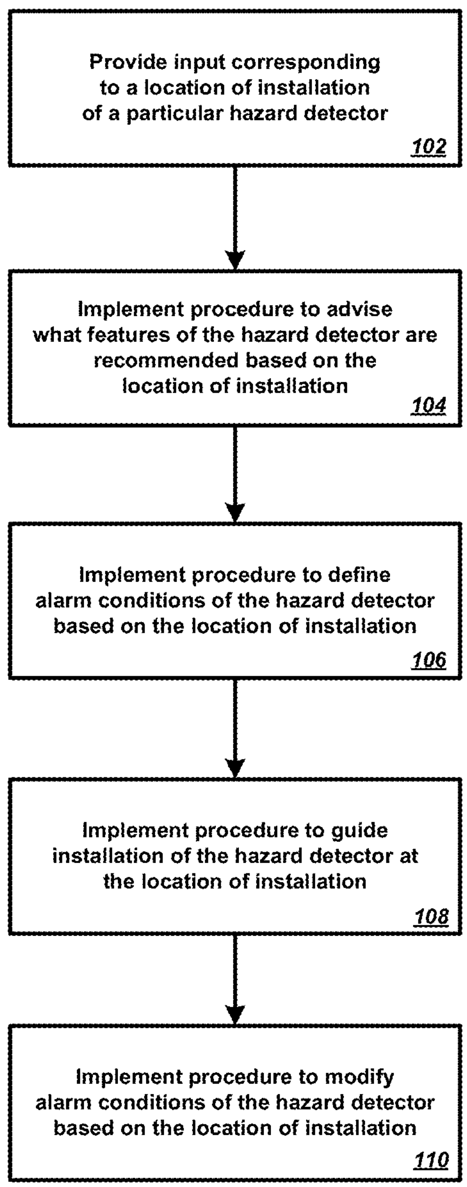
FIG. 1 shows a first example method according to the disclosure.

For instance, referring now to FIG. 1, a first example method 100 is shown in accordance with the principles of the present disclosure. At step 102, an input may be provided or supplied to a particular smart hazard detector, or a device or system communicatively coupled to or with the smart hazard detector for example, that identifies an installation location within a residence of the smart hazard detector. An example of an installation location may include "Hallway" or "Living Room" or "Garage" of or within a particular residence for instance. Other examples are possible, as discussed in further detail below. Further, means for performing step 102 may generally include a smart hazard detector. More specifically, means for performing step 102 may include one or more processing devices, such as processors, and a storage medium, such as to receive and process the input that identifies the installation location within the residence of the smart hazard detector. Other examples are possible.

At step 104, a procedure may be implemented that may serve to advise an installer, for example, what features of the smart hazard detector are recommended to be enabled and/or disabled based upon the installation location of the smart hazard detector. For example, if the installation location is "Garage," it is contemplated that the smart hazard detector, and/or or the device or system communicatively coupled to the smart hazard detector, may via one or both of an audio and a visual cue indicate that "Carbon monoxide detection is not advised. Would you like to disable my carbon monoxide detection capabilities." Other examples are possible, as discussed in further detail below. Further, means for performing step 104 may generally include a smart hazard detector. More specifically, means for performing step 104 may include one or more processing devices, such as processors, and a storage medium, such as to provide a user-perceptible cue (e.g., audio, visual, tactile) as to what features of the smart hazard detector are recommended to be enabled and/or disabled based upon the installation location of the smart hazard detector. Other examples are possible.

At step 106, a procedure may be implemented that may serve to define an alarm condition for each detection-related enabled feature of the smart hazard detector (see step 104), based upon the installation location of the smart hazard detector. For example, if the installation location is "Garage," it is contemplated that the smart hazard detector, and/or or the device or system communicatively coupled to the smart hazard detector, may query a table of predefined threshold settings and access a particular alarm condition setting for carbon monoxide in a garage. The smart hazard detector may then be programmed to exhibit the particular alarm condition setting. An example of a particular alarm condition setting for carbon monoxide in a garage may include "detected carbon monoxide levels greater than or equal to 400 ppm after 5 minutes of monitoring." Other examples are possible, as discussed in further detail below. Further, means for performing step 106 may generally include a smart hazard detector. More specifically, means for performing step 106 may include one or more processing devices, such as processors, and a storage medium, such as to enable the smart hazard detector to be programmed to exhibit the particular alarm condition setting. Other examples are possible.

Next, at step 108, a procedure may be implemented to guide an installer, for example, to install the smart hazard detector at the installation location in manner so that the smart hazard detector may function according to its intended purpose. For example, a particular button integral to the smart hazard detector may be "pressed" to instantiate a test sequence in which the smart hazard detector transmits a signal via ultrasonic transducer to determine if the smart hazard detector is positioned too close to a wall. An example scenario in which the smart hazard detector may determine that the same is too close to a wall may be when the smart hazard detector determines that the wall is less than or equal to 12 inches away. Other examples are possible, as discussed in further detail below. Further, means for performing step 108 may generally include a smart hazard detector. More specifically, means for performing step 108 may include one or more processing devices, such as processors, and a storage medium, such as to provide a user-perceptible cue (e.g., audio, visual, tactile) as a guide to install the smart hazard detector. Other examples are possible.

At step 110, a procedure may be implemented to adjust an existing alarm condition setting for each detection-related enabled feature of the smart hazard detector (see step 106), based upon the installation location of the smart hazard detector. For example, a historical log of data as acquired by a particular sensor of the smart hazard detector may be leveraged as part of an algorithm to enable the smart hazard detector to self-adjust its own (pre)alarm condition settings. For instance, after a particular period of time of 1 month for example, a smart hazard detector installed to "Garage" may adjust an existing pre-alarm condition setting of "detected carbon monoxide levels greater than or equal to 400 ppm after 5 minutes of monitoring" to "detected carbon monoxide levels greater than or equal to 400 ppm after 10 minutes of monitoring," based upon an analysis of a historical log of data that indicates frequent false carbon monoxide alarms in the garage. Other examples are possible, as discussed in further detail below. Further, means for performing step 110 may generally include a smart hazard detector. More specifically, means for performing step 110 may include one or more processing devices, such as processors, and a storage medium, such as to enable the hazard detector to adjust an existing alarm condition setting for each detection-related enabled feature of the smart hazard detector. Other examples are possible.

FIG. 1 illustrates an example implementation of a particular smart hazard detector that may itself function as a guide during a process of installation of the same at an installation location, and that the installation location of the particular smart hazard detector may play a central role in how various settings of the smart hazard detector are defined and adjusted over time. While discussed in the context of pre-installation and post-installation of the smart hazard detector, one or more of the steps of the method 100 may be performed or implemented at a time corresponding to one or both of pre-installation and post-installation of the smart hazard detector. Further, none of the steps of the method 100 need necessarily be performed or implemented, and/or performed or implemented in the particular order as shown and described in connection with FIG. 1.

Figure 2:
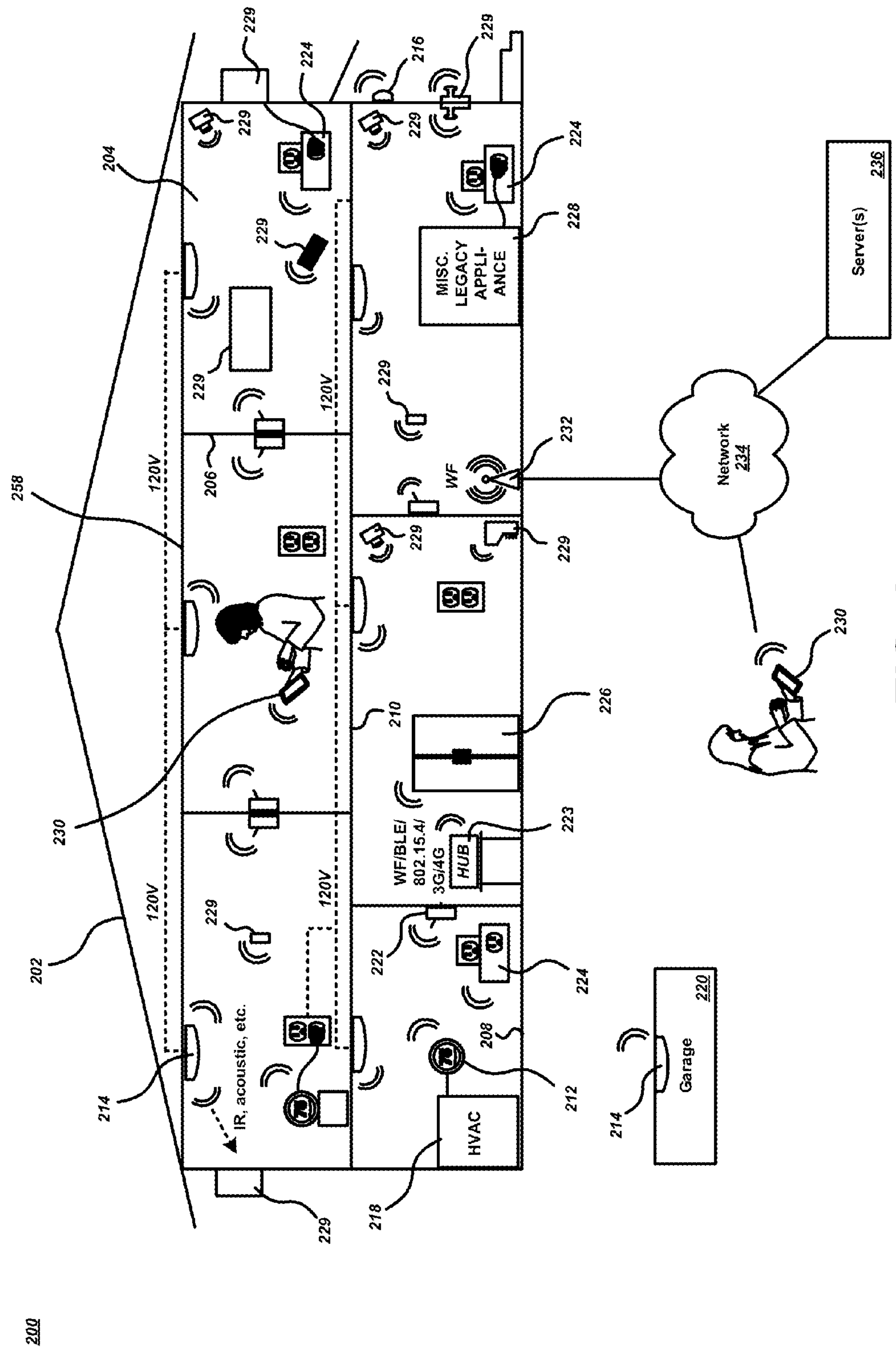
FIG. 2 shows an example smart home environment according to the disclosure.

FIG. 2 illustrates an example smart home environment 200 according to the present disclosure. The example environment 200 includes a structure 202 that has a number of rooms 204 separated at least partly from each other by walls 206 that may include or comprise of interior walls or exterior walls. Each of the rooms 204 may include a floor 208 and a ceiling 210. Various smart devices configured and/or arranged in accordance with the present disclosure may be mounted to, integrated with, and/or supported by any particular feature of the structure 202, such as a particular wall 206, floor 208, ceiling 210, and etc.

In particular, as shown, the example environment 200 of FIG. 2 may include a plurality of devices, including intelligent, multi-sensing, network-connected devices, that seamlessly integrate with each other and/or with a central server or a cloud-computing system to provide any of a variety of useful smart home objectives, including hazard-detection objectives in accordance with the principles of the present disclosure. For example, the environment 200 may include one or more intelligent, multi-sensing, network-connected thermostats 212, one or more intelligent, multi-sensing, network-connected hazard detection units 214, and one or more intelligent, multi-sensing, network-connected entryway interface devices or doorbells 216. In general, a particular smart thermostat 212 may detect ambient climate characteristics, such as temperature and/or humidity, and control an HVAC (Heating, Ventilating, and Air Conditioning) system 218 accordingly, such as by turning ON and/or OFF a fan of the HVAC system 218.

When the fan of the HVAC system 218 is on, the fan operates to circulate air between the rooms 204 of the structure 202, and to exhaust air from the structure 202 and draw fresh, outside air into the structure 202. In contrast, a particular hazard detector 214 may detect the presence of a hazardous condition or a substance indicative of a hazardous condition, such as smoke, fire, heat, carbon monoxide, and etc. It will be appreciated that the smart devices of the example environment 200 may not only be integrated into the structure 202 itself. For example, a particular hazard detector 214 may be installed to a garage 220 that is separate from the structure 202 itself. Still may other examples are possible.

As shown, the example environment 200 further includes one or more intelligent, multi-sensing, network-connected wall switches 222, along with one or more intelligent, multi-sensing, network-connected wall plug interfaces 224. In general, a particular smart wall switch 222 may detect ambient lighting conditions, detect room-occupancy states, control a power and/or dim state of one or more lights, and etc. In some examples, a particular instance of a smart wall switch 222 may also control a power state or speed of a fan, such as a ceiling fan. In general, a particular smart wall plug interface 224 may detect occupancy of a room or enclosure and control supply of power to one or more wall plugs so that power is not supplied to a plug if nobody is home or in a particular room for example.

As shown, the example environment 200 further includes a plurality of intelligent, multi-sensing, network-connected appliances 226, such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. Each of the appliances 226 are contemplated as being compatible with other elements of the example environment 200 by cooperating with the respective manufacturers of the appliances. For example, the appliances can be space heaters, window air conditioning units, motorized duct vents, etc. When plugged in, a particular appliance 226 may announce itself to the smart home network of FIG. 2, such as by indicating what type of appliance it is, and it can automatically integrate with the controls of the smart home. Such communication may be facilitated by any particular wired or wireless communication protocols that which may or may not be implementation-specific.

The example environment 200 may further include a variety of non-communicating legacy appliances 228, such as old conventional washer/dryers, refrigerators, and the like which can be controlled, such as ON/OFF, by virtue of the smart wall plug interfaces 224. The example environment 200 can further include a variety of other devices, systems, and appliances 229, such as IR (Infrared) controlled wall air conditioners or other IR-controlled devices, which can be controlled by IR signals provided by the hazard detectors 214 or the smart wall switches 222. Still many other types of smart devices may be incorporate into the example environment 200, and such devices and corresponding technology of the same may evolve as technology evolves.

By virtue of network connectivity, one or more of the smart home devices of FIG. 2 may further allow a user to interact with the device even if the user is not proximate to the device. For example, a user can communicate with a device using a computer such as a desktop computer, laptop computer, tablet, etc., or other portable electronic device such as a smartphone 230. A webpage or app can be configured to receive communications from the user and control the device based on the communications and/or to present information about the device's operation to the user. For example, the user can view a current set-point temperature for a device and adjust it using a computer. The user can be in the structure during this remote communication or outside the structure.

As discussed, users can control the smart thermostat and other smart devices in the example environment 200 using a network-connected personal computer or portable, mobile device 230. In some examples, some or all of the occupants who live in the home, for instance, may register any particular mobile device 230 with the example environment 200. Such registration may be perfected at a central server to authenticate the occupant and/or the device as being associated with the home, and to give permission to the occupant to use the device to control the smart devices in the home. Further, an occupant can use their mobile device 230 when registered for example to remotely control the smart devices of the home, such as when the occupant is at work or on vacation, etc. The occupant may also use their mobile device 230 when registered for example to control the smart devices when the occupant is actually located inside the home, such as when the occupant is sitting on a couch inside the home. Instead of or in addition to registering devices, one or more components of the example environment 200 may be configured and/or arraigned to make inferences about which individuals live in the home and are therefore occupants and which devices are associated with those individuals. As such, the example environment 200 in general may learn or derive or infer who is an occupant and permit devices associated with such individuals to control the smart devices in the example environment 200.

In some examples, in addition to containing processing and sensing capabilities, it is contemplated that each of the smart devices in the example environment 200 may be capable of data communications and information sharing with any other of the smart devices, as well as to any central server or cloud-computing system or any other device that is network-connected anywhere in the world. The required data communications can be carried out using any of a variety of custom or standard wireless protocols, such as WiFi, ZigBee®, or 6LoWPAN for example, and/or any of a variety of custom or standard wired protocols, such as CAT6 Ethernet, or HomePlug® for examples According to examples, all or some of the smart devices in the example environment 200 may serve as wireless or wired repeaters. For example, a first one of the smart devices can communicate with a second one of the smart device via a wireless router 232. The smart devices can further communicate with each other via a connection to a network 234, such as the Internet. Through the Internet, the smart devices may communicate with a central server(s) or a cloud-computing system(s) 236, hereinafter system 236. The system 236 may be associated with a manufacturer, support entity, service provider associated with the device, etc. In one example, a user may be able to contact customer support using a device itself rather than needing to use other communication means such as a telephone or Internet-connected computer. Further, software updates may be automatically sent from the system 236 to the smart devices in the example environment 200 such as when available, purchased, at routine intervals, and etc.

According to examples, the smart devices in the example environment 200 may communicate or combine to create an ad-hoc mesh network of "spokesman" and "low-power" nodes, where some of the smart devices are spokesman nodes and others are low-powered nodes. Here, it is contemplated that some of the smart devices in the example environment 200 may generally be battery powered, while others may have access to a regular and reliable power source, such as by connecting to line-voltage wires behind or within the walls 206 of the structure 202. The smart devices that have a regular and reliable power source may be referred to as spokesman nodes. These nodes are equipped with the capability of using any wireless protocol or manner to facilitate bidirectional communication with any of a variety of other devices in the example environment 200, as well as with the system 236. On the other hand, the devices that are battery-powered may be referred to as low-power nodes. These nodes tend to be smaller than spokesman nodes and may only communicate using wireless protocols that requires very little power, such as Zigbee®, 6LoWPAN, and etc. Further, some, but not all, low-power nodes may be incapable of bidirectional communication. These nodes may send messages, but may be are unable to listen.

As described, the smart devices serve as low-power and spokesman nodes to create a mesh network in the example environment 200. Individual low-power nodes in the smart home environment may regularly broadcast messages regarding what they are sensing and the other, low-powered nodes in the smart home environment, in addition to sending out their own messages, may repeat the messages, thereby causing the messages to be transferred from node to node or device to device throughout the example environment 200. The spokesman nodes in the example environment 200 may be able to drop down to low-powered communication protocols to receive these messages, translate the messages to other communication protocols, and send the translated messages to other spokesman nodes and/or the system 236. Thus, the low-powered nodes using low-power communication protocols may send messages across the entire example environment 200 as well as over the network 234 to the system 236. According to examples, the mesh network enables the system 236 to regularly receive data from all of the smart devices in the home, make inferences based on the data, and send commands back to one or more of the smart devices to accomplish some of the smart home objectives as discussed throughout.

As described, the spokesman nodes and some of the low-powered nodes are capable of listening. Accordingly, users, other devices, and the system 236 may communicate controls to the low-powered nodes. For example, a user may use the mobile device 230 to send commands over the network 234 to the system 236, which then may relay commands to the spokesman nodes in the example environment 200. The spokesman nodes may drop-down to a low-power protocol to communicate the commands to the low-power nodes throughout the example environment 200, as well as to other spokesman nodes that did not receive the commands directly from the system 236.

An example of a low-power node is a particular hazard detector 214. Other examples of low-powered nodes include battery-powered versions of a hazard detector 214. Such hazard detectors 214 may in some instances be located in an area without access to a constant and reliable power source, and may include any number and type of sensors, such as smoke/fire/heat sensors, carbon monoxide/dioxide sensors, occupancy/motion sensors, ambient light sensors, temperature sensors, humidity sensors, and the like. Furthermore, hazard detectors 214 may send messages to other smart devices, sensors, etc., within the example environment 200, as well as the system 236, such as via ad-hoc mesh network techniques as contemplated above.

Examples of spokesman nodes include smart doorbells 216, smart thermostats 212, wired versions of hazard detectors 214, smart wall switches 222, and smart wall plugs interfaces 224. These devices may be located near and connected to a reliable power source, and therefore might include more power-consuming components, such as one or more communication chips capable of bidirectional communication in any variety of protocols. In some examples, the low-powered and spokesman nodes of the example environment 200 may function as alarm broadcasters for a hazard-detection system in the example environment 200. For example, in the event a particular hazard detector 214 detects a hazardous condition, such dangerous amounts of smoke or carbon monoxide, that hazard detector 214 may send an alarm message to the system 236, which may then instruct other smart devices in the example environment 200 to instantiate an alarm, alerting occupants or other individual to or of the dangerous condition. Thus, the hazard-detection system could be enhanced by various low-powered and spokesman nodes located throughout the example environment 200, all capable of providing audible, visual. In this example, a user could enhance the safety of the example environment 200 by purchasing and installing extra smart devices capable of alerting occupant to dangerous conditions.

Figure 3:
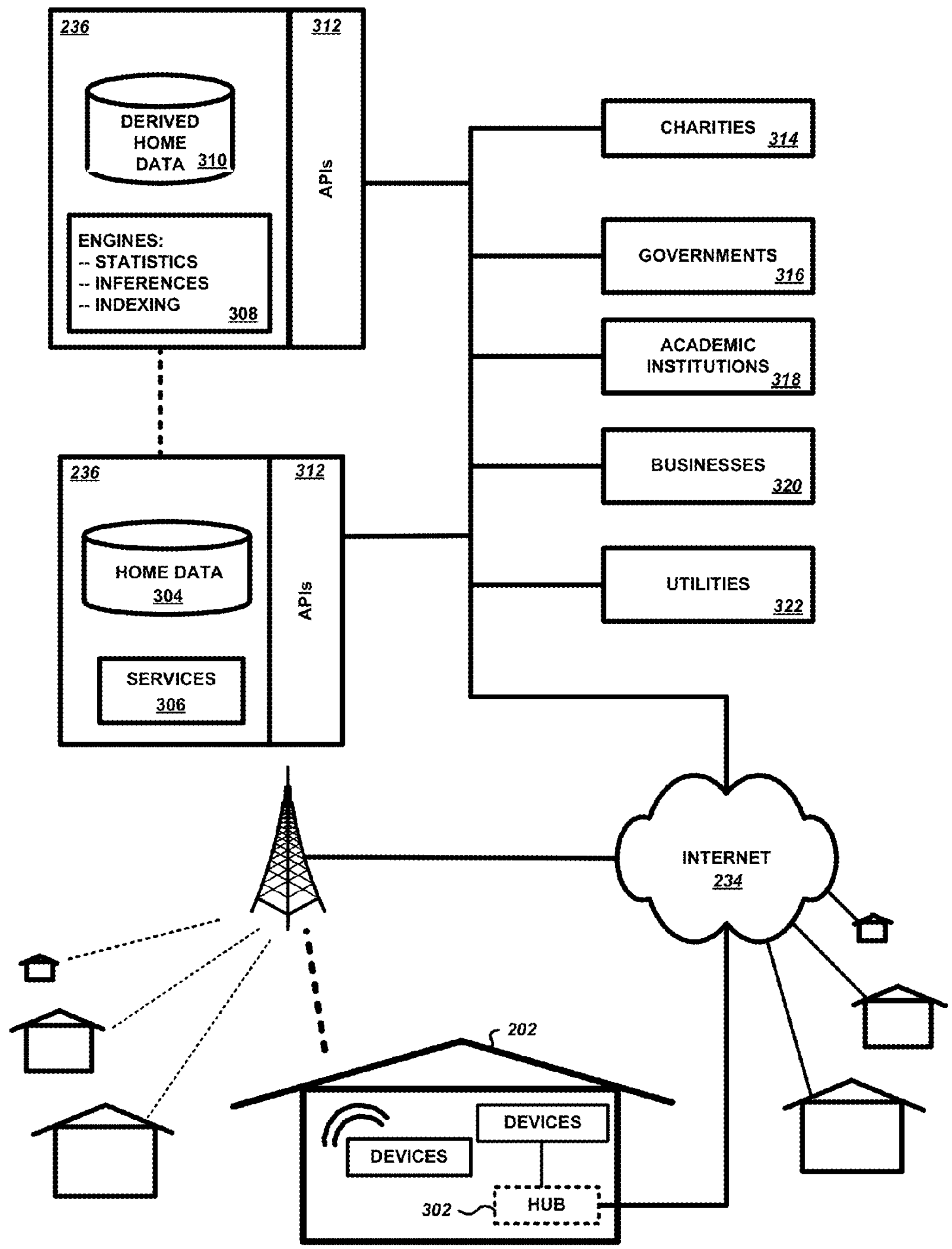
FIG. 3 shows an example extensible platform according to the disclosure.

Referring now to FIG. 3, a network-level view of an extensible devices and services platform 300 is shown with which a plurality of smart home environments, such as the example environment 200 of FIG. 2, may be integrated. In this example, the platform 300 is shown to include various remote servers or cloud computing architectures. As mentioned above, it is contemplated that each of the intelligent, network-connected smart devices of FIG. 2 may regularly communicate with the remote servers or cloud computing architectures. For example, a connection to the network 234 may be established either directly, for example via 3G/4G connectivity to a wireless carrier, through a hub network 302 (see also hub 223 of FIG. 2 example) which may be a scheme or implementation ranging from a simple wireless router, for example, up to and including an intelligent, dedicated whole-home control node, and/or through any combination thereof.

Although in some examples provided herein, elements of the example platform 300 may communicate with and collect data from various smart devices of the example environment 200 of FIG. 2, it is further contemplated that one or more elements of the example platform 300 may communicate with and collect data from a plurality of smart home environments across the world. For example, the system 236 (see also FIG. 2) may collect particular home data 304 from devices of one or more smart home environments, where the devices may routinely or regularly such as periodically or at least intermittently transmit home data or in response to a particular command to do so. Thus, various elements of the example platform 300 may routinely collect data from homes across the world. In general, the home data 304 may include, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, and so on and so forth in which the type of home data 304 as collected is only limited by type or form of smart devices as incorporated into a particular environment, such as the example environment 200 of FIG. 2.

According to examples, smart devices may increase their logging frequency as they approach a threshold. For example, a particular hazard detector 214 may increases the frequency at which it samples air and sends corresponding data to the system 236 as the condition in the home approaches an alarm condition. For example, upon detecting more than a threshold level of smoke, a particular hazard detector 214 may samples air at a higher rate and send corresponding data to the system 236. In another example, a particular hazard detector 214 may increases the frequency it samples air for CO upon detecting a threshold level increase in the amount of CO in the home. Further, for example, a particular hazard detector 214 may increase logging and sampling frequency during transitions. For example, upon detecting increased levels of noise, light, etc., in a particular location, a particular hazard detector 214 may switch into a listening state where its PIR (Passive Infrared Sensor), ultrasonic and other sensors, etc., and sample and log, and possibly send to the system 236, at an increased rate or frequency. The increased levels of noise, light, etc., in the location may indicate the presence of humans in the room, and thereby indicates that there may be data worth observing in the room.

For example, it may be desirable that the smart devices be quiet most of the time so as to reduce chatter on the network, e.g., to reduce frequent updates at the system 236. Thus, if no one is in the room, a smart device may be configured to sample once a minute or once an hour. However, if the smart device senses a transition indicating that a person is in the room, then it will sample more often. For example, when the room is occupied, the smart device may send to the system 236 temperature data, occupancy data, etc. The server stores this data in home data 304 and runs trend detecting algorithms against the data. For example, the home data 304 may include logs and maps of user in-home movements from room to room, time spent in each room, intra-home occupancy/density maps, etc. In some examples, the home data 304 may be stored to a persistent memory location of a particular hazard detector 214 itself.

According to examples, the home data 304 may be made available to, and/or to smart devices themselves, so users so that they can review a log of historical events in the home. For example, end-users may review historical CO, smoke, temperature, etc., levels of the various rooms of the home. For instance, an example historical log may indicate or include data such as: pre-alarm smoke level detected at 10:14 AM; smoke alarm level at 10:26 AM; alarm hushed at 10:31 AM; and smoke diminished "everything okay" at 10:50 AM. This may enable the user to see that an alarm condition occurred in the home and how it was resolved. The historical log may also include a history of self-checks executed by a particular smart device. For example, the historical log may show a history of time the hazard detectors 214 have tested their CO sensors. An example self-check log may indicate that all hazard detectors in the home self-checked between 1 AM and 2 AM, and they are all working properly, including their WiFi connection is of sufficient strength, their battery level is acceptable, their CO sensor is working properly, and etc. Still further, a historical log may be leveraged as part of an algorithm to enable a hazard detector 214 to self-adjust its own settings, such as particular threshold level settings for example. Still many other examples are possible and it will be appreciated that such historical data may be mined, manipulated, and leveraged to implement many of the various features and/or aspects contemplated within the present disclosure.

Referring still to the system 236, it is contemplated that the system 236 may further provide one or more services 306. The services 306 may include, for example, software updates, customer support, sensor data collection/logging, remote access, remote or distributed control, or use suggestions such as based on home data 304 as collected and/or aggregated to improve performance, reduce utility cost, and etc. Data associated with the services 306 may be stored at the example system 236, and the system 236 may retrieve and transmit the data at an appropriate time such as at regular intervals, upon receiving a request from a user, and etc.

As illustrated in FIG. 3, the example platform 300 may further include a processing engine 308, which may be concentrated at a single server or distributed among several different computing entities, without limitation. The processing engine 308 may include a number of engines configured and/or arranged to receive data from devices of smart home environments, possibly via the network 234 and/or the hub network 302, to index the data, analyze the data, and/or to generate statistics based on the analysis or as part of the analysis. The analyzed data may in some examples be stored as derived home data 310. Results of the analysis or statistics may thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings may be generated by the processing engine 308 and transmitted. The results or statistics may be provided via the network 234. In this manner, the processing engine 308 may be configured and programmed to derive a variety of useful information from the home data 304. A single server can include one or more engines. Still other examples are possible.

The derived data can be highly beneficial at a variety of different granularities for a variety of useful purposes, ranging from explicit programmed control of the devices on a per-home, per-neighborhood, or per-region basis for example, demand-response programs for electrical utilities, to the generation of inferential abstractions that can assist on a per-home basis, for example, an inference can be drawn that the homeowner has left for vacation and so security detection equipment can be put on heightened sensitivity, to the generation of statistics and associated inferential abstractions that can be used for government or charitable purposes. For example, processing engine 308 may generate statistics about device usage across a population of devices and send the statistics to device users, service providers or other entities for example that have requested or may have provided monetary compensation for the statistics.

In some examples, to encourage innovation and research and to increase products and services available to users, the example platform 300 may expose a range of API's (Application Programming Interface) 312 to third parties, such as charities 314, governmental entities 316, such as the Food and Drug Administration or the Environmental Protection Agency, academic institutions 318, such as university researchers, businesses 320, such as for providing device warranties or service to related equipment, targeting advertisements based on home data, utility companies 322, and various other third parties. In general, the APIs 312 may be coupled to and permit third-party systems to communicate with the example system 236, including the services 306, the processing engine 308, the home data 304, and the derived home data 310. For example, the APIs 312 may allow applications executed by the third parties to initiate specific data processing tasks that are executed by the system 236, as well as to receive dynamic updates to the home data 304 and the derived home data 310.

Figure 4:
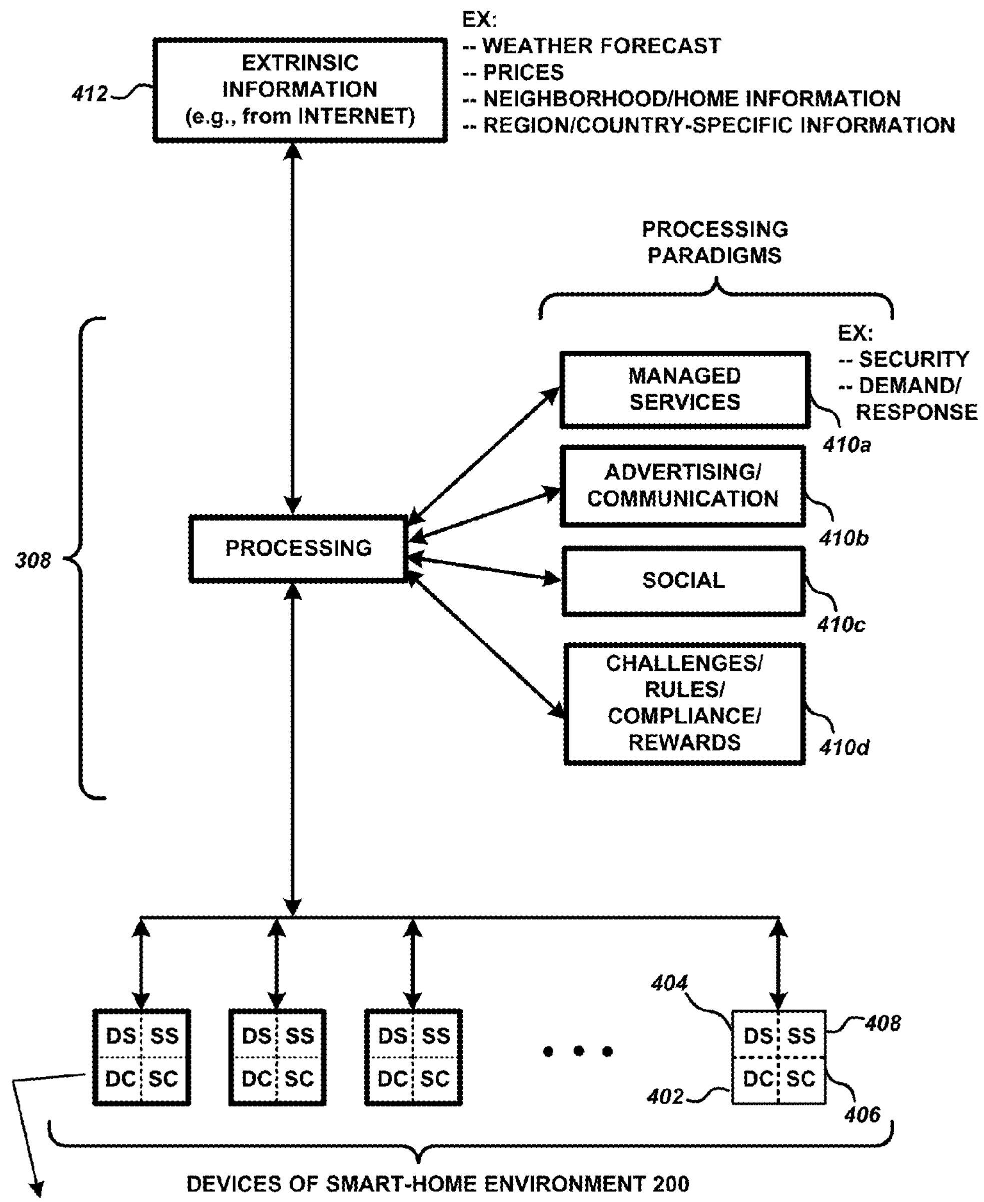
FIG. 4 shows another example of the extensible platform of FIG. 3.

Referring now to FIG. 4, an abstracted functional view of the example platform 300 of FIG. 3 is shown, with particular reference to the processing engine 308, as well as other elements or devices such as shown and described above in connection with FIG. 2. Even though devices situated in smart home environments will have an endless variety of different individual capabilities, they can all be thought of as sharing common characteristics in that each of them is a DC (Data Consumer) 402, a DS (Data Source) 404, a SC (Services Consumer) 406, and a SS (Services Source) 408. Advantageously, in addition to providing control information needed for the devices to achieve their local and immediate objectives, elements of the example platform 300 may also be configured to harness the large amount of data that is flowing out of these devices. In addition to enhancing or optimizing the actual operation of the devices themselves with respect to their immediate functions, elements of the example platform 300 may be directed to "repurposing" that data in a variety of automated, extensible, flexible, and/or scalable ways to achieve a variety of useful objectives. These objectives may be predefined or adaptively identified based on, e.g., usage patterns, device efficiency, and/or user-input, e.g., requesting specific functionality.

For example, the processing engine 308 of FIG. 4 is shown to include a number of paradigms 410. For example, the processing engine 308 may include a managed services paradigm **410*a* that monitors and manages primary or secondary smart device functions. The device functions may include ensuring proper operation of a device given user-inputs, estimating that an intruder is or is attempting to be in a dwelling, detecting a failure of equipment coupled to the device, implementing or otherwise responding to energy demand response events, or alerting a user of a current or predicted future event or characteristic. The processing engine 308 may further include an advertising/communication paradigm 410***b* that estimates characteristics such as demographic information, desires and/or products of interest of a user based on device usage. Services, promotions, products or upgrades can then be offered or automatically provided to the user. The processing engine 308 may further include a social paradigm 410*c* that uses information from a social network, provides information to a social network for example based on device usage, and/or processes data associated with user and/or device interactions with the social network platform.

The processing engine 308 may include a challenges/rules/compliance/rewards paradigm 410*d* that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to live safely by reducing exposure to toxins or carcinogens for example, to conserve money and/or equipment life, to improve health, etc. For example, one challenge may involve participants turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

In accordance with the principles of the present disclosure, the processing engine 308 may further integrate or otherwise utilize extrinsic information 412 from extrinsic sources to improve the functioning of one or more processing paradigms. Extrinsic information 412 can be used to interpret data received from a device, to determine a characteristic of the environment near the device such as weather outside a structure that the device is enclosed in, to determine services or products available to the user, to identify a social network or social-network information, to determine contact information of entities, e.g., public-service entities such as an emergency-response team, the police or a hospital, near the device, etc., to identify statistical or environmental conditions, trends or other information associated with a home or neighborhood or region such as a county, town, city, state, and so forth.

Figure 5:
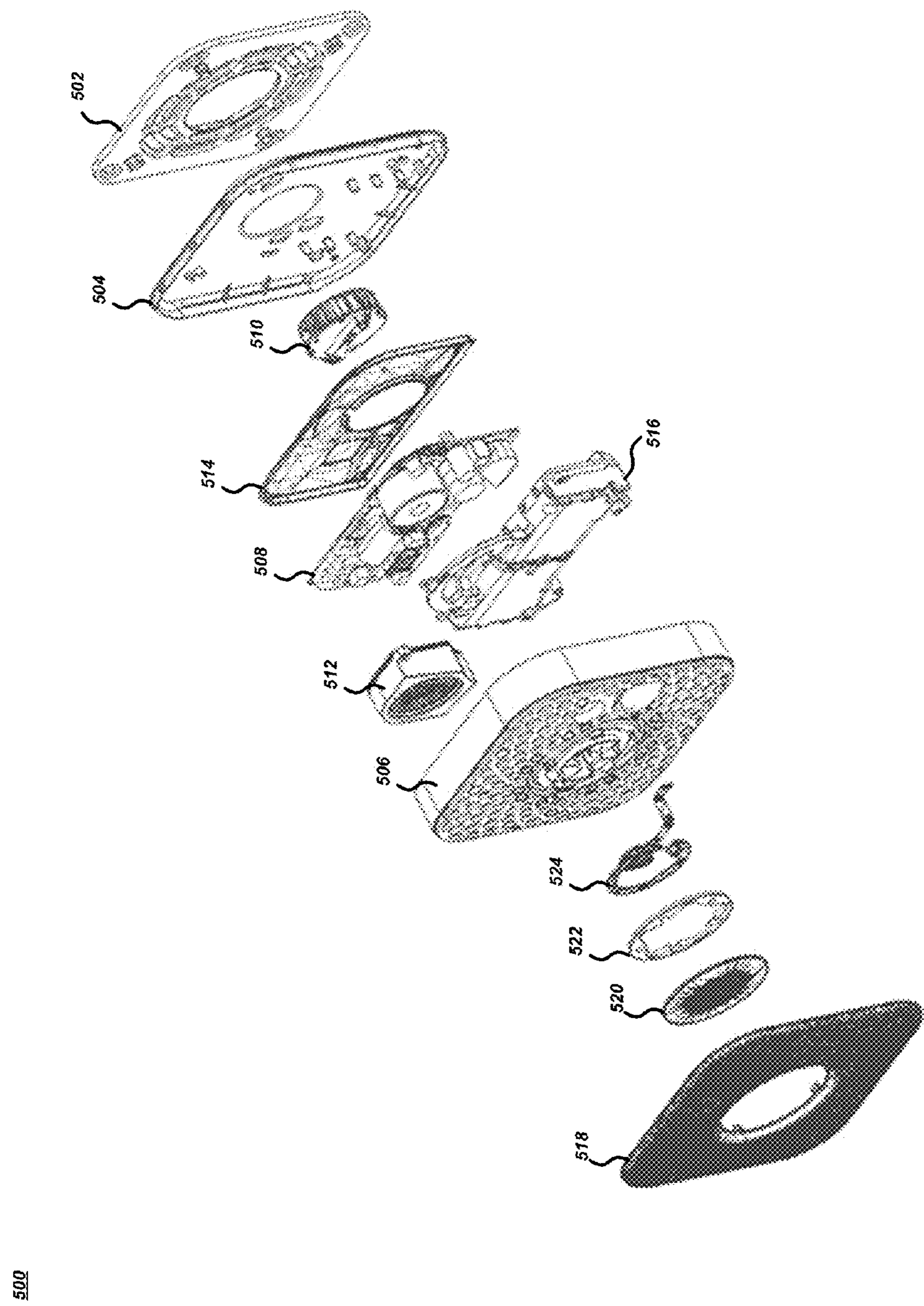
FIG. 5 shows a view of an example hazard detector according to the disclosure.
Figure 6:
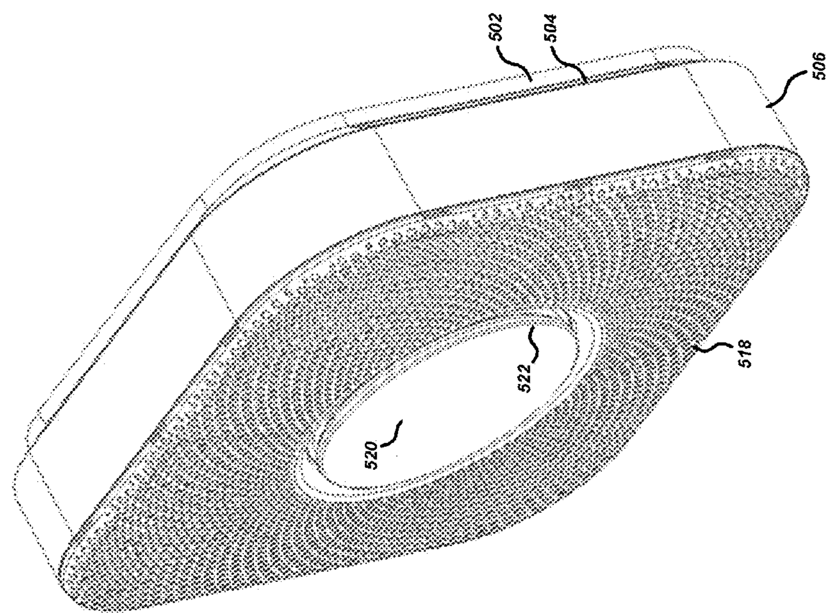
FIG. 6 shows another view of the detector of FIG. 5.

Referring now to FIG. 5 and FIG. 6, an example smart hazard detector 500 that may be incorporated into the example environment 200 of FIG. 2 is shown in accordance with the principles of the present disclosure. Another view of the example hazard detector 500 is shown below in connection with at least FIG. 31. In one example, the hazard detector 500 corresponds to the hazard detector 214 described in other sections of this disclosure, such as in connection with FIG. 2. FIG. 5 illustrates an exploded perspective view of the hazard detector 500, while FIG. 6 illustrates an assembled view of the same hazard detector 500. In an example, the hazard detector 500 is a smoke detector that is configured to detect the presence of smoke and sound an alarm to audibly warn an occupant or occupants of the home or structure of a potential fire or other danger. In other examples, the hazard detector 500 may be a carbon monoxide detector, heat detector, and the like. In other examples, the hazard detector 500 may be a multi-sensing detector that includes a smoke detector, carbon monoxide detector, heat detector, motion detector, and the like. Many of the present teachings are particularly advantageous for examples in which the hazard detector 500 is a multi-sensing detector, particularly since combining the various sensing modes together into a single device can pose substantial challenges with respect to one or more of device compactness, component powering, and overall component governance and coordination.

In one example implementation, the hazard detector 500 is a roughly square or rectangular shaped object having a width of approximately 120 mm to 134 mm and a thickness of approximately 38 mm. Stated differently, hazard detector 500 is a multi-sensing unit having a fairly compact shape and size that may be easily attached to a wall or ceiling of a home or structure so as to be able, among other functionalities, to detect the presence of smoke and alert an occupant therein of the potential fire danger. As shown in FIG. 5, the hazard detector 500 includes a mounting plate 502 that may be attached to a wall of the building or structure to secure the hazard detector 500 thereto. The hazard detector 500 also includes a back plate 504 that may be mounted to the mounting plate 502 and a front casing 506 that may be coupled with or otherwise secured to the back plate 504 to define a housing having an interior region within which components of the hazard detector 500 are contained.

A circuit board 508 may be coupled with or attached to the back plate 504. Various components may be mounted on the circuit board 508. For example, a smoke chamber 510 may be coupled with or mounted on the circuit board 508 to detect the presence of smoke. In one example, the smoke chamber 510 may be mid-mounted relative to the circuit board 508 so that air may flow into the smoke chamber 510 from a position above the circuit board 508 and the below circuit board 508. A speaker 512 and/or alarm device, the alarm device may be a separate component from the speaker 512, may also be mounted on the circuit board 508 to audibly warn, for example, an occupant of a potential fire danger when the presence of smoke is detected via the smoke chamber 510. Other components, such as a motion sensor, e.g., ultrasonic, passive IR, etc., CO sensor, temperature sensor, heat sensor, ambient light sensor, noise sensor, microprocessor, and the like, may further be mounted on the circuit board 508 possibly accordingly to implementation-specific requirements.

In one example, a protective plate 514 may be attached to or otherwise coupled with the circuit board 508 to provide a visually pleasing appearance to the inner components of hazard detector 500 and/or to funnel or direct airflow to the smoke chamber 510. For example, when the internal components of the hazard detector 500 are viewed, such as through vents in the back plate 504, the protective plate 514 may provide the appearance of a relatively smooth surface and otherwise hide or obscure the components or circuitry of the circuit board 508. The protective plate 514 may likewise function to direct a flow of air from the vents of the back plate 504 toward the smoke chamber 510 to facilitate air flow into and out of the smoke chamber 510.

The hazard detector 500 may also include a battery pack 516 that provides power to the various components of hazard detector 500 when the hazard detector 500 is not coupled with an external power source, such as a 120 V power source. A cover plate 518 may be coupled with the front casing 506 to provide a visually pleasing appearance to hazard detector 214 and/or for other functional purposes. In a specific example, the cover plate 518 may include a plurality of holes or openings that allow one or more sensors coupled with the circuit board 508 to view or see through a surface of cover plate 518 so as to sense objects external to the hazard detector 500. The plurality of openings of the cover plate 518 may be arranged to provide a visually pleasing appearance when viewed by occupants of the home or structure. In one example, the plurality of openings of the cover plate 518 may be arranged according to a repeating pattern, such as a Fibonacci or other sequence. Still other examples are possible.

A lens button 520 may be coupled with or otherwise mounted to the cover plate 518. The lens button 520 may allow one or more sensors to view through the lens button 520 for various purposes. For instance, in one example a PIR sensor may be positioned behind the lens button 520 and configured to view through the lens button 520 to detect the presence of an occupant or occupants within the home or structure. In some examples, the lens button 520 may also function as a button that is depressible by a user to input various commands to the hazard detector 500, such as to shut-off an alarm that is triggered in response to a false or otherwise harmless condition. Positioned distally behind the lens button 520 may be a light ring 522 that receives light, such as from an LED (Light Emitting Diode) or another light emitting element, and disperse the light within the light ring 522 to provide a desired visual appearance or cue, such as a halo behind the lens button 520. Positioned distally behind the light ring 522 may be a flexible circuit board 524 that includes one or more electrical components, such as a PIR sensor, LEDs, and the like. The flexible circuit board or flexible ring 524 may be electrically coupled with the circuit board 508 to communicate and/or receive instructions from one or more microprocessors mounted on a circuit board during operation of hazard detector 500.

Referring now specifically to FIG. 6, the hazard detector 500 of FIG. 5 is shown in an assembled state. Specifically, the mounting plate 502, front casing 506, back plate 504, and cover plate 518 are in an assembled configuration with the various other components contained within an interior space of hazard detector 500. FIG. 6 also shows the plurality of holes or openings of cover plate 518 forming an aesthetically-pleasing design, and the lens button 520 is shown attached to the hazard detector 500 so as to be centrally positioned with respect to the cover plate 518. As briefly described above, the light ring 522 may be used to provide a halo appearance of light around and behind lens button 520. The hazard detector 500 when assembled provides a compact yet robust and multifunctional device.

Figure 7:
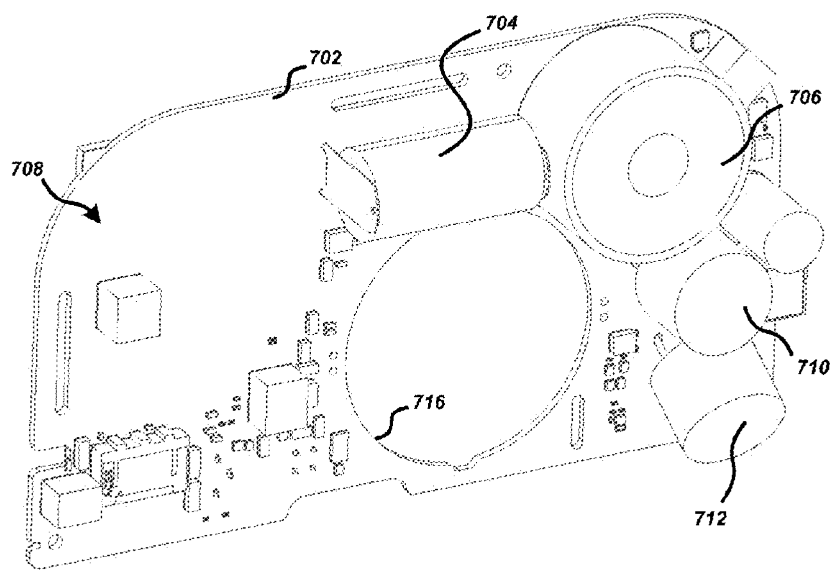
FIG. 7 shows views of an example circuit board of the detector of FIG. 5.
Figure 7:
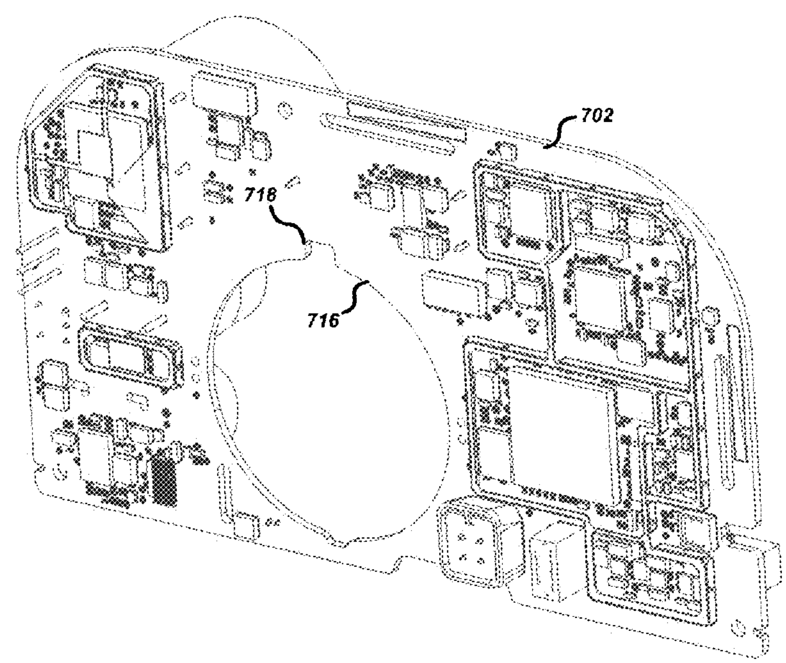

Referring now to FIG. 7, illustrated are front and rear perspective views of the circuit board 508 of FIG. 5. In this example, the circuit board 508 includes a main body 702 having a front side or surface and a rear side or surface. Various electrical components may be mounted on circuit board 508, and type and form of such components may or may not be implementation-specific, and may evolve as technology evolves. In some examples, these components may be mounted on the front surface of circuit board 508, on the rear surface of circuit board 508 opposite the front surface, or on both surfaces of the circuit board 508. For instance, in a specific example one or more microprocessors and/or other processor related components may be mounted on the rear surface of circuit board 508 facing the protective plate 514 while one or more functional components such as alarm device, CO detector, speaker, motion sensors, WiFi device, Zigbee® device, and the like, are mounted on a front surface of circuit board 508 facing a room of the home or structure in which the hazard detector 500 is positioned. Other components may be mid-mounted relative to the circuit board 508 so that opposing surfaces are positioned on opposing sides of the circuit board 508 as described herein.

In a specific example the front surface of circuit board 508 may include a CO detector 704 that detects the presence of carbon monoxide gas and triggers an alarm device 706 if the CO gas levels are determined to be too high. The alarm device 706, which can be a piezoelectric buzzer having an intentionally shrill or jarring sound, may likewise be mounted on the front surface of the circuit board 508 so as to face an occupant of the room in which the hazard detector 500 is positioned to alarm the occupant of a potential danger. The alarm device 706 may produce one or more sounds or signals to alert the occupant of the potential danger.

The front surface may further include an area 708 in which the speaker 512 is positioned. The speaker 512 provide audible warnings or messages to the occupant of the room. For example, the speaker 512 may alert the occupant of a potential danger and instruct the occupant to exit the room. In some examples, the speaker 512 may provide specific instructions to the occupant, such as to guide installation of the hazard detector 500. Other messages may likewise be communicated to the occupant, such as to alert the occupant that the batteries are low, that CO levels are relatively high in the room, that the hazard detector 500 needs periodic cleaning, or alert the occupant of any other abnormalities or issues related to the hazard detector 500 or components thereof.

The circuit board 508 may also include one or more motion sensors mounted on the front surface thereof. The motion sensors may be used to determine the presence of an individual within a room or surrounding area of the hazard detector 500. This information may be used to change the functionality of the hazard detector 500 and/or one or more other devices connected in a common network as described previously. For example, this information may be relayed to a smart thermostat to inform the thermostat that occupants of the home or structure are present so that the smart thermostat may condition the home or structure according to one or more learned or programmed settings. The hazard detector 500 may likewise use this information for one or more purposes, such as to quiet the alarm device, such as via a gesture hush, or for various other reasons.

In one example, a first ultrasonic sensor 710 and a second ultrasonic sensor 714 may be mounted on the front surface of circuit board 508. The two ultrasonic sensors, 710 and 714, may be offset axially so as to point in slightly different directions. In this orientation, each ultrasonic sensor may be used to detect the motion of an individual based on an orientation of the hazard detector 500 relative to the room and/or occupant, and determine distance from the hazard detector 500 and one or walls or surface near or adjacent the hazard detector 500. Detecting the motion of the individual may be used to quiet the alarm device as described herein or for any other reason. In one example, an axis of the first ultrasonic sensor 710 may be oriented substantially outward relative to hazard detector 500 while an axis of the second ultrasonic sensor 714 is oriented at an angle relative to the axis of first ultrasonic sensor 710. The first ultrasonic sensor 710 may sense motion of an individual when the hazard detector 500 is mounted on a ceiling of the home or structure.

Because the first ultrasonic sensor 710 is oriented substantially outward relative to hazard detector 214, the first ultrasonic sensor 710 essentially looks straight down on individuals beneath hazard detector 500 when the same is installed to a ceiling for example. The second ultrasonic sensor 714 may similarly sense motion of the individual when the hazard detector 500 is mounted on a wall of the home or structure. Because the second ultrasonic sensor 714 is oriented at an angle relative to the first ultrasonic sensor 710 and hazard detector 500, the second ultrasonic sensor essentially looks downward toward the floor when the hazard detector 500 is mounted on a wall of the home or structure, rather than looking directly outward as first ultrasonic sensor 710. In one example, the angular offset of the two ultrasonic sensors may be approximately 30° or any other desired value. Other examples are possible, and may vary depending on intended use. For example, a different configuration may be leveraged in scenarios in which the two ultrasonic sensors, 710 and 714 are further, or alternatively, or additionally, intended to assist in installation of the hazard detector 500.

For instance, in another example, the two ultrasonic sensors, 710 and 714, may be replaced by a single ultrasonic sensor that is configured to rotate within hazard detector 500 so that the single ultrasonic sensor is capable of looking straight outward similar to first ultrasonic sensor 710 or capable of looking downward similar to second ultrasonic sensor 714. The single ultrasonic sensor may be coupled to circuit board 508 via a hinge that allows the ultrasonic sensor to rotate based on the orientation of hazard detector 500. For example, when the hazard detector 500 is mounted to a ceiling of the home or structure, gravity may orient the ultrasonic sensor so as to look straight downward; whereas when hazard detector 500 is coupled to a wall of the home or structure, gravity may cause the ultrasonic sensor to rotate via the hinge and look downward toward a floor and relative to hazard detector 500. In another example, a motor may be coupled with the single ultrasonic sensor so as to rotate the ultrasonic sensor based on the orientation of the hazard detector 500. In this manner, the ultrasonic sensor may always point in a direction that is likely to detect motion of an individual within the room or space surrounding the hazard detector 500. In yet another example, the single ultrasonic sensor may have a wide field of view that is able to substantially accommodate both mounting positions of the two ultrasonic sensors 710 and 714.

As shown in FIG. 7, the main body 702 of the circuit board 508 also includes a substantially centrally located aperture 716 through which the smoke chamber 510 may be inserted so as to mid-mount the smoke chamber 510 relative to the circuit board 508. The aperture 716 may also include a pair of notches 718 through which wires are inserted to electrically couple the smoke chamber 510 with the circuit board 508. Mid-mounting of the smoke chamber 510 through an aperture 716 may allow smoke and air to enter the smoke chamber 510 from both the front surface or side of the circuit board 508 and the rear surface or side of circuit board 508. Included on the circuit board 508 may be several other components, including a system processor, relatively high-power wireless communications circuitry and antenna, relatively low-power wireless communications circuitry and antenna, non-volatile memory, speaker 512, one or more interface sensors, a safety processor, safety sensors, alarm device 706, a power source, and powering circuitry.

The components are operative to provide failsafe safety detection features and user interface features using circuit topology and power budgeting methods that minimize power consumption. According to one example, a bifurcated or hybrid processor circuit topology or architecture is used for handling the various features of the hazard detector 500, wherein the safety processor is a relatively small, relatively lean or thin processor that is dedicated to core safety sensor governance and core alarming functionality as would be provided on a conventional smoke/CO alarm, and wherein the system processor is a relatively larger, relatively higher-powered processor that is dedicated to more advanced features such as cloud communications, user interface features, occupancy and other advanced environmental tracking features, and more generally any other task that would not be considered a "core" or "conventional" safety sensing and alarming task.

By way of example, the safety processor may be a Freescale KL15 microcontroller, while the system processor may be a Freescale K60 microcontroller. The safety processor may be programmed such that it is capable of operating and performing its core safety-related duties regardless of the status or state of the system processor. Thus, for example, even if the system processor is not available or is otherwise incapable of performing any functions, the safety processor will continue to perform its core safety-related tasks such that the hazard detector 500 still meets all industry and/or government safety standards that are required for the smoke, CO, and/or other safety-related monitoring for which the hazard detector 500 is offered.

The system processor, on the other hand, performs what might be called optional or advanced functions that are overlaid onto the functionality of the safety processor, where optional or advanced may refer to tasks that are not specifically required for compliance with industry and/or governmental safety standards. Thus, although the system processor is designed to interoperate with the safety processor in a manner that can improve the overall performance, feature set, and/or functionality of the hazard detector 500, its operation is not required in order for the hazard detector 500 to meet core safety-related industry and/or government safety standards. Being generally a larger and more capable processor than the safety processor, the system processor will generally consume more power than the safety processor when both are active.

Similarly, when both processors are inactive, the system processor will still consume more power than the safety processor. The system processor can be operative to process user interface features and monitor interface sensors, such as occupancy sensors, audio sensors, cameras, for example, which may not be directly related to core safety sensing). For example, the system processor may direct wireless data traffic on both high and low power wireless communications circuitry, access non-volatile memory, communicate with the safety processor, and cause audio to be emitted from the speaker 512. As another example, the system processor may monitor interface sensors to determine whether any actions need to be taken, for example to shut off an active alarm in response to a user detected action to "hush" the alarm.

The safety processor may be operative to handle core safety related tasks of the hazard detector 500. The safety processor can poll safety sensors, such as smoke and/or CO sensors for example, and activate the alarm device 706 when one or more of safety sensors indicate that a hazard event is detected. The safety processor can operate independently of the system processor and can activate the alarm device 706 regardless of what state the system processor is in. For example, if the system processor is performing an active function, such as performing a WiFi update for example, or is shut down due to power constraints, the safety processor may still activate the alarm device 706 when a hazard event is detected.

In some examples, the software running on the safety processor may be permanently fixed and may never be updated via a software or firmware update after the hazard detector 500 leaves the factory. Compared to the system processor, the safety processor is a less power consuming processor. Using the safety processor to monitor the safety sensors, as opposed to using the system processor to do this, can yield power savings because safety processor may be constantly monitoring the safety sensors. If the system processor were to constantly monitor the safety sensors, power savings may not be realized. In addition to the power savings realized by using safety processor for monitoring the safety sensors, bifurcating the processors can also ensure that the safety features of the hazard detector 500 always work, regardless of whether the higher level user interface works. The relatively high power wireless communications circuitry can be, for example, a WiFi module capable of communicating according to any of the 802.11 protocols.

By way of example, the relatively high power wireless communications circuitry may be implemented using a Broadcom BCM43362 WiFi module. The relatively low power wireless communications circuitry can be a low power Wireless Personal Area Network (6LoWPAN) module or a ZigBee® module capable of communicating according to a 802.15.4 protocol. For example, in one example, the relatively low power wireless communications circuitry may be implemented using an Ember EM357 (6LoWPAN) module. The non-volatile memory can be any suitable permanent memory storage such as, for example, NAND Flash, a hard disk drive, NOR, ROM, or phase change memory. In one example, the non-volatile memory can store audio clips that can be played back using the speaker 512. The audio clips can include installation instructions or warnings in one or more languages. The interface sensors can includes sensors that are monitored by the system processor, while the safety sensors can include sensors that are monitored by the safety processor.

The interface sensors may include, for example, an ALS (Ambient Light Sensor), such as could be implemented using a discrete photodiode, a noise sensor, a PIR motion sensor, such as could be implemented using an Excelitas PYQ1348 module, and one or more ultrasonic sensors, such as could be implemented using one or more Manorshi MS-P2360H12TR modules. The safety sensors can include, for example, the smoke chamber 510, which could employ or leverage for example an Excelitas IR module, the CO module 704, which could employ or leverage for example a Figaro TGS5342 sensor, and a temperature and humidity sensor, which could employ or leverage for example a Sensirion SHT20 module. The power source may supply power to enable operation of the hazard detector and can include any suitable source of energy. Examples discussed herein can include AC line power, battery power, a combination of AC line power with a battery backup, and externally supplied DC power, such as USB (Universal Serial Bus) supplied power. Examples that use AC line power, AC line power with battery backup, or externally supplied DC power may be subject to different power conservation constraints than battery only examples.

Preferably, battery-only powered examples are designed to manage power consumption of a finite energy supply such that hazard detector 500 operates for a minimum period of time of at least seven, eight, nine, or ten years. Line powered examples are not as constrained. Line powered with battery backup examples may employ power conservation methods to prolong the life of the backup battery. In battery-only examples, the power source can include one or more batteries, such as the battery pack 516. The batteries may be constructed from different compositions, such alkaline or lithium iron disulfide for example, and different end-user configurations, such as permanent, user replaceable, or non-user replaceable for example, may be used. In one example, six cells of $LiFeS_2$ may be arranged in two stacks of three. Such an arrangement may yield about 27000 mWh of total available power for the hazard detector 500. Other examples are possible.

Figure 8:
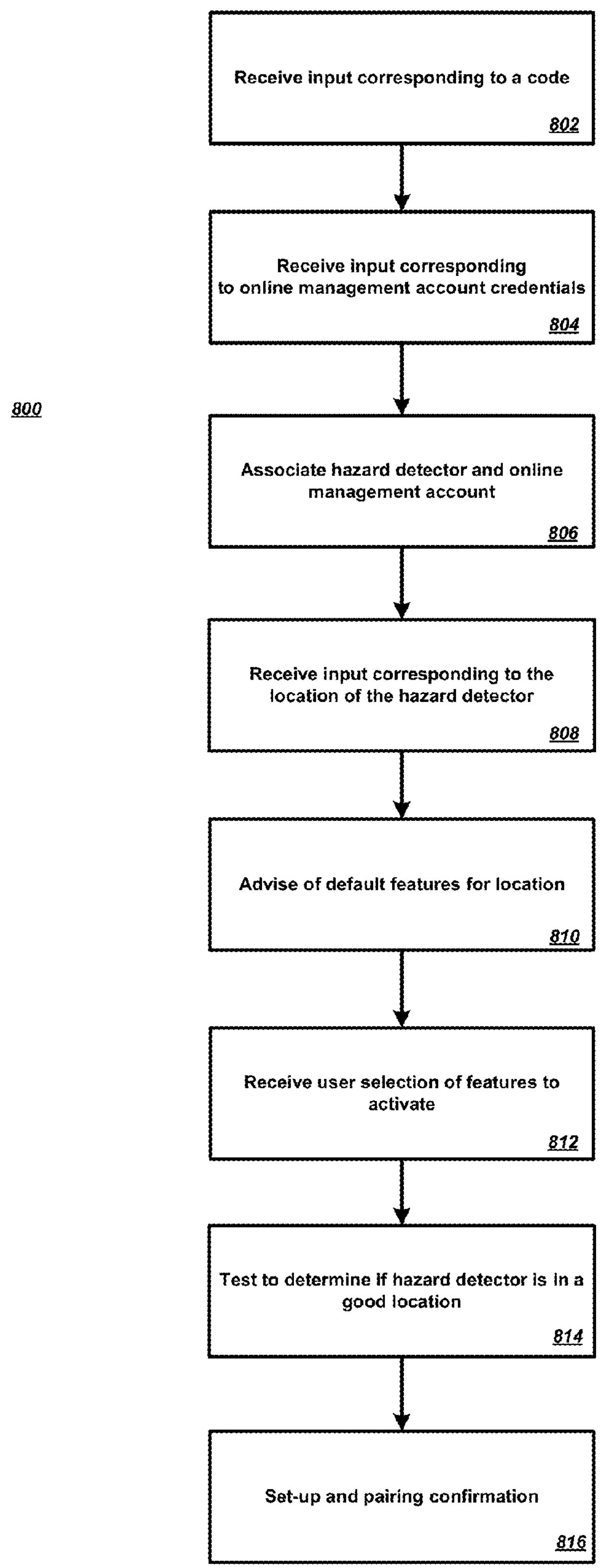
FIG. 8 shows a second example method according to the disclosure.

Referring now to FIG. 8, an example method 800 for setting up a hazard detector and establishing a pairing between the hazard detector and an online management account is shown according to the principles of the present disclosure. Each step of the example method 800 is discussed in detail below, and some steps are discussed with reference to additional figures that may provide physical illustrations related to the steps of the example method 800. The method 800 is an exemplary method of setting up and pairing a hazard detector, some illustrated steps may not be necessary or applicable and other, additional steps may be appropriate or implemented as desired, the same of which may or may not be implementation-specific.

At step 802, a central server or a cloud-computing system, e.g., system 236 of FIG. 2, may receive input corresponding to a code. This code may be correspond to a unique identifier or ID of a hazard detector, such as hazard detector 500. The code may also be associated with additional information stored on a server or system, e.g., the manufacture date of the hazard detector 500, the software version that was initially installed on the hazard detector and/or other information about the hazard detector. Before the server can receive this code in step 802, a user first may obtain the code from the hazard detector 500. The code may be contained in the product packaging of the hazard detector or displayed on the hazard detector and provided to the system 236 via an app or a webpage configured to provide communication to the system 236.

Figure 9:
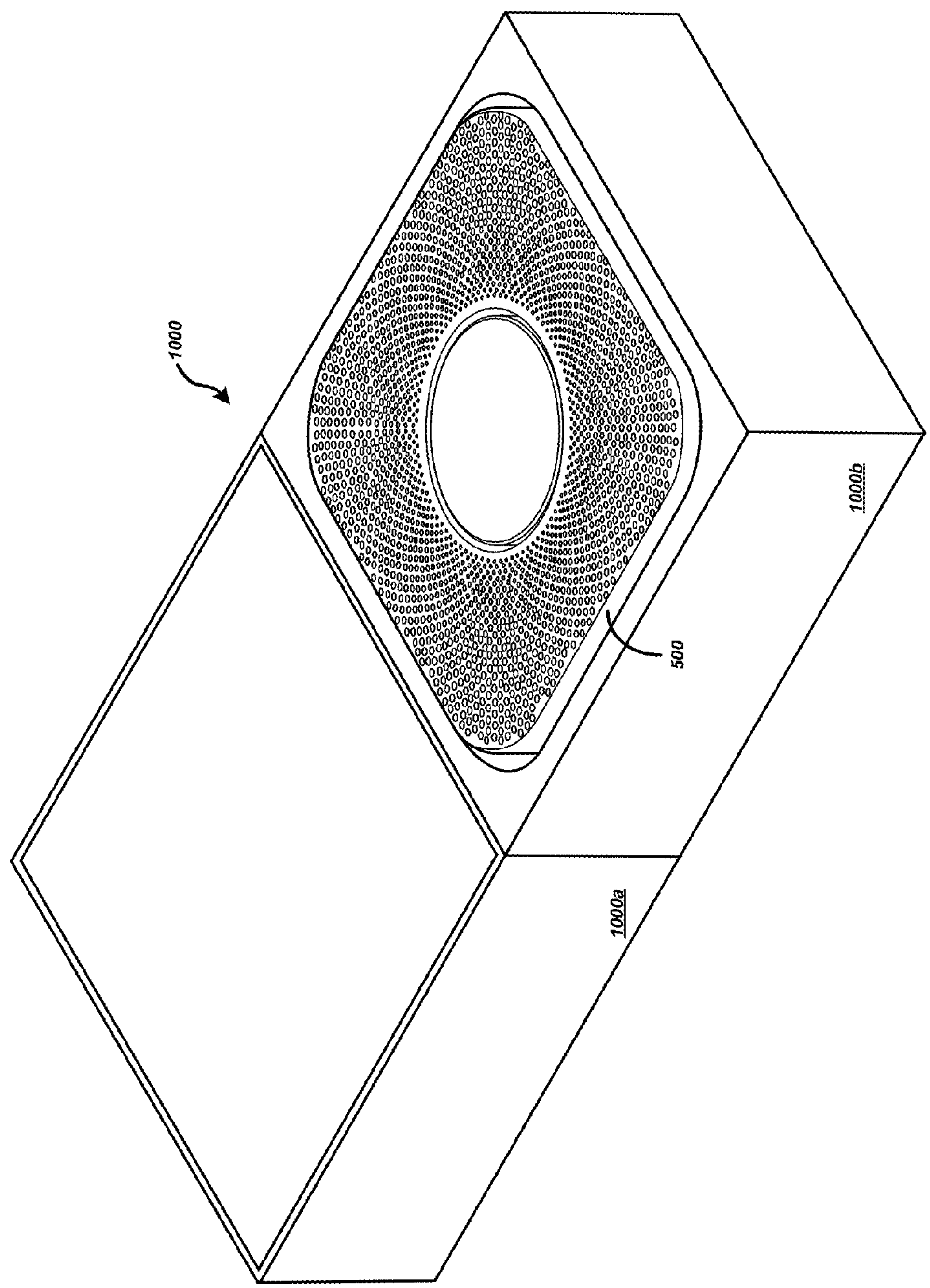
FIG. 9 shows the detector of FIG. 5 in-box.
Figure 10:
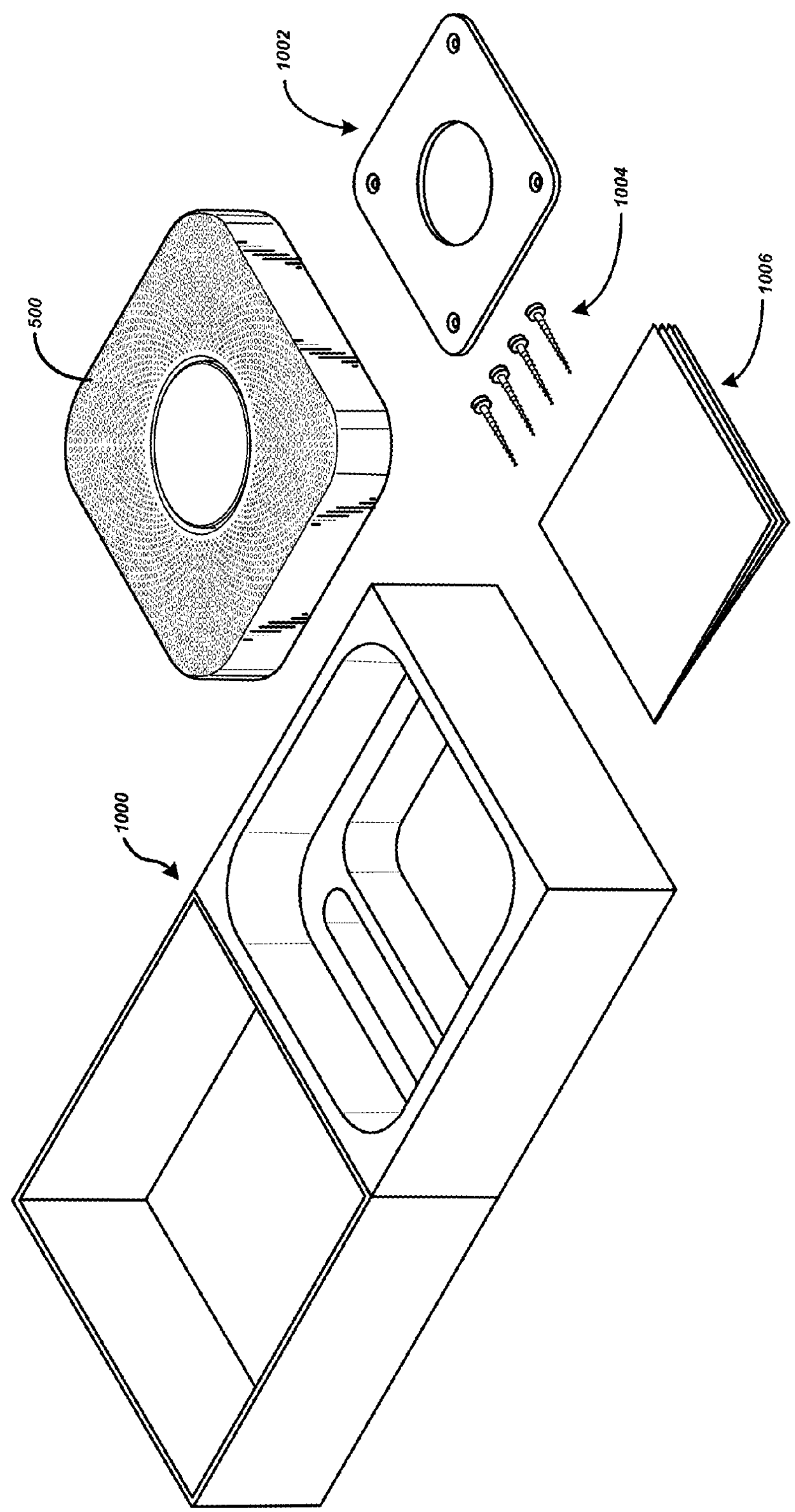
FIG. 10 shows the detector of FIG. 5 out-of-box.

Referring now additionally to FIGS. 9-16, an example physical process for obtaining the mentioned code and providing it for the server to receive the code is shown according to the principles of the present disclosure. Firstly, the hazard detector 500 may be removed from its product packaging. This may be accomplished by separating top and bottom portions 1000*a-b* of the box 1000, exposing the hazard detector 500, as shown in FIG. 9. Then, the hazard detector 500 may be removed from the box 1000, along with the other contents of the box 1000, as shown in FIG. 10. The other contents may include a mounting plate 1002, e.g., mounting plate 502, fasteners 1004 for securely affixing the mounting plate 1002 to a wall of a home or other structure, and a hazard detector information packet 1006. In some examples, it may be necessary for a user to pull a battery tab in order to expose the terminals of the batteries, e.g., the batteries of battery pack 516, and provide operating power or backup power to hazard detector 500.

Figure 11:
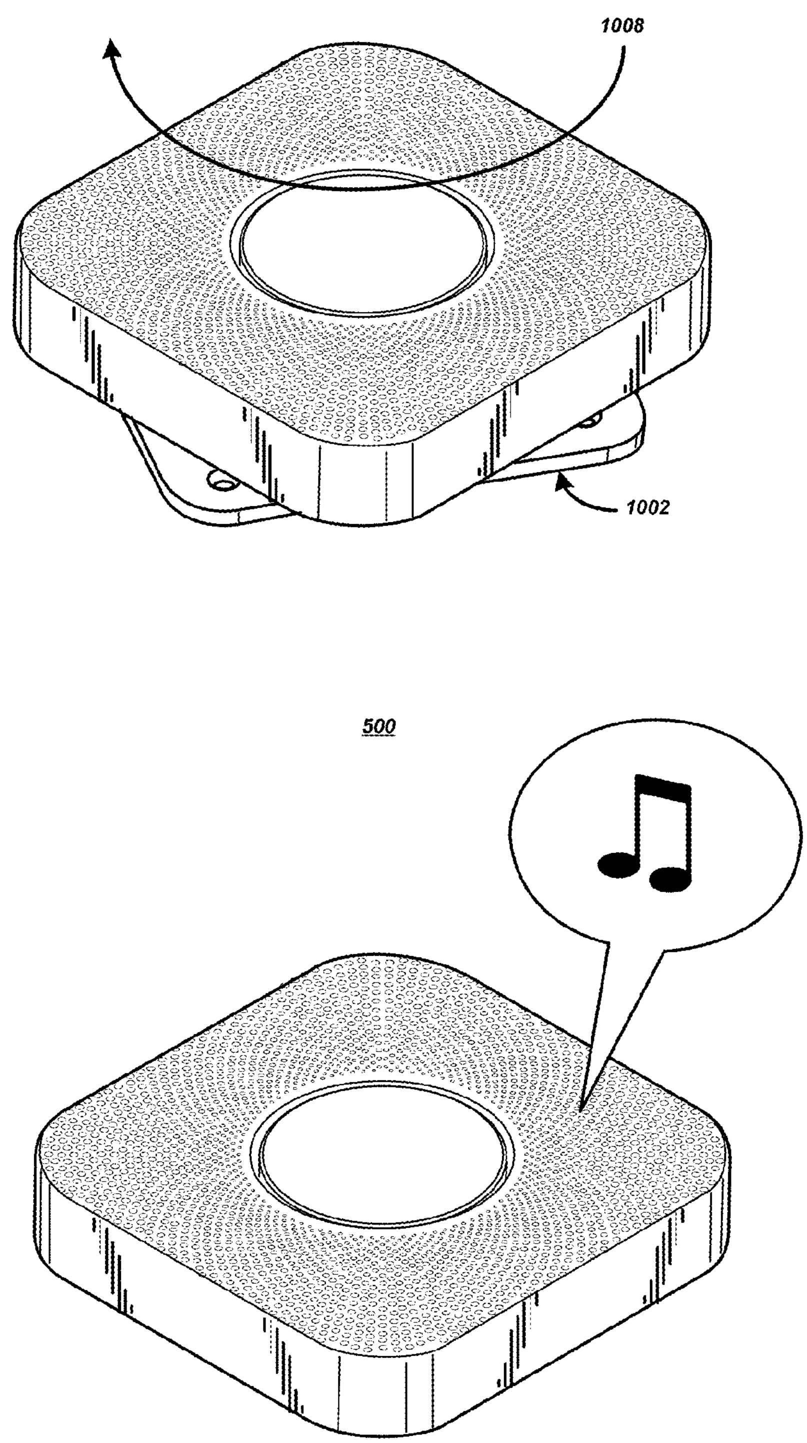
FIG. 11 shows the detector of FIG. 5 in a first and second example state.

The hazard detector 500 and the mounting plate 1002 may include corresponding features such that hazard detector 500 becomes locked onto mounting plate 1002 when a user twists the hazard detector 500 in a rotational direction 1008, as shown in FIG. 11. The hazard detector 500 may also include circuitry and sensors that cause the hazard detector 500 to "boot-up" or initiate its operating system when the sensors detect that hazard detector 500 has been mounted on mounting plate 1002. As shown in FIG. 11, the hazard detector 500 may generate music to indicate that it is booting up, e.g., the hazard detector 500 may generate music via speaker 512. Alternatively, the hazard detector 500 may generate any form of an audio indication, such as tones, speech, etc., and/or visual indication, such as LED lights that may produce light according to a predetermined pattern.

Figure 12:
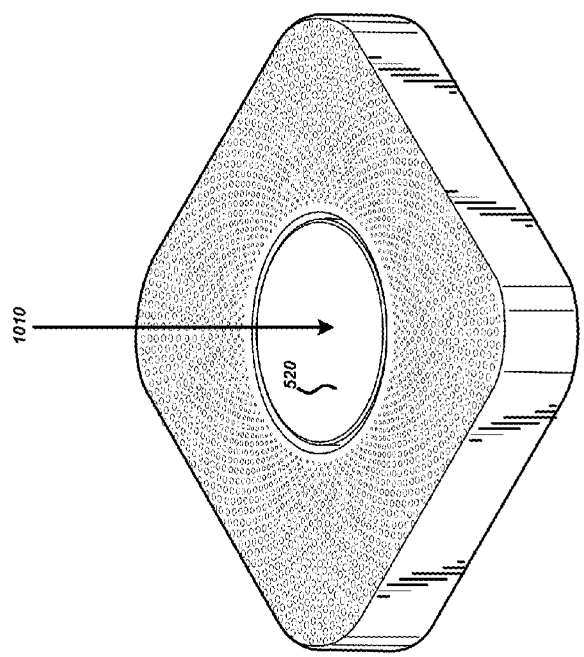
FIG. 12 shows a button of the detector of FIG. 5 being depressed.
Figure 13:
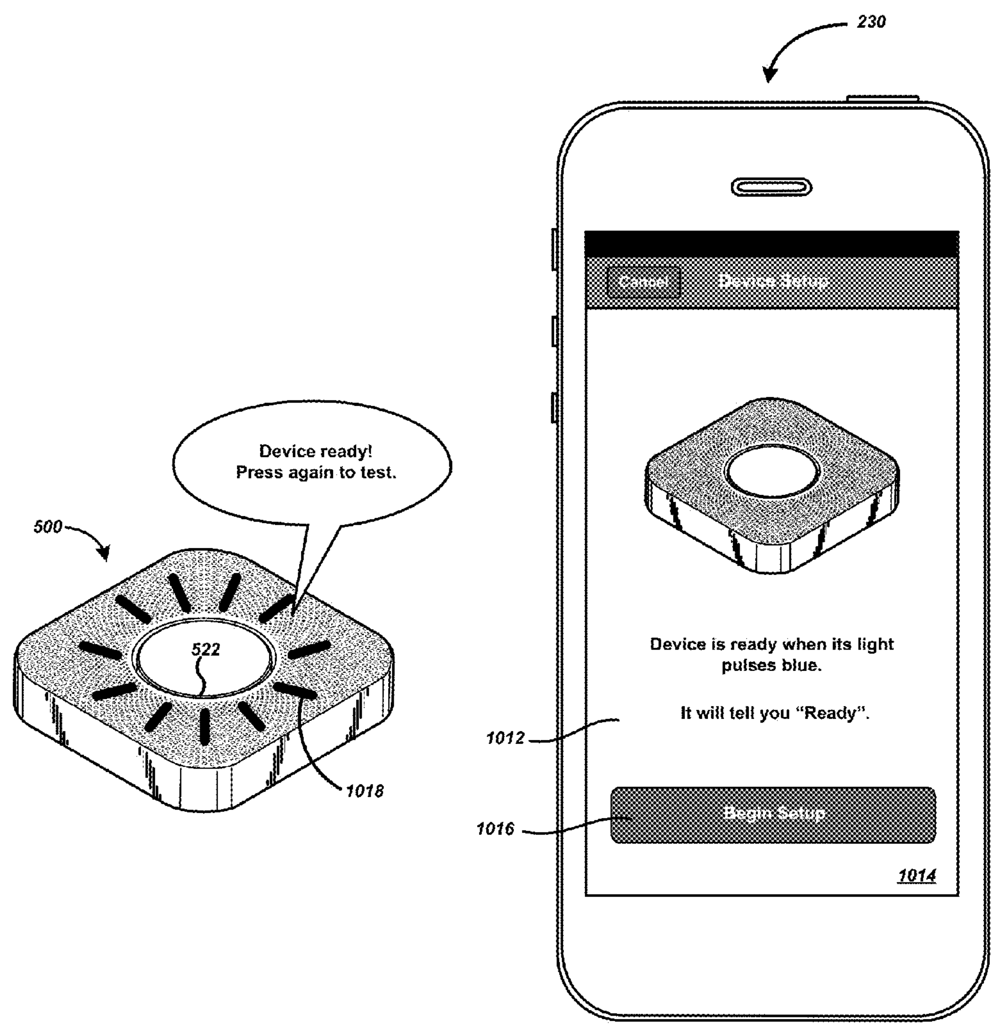
FIG. 13 shows an example configuration step of the detector of FIG. 5.

As shown in FIG. 12, after the hazard detector 500 has booted-up, a user may press the lens button 520 in a direction 1010 to begin communicating with the hazard detector 500. Alternatively, the user may use voice commands to begin communicating with the hazard detector 500. In response, the hazard detector 500 may generate audio and/or visual indicators, as shown in FIG. 13. For example, the hazard detector 500 may tell the user "Device ready! Press again to test." The hazard detector 500 may also generate pulsing blue light rays or other visual effects via the light ring 522. As discussed below, these audio and/or visual indicators direct or instruct the user to open an app or a webpage at a computing device in order to provide the code. The hazard detector 500 may also generate audio and/or visual indicators and receive input via the lens button 520 in order to allow the user to select a language preference for the operation of hazard detector 500.

FIG. 13 shows an app or application 1012, or, e.g., a webpage, that may among other things provide a user with instructions for the next steps of the setup process. For example, the application 1012 may be opened on a computing device, e.g., mobile device 230 as shown in FIG. 2, and provide an interface on a screen 1014 for leading a user through the next steps of the setup process. More specifically, FIG. 13 shows that application 1012 may inform a user that the "Device is ready when its light pulses blue" and etc. Accordingly, the user may select a setup button 1016 after hazard detector 500 pulses blue light rays 1018 and generates the following speech: "Ready." In some situations where application 1012 is not already installed on mobile device 230, the hazard detector may actually instruct the user to download and install application 1012 using audio (e.g., speech) and/or visual indicators.

Figure 14:
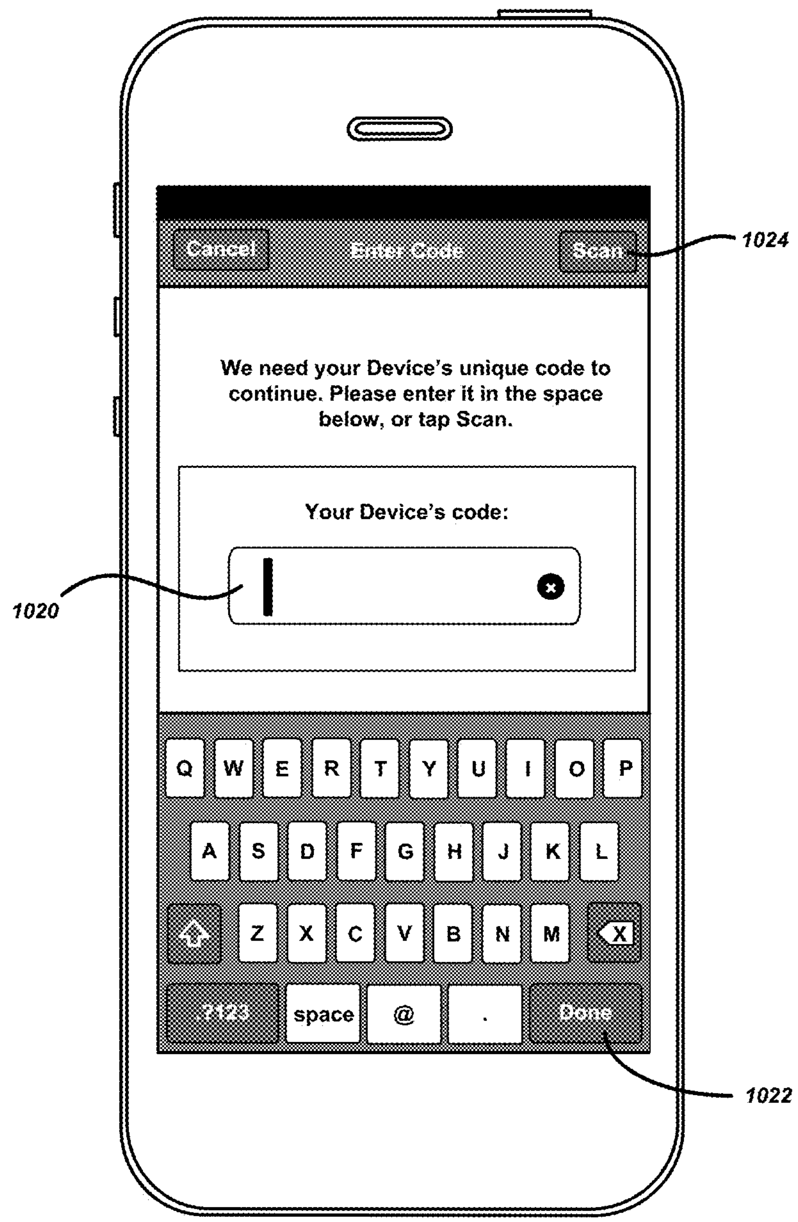
FIG. 14 shows another example configuration step of the detector of FIG. 5.
Figure 15:
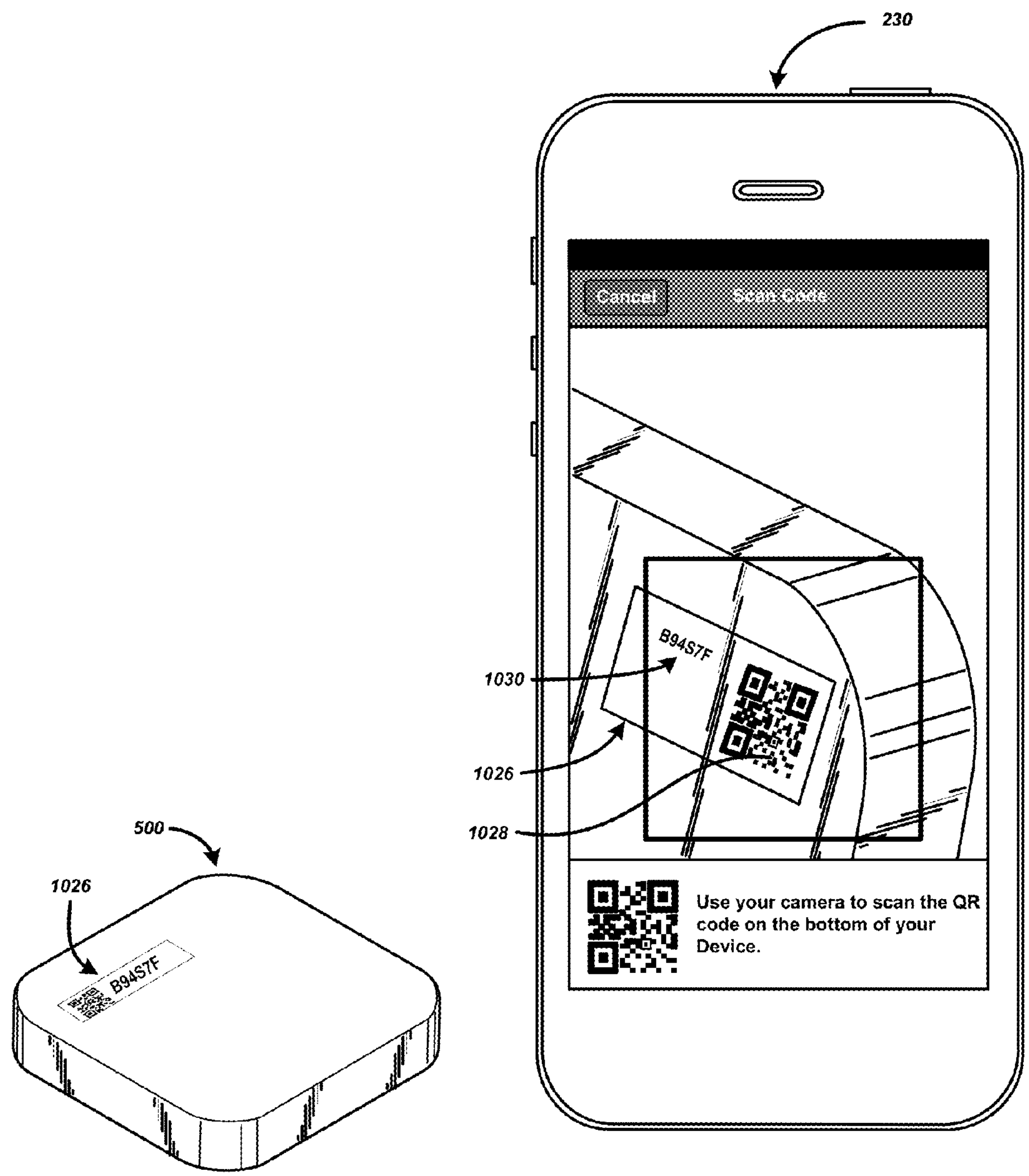
FIG. 15 shows yet another example configuration step of the detector of FIG. 5.

Selecting the setup button 1016 brings up an interface of the application 1012, as shown in FIG. 14, that instructs the user to provide the unique code for hazard detector 500. The user may enter an alphanumeric code manually in the field 1020 and select a done button 1022 when finished. Alternatively, the user may select a scan button 1024 to bring up an interface of the application 1012 as shown in FIG. 15. That interface may be used for scanning QR codes. The QR code and the alphanumeric code may be found on a sticker 1026 that is located on back plate 504 of hazard detector 500. As shown in FIG. 15, the application 1012 may enter a camera mode interface in order to allow a user to take a picture of a QR code 1028 located on the sticker 1026 and next to alphanumeric code 1030. The application 1012 may process the QR code 1028 in order to determine or otherwise identify the alphanumeric code 1030, another unique ID of hazard detector 500 or other information concerning hazard detector 500. The application 1012 may automatically input or populate the alphanumeric code 1030 into the field 1020 (shown in FIG. 16) following the scanning of QR code 1028.

Figure 16:
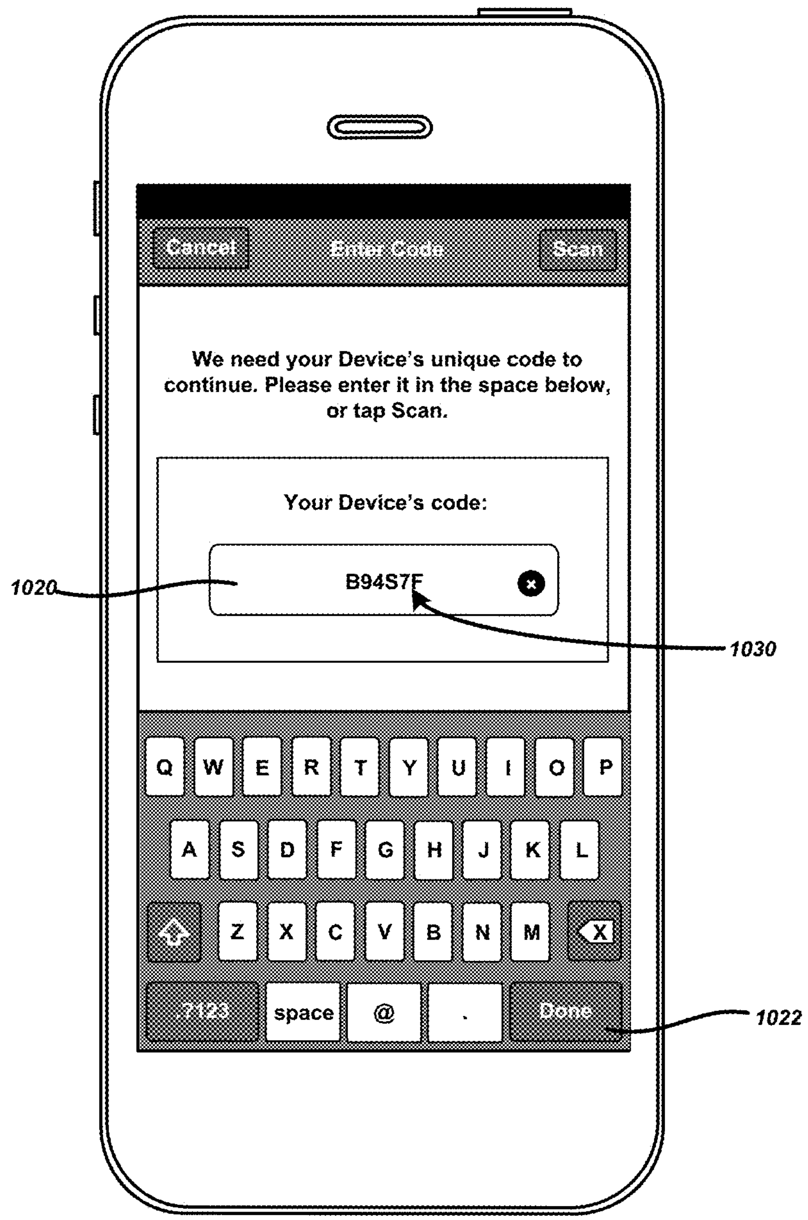
FIG. 16 shows yet another example configuration step of the detector of FIG. 5.

FIG. 16 shows the alphanumeric code 1030 inputted into the field 1020. Again, this may be accomplished by manually inputting the alphanumeric code 1030 into the field 1020 or by scanning the QR code 1028 (see FIG. 15) and allowing the application 1012 to determine and automatically populate the alphanumeric code 1030 into the field 1020. The user may then press the done button 1022 in order to send the alphanumeric code 1030 to the central server or a cloud-computing system or system 236.

In order for a central server to process and store a received hazard detector code, e.g., the alphanumeric code 1030, it may be necessary to associate that code with a user and/or a user's online management account. As discussed below, steps 804 and 806 of the method 800 may enable a central server to process and store a received hazard detector code, e.g., the alphanumeric code 1030. In particular, at step 804 of the example method 800, system or system 236 of FIG. 2 for example may receive input corresponding to credentials for accessing an online management account. For example, after detecting depression of the done button 1022 (see FIG. 16), the application 1012 may send credentials for an online management account, which credentials may have been previously stored on application 1012, to the system 236. These credentials may have been entered at the application 1012 at a previous time, e.g., after first opening the application 1012, or at some other time before beginning step 802 above. Alternatively, a user may be prompted to create an online management account after pressing the done button 1022. The online management account may be created at the application 1012 or a webpage configured to provide communication to system 236. The credentials for the newly created online management account may then be provided to the system 236 by or via the application 1012, e.g., in a manner similar to providing the alphanumeric code 1030 to the system 236 via the application 1012. Online management accounts, which may be uniquely identified by an email address for example may allow users to access or otherwise benefit from online services, e.g., services 306, as discussed above in connection with FIG. 2.

At step 806, a central server or a cloud-computing system, e.g., system 236, may associate the hazard detector 500 and an online management account using a code, e.g., the alphanumeric code 1030, and credentials for the online management account. This may also allow data, e.g., home data 304 of FIG. 3, to be collected, stored and linked to and/or accessible at a user's online management account. Additionally, this association may allow for remote access and/or remote or distributed control of the hazard detector 500 via a user's online management account. However, in order for data collected from and/or remote control of hazard detector 500 to be possible, the hazard detector 500 may need to have access to a network connection.

Figure 17:
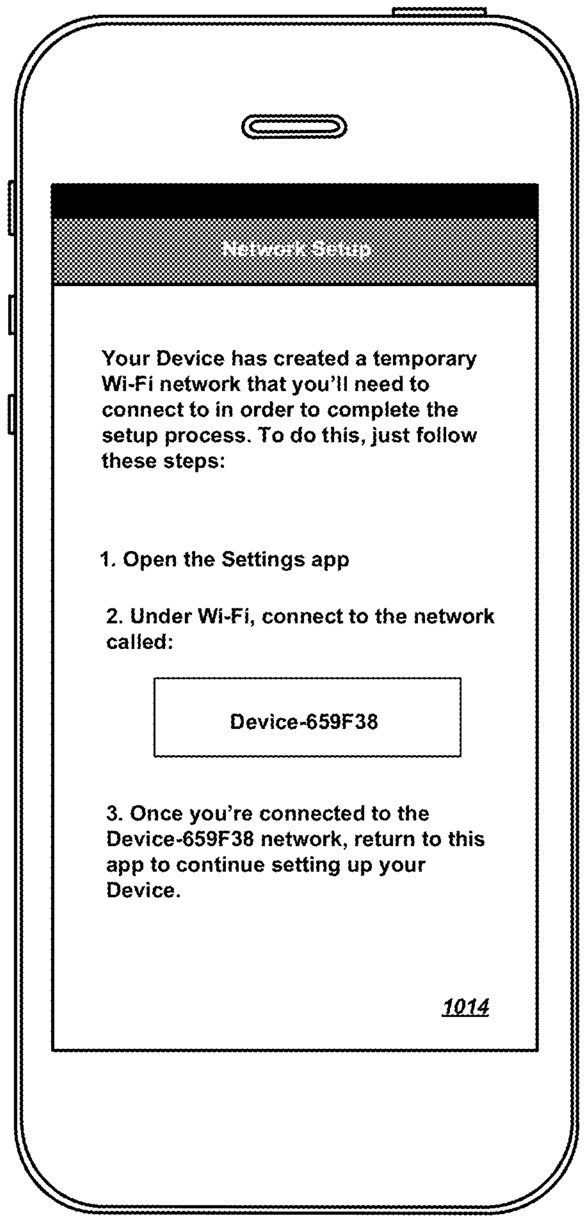
FIG. 17 shows yet another example configuration step of the detector of FIG. 5.

Referring now additionally to FIGS. 17-22, an example of a physical process for connecting the hazard detector 500 to the network 234 (see e.g., FIG. 2) is shown according to the principles of the present disclosure. For example, as shown in FIG. 17, an interface may be provided at or by the application 1012 on the mobile device 230 in order to provide instructions for connecting the hazard detector 500 to the network 234. For example, the instructions may comprise a number of steps for connecting the hazard detector 500 to the network 234 and continuing the setup process for hazard detector 500, including: (1) open the Settings app; and (2) under WiFi, connect to the network called "Device-659F38"; and (3) return to the application 1012 in order to complete the setting-up of the hazard detector 500. Some of these steps may be specific to type or form of the mobile device 230, which may for example correspond to the iPhone® by Apple, Inc. of Cupertino, Calif., but similar steps may be taken for other computing devices, e.g., tablets, laptops, netbooks, gaming consoles, all-in-one computers, and etc., in order to connect the same to the temporary network broadcasted by the hazard detector 500.

The "Device-659F38" network may be temporary WiFi network broadcasted by the hazard detector 500 during the setup process. Alternatively, the hazard detector 500 may broadcast one or more other networks for communicating with computing devices, e.g., the mobile device 230, using other wireless protocols, e.g., any of the other wireless protocols mentioned herein. This temporary network may provide a convenient, initial means for allowing the hazard detector 500 to communicate with the mobile device 230 while the hazard detector 500 is not connected to the network 234.

Figure 18:
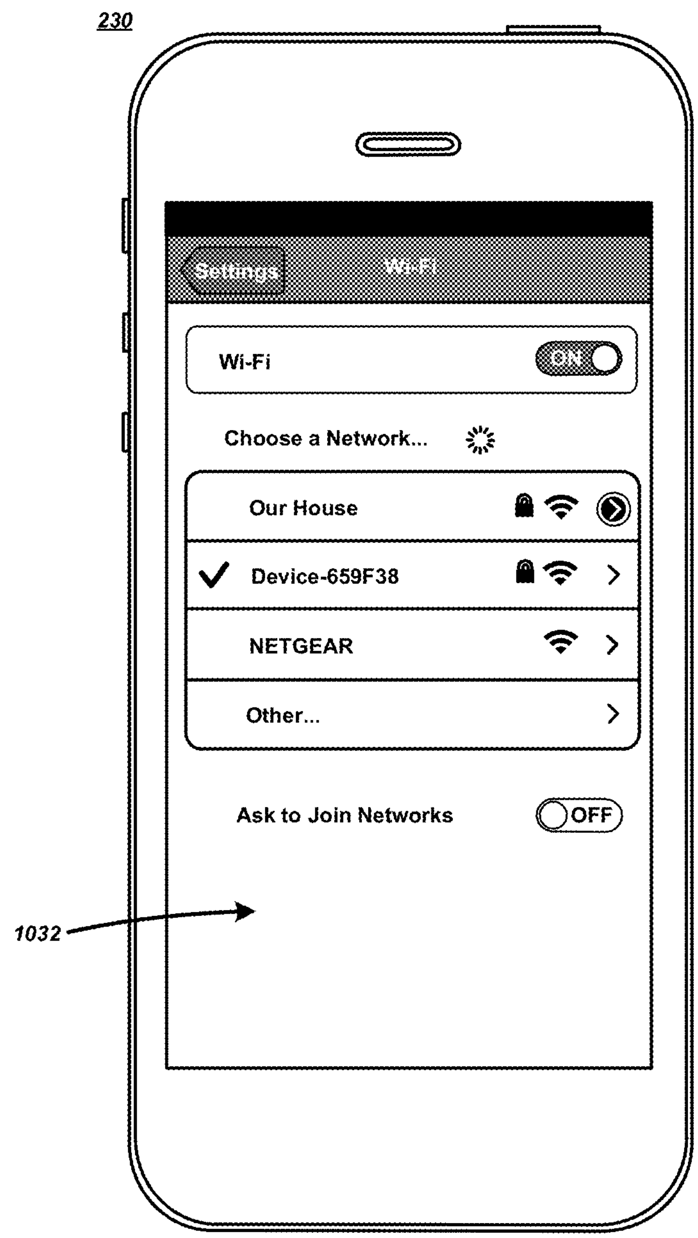
FIG. 18 shows yet another example configuration step of the detector of FIG. 5.
Figure 19:
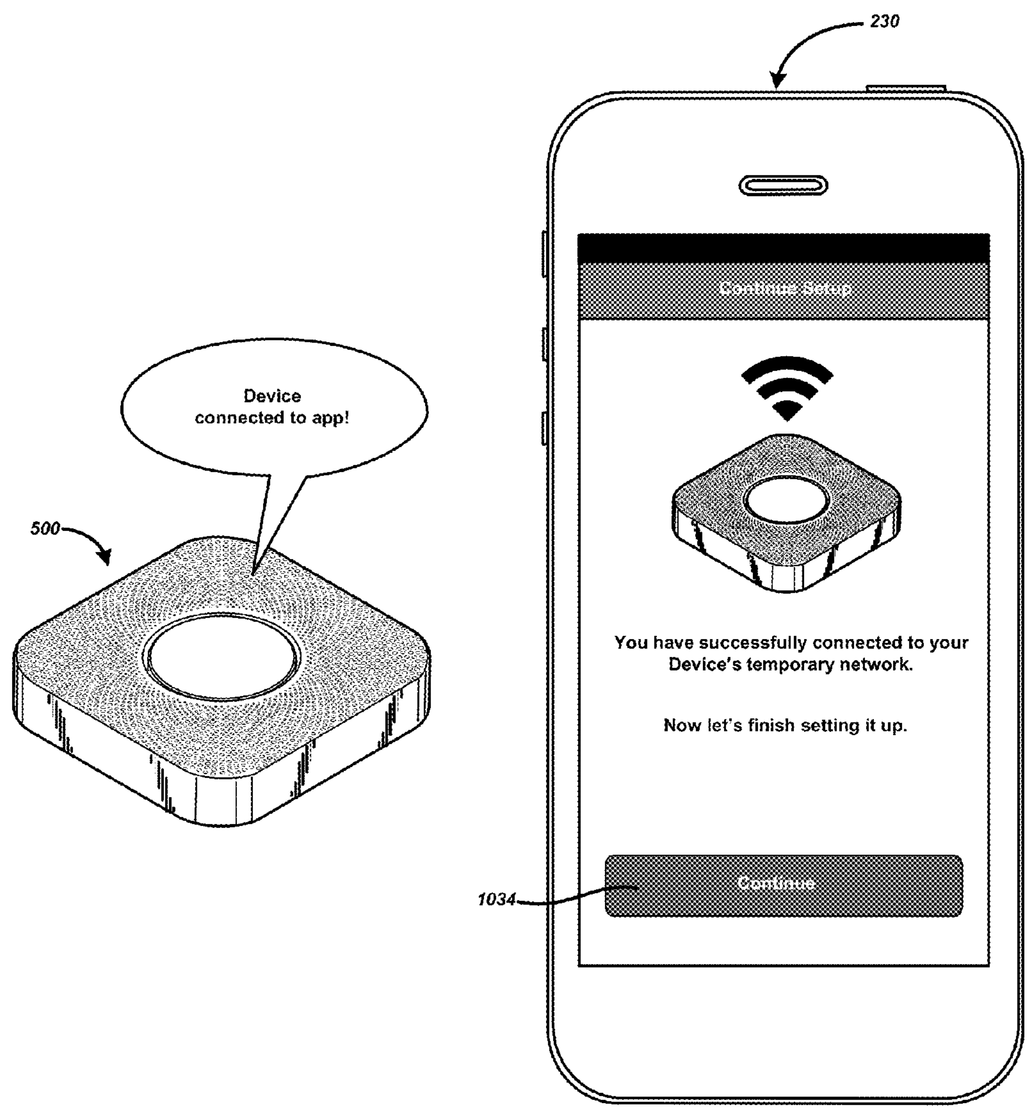
FIG. 19 shows yet another example configuration step of the detector of FIG. 5.

FIG. 18 shows a WiFi configuration interface of a settings application 1032, wherein "Device-659F38" is the selected network. This "Device-659F38" network may have been selected by tapping on "Device-659F38" in the list of detected networks displayed by the settings application 1032. The WiFi configuration interface of the settings application 1032, as shown in FIG. 18, is an example of what the user might see after completing the steps of (1) and (2) of the instructions displayed by application 1012 in FIG. 17. At step (3), the user may return to application 1012 to complete setting up hazard detector 500, whereupon the application 1012 may display the screen shown in FIG. 19. That screen provides confirmation that the mobile device 230 is connected to hazard detector 500. The hazard detector 500 may also generate an audio and/or visual indicator to inform the user that the mobile device 230 and the hazard detector 500 have been successfully connected or paired. For example, as shown in FIG. 19, the hazard detector 500 may generate the following speech: "Device connected to app!" Alternatively, hazard detector 500 may generate other audio and/or visual confirmation of the successful connection. To continue the setup process the user may select a continue button 1034.

Figure 20:
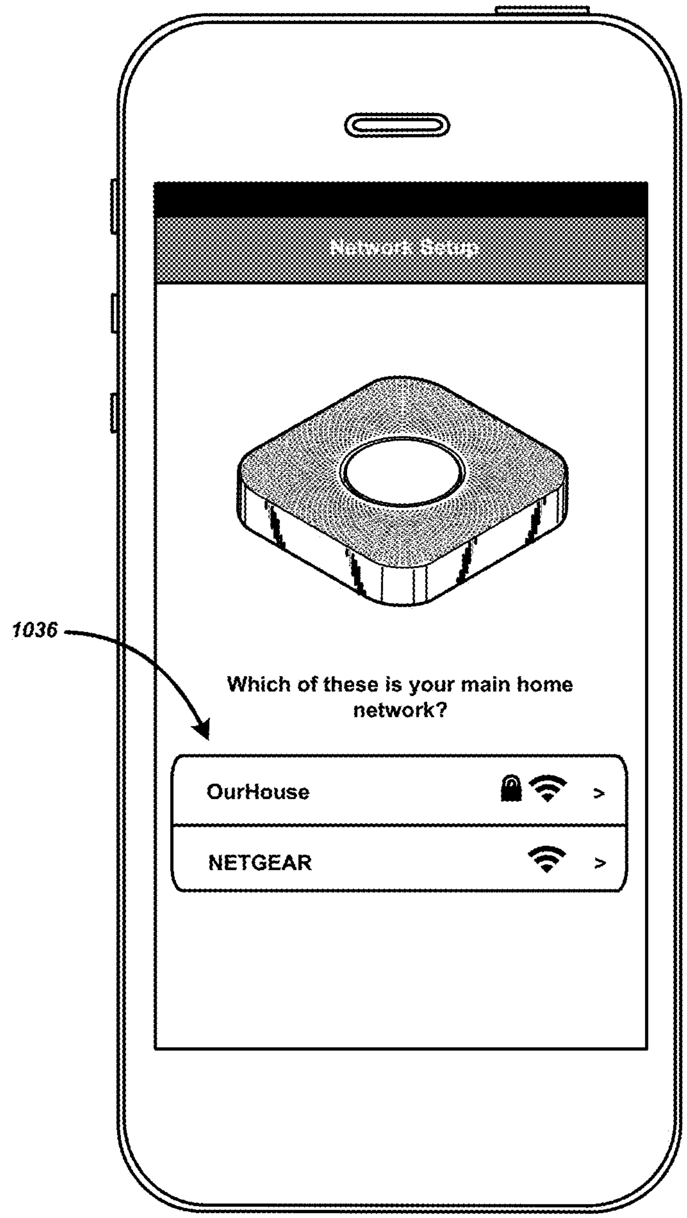
FIG. 20 shows yet another example configuration step of the detector of FIG. 5.
Figure 21:
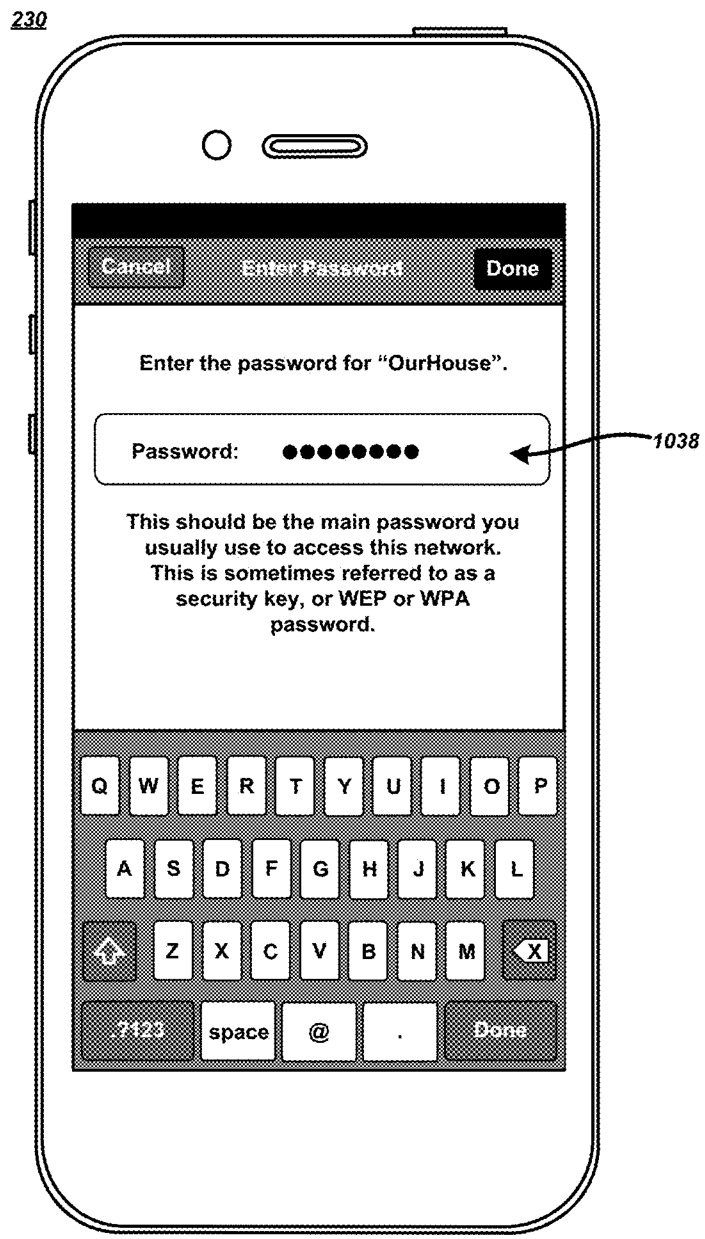
FIG. 21 shows yet another example configuration step of the detector of FIG. 5.

FIG. 20 shows a network setup interface of the application 1012. At this point, the application 1012 may instructs the user to select a main home network from a list 1036 of WiFi networks detected by the mobile device 230, and generated in list form as shown in FIG. 20 by the application 1012. This may allow the user to select a network, e.g., the "OurHouse" network, that the hazard detector 500 may use to connect to the network or network 234. Upon selecting a network, an interface may be displayed by application 1012, as shown in FIG. 21, wherein the user may enter the password for connecting to the selected network in a field 1038. These credentials may be sent by the application 1012 to the hazard detector 500 so that the hazard detector 500 may gain access to the network 234 via a router of the selected network.

Figure 22:
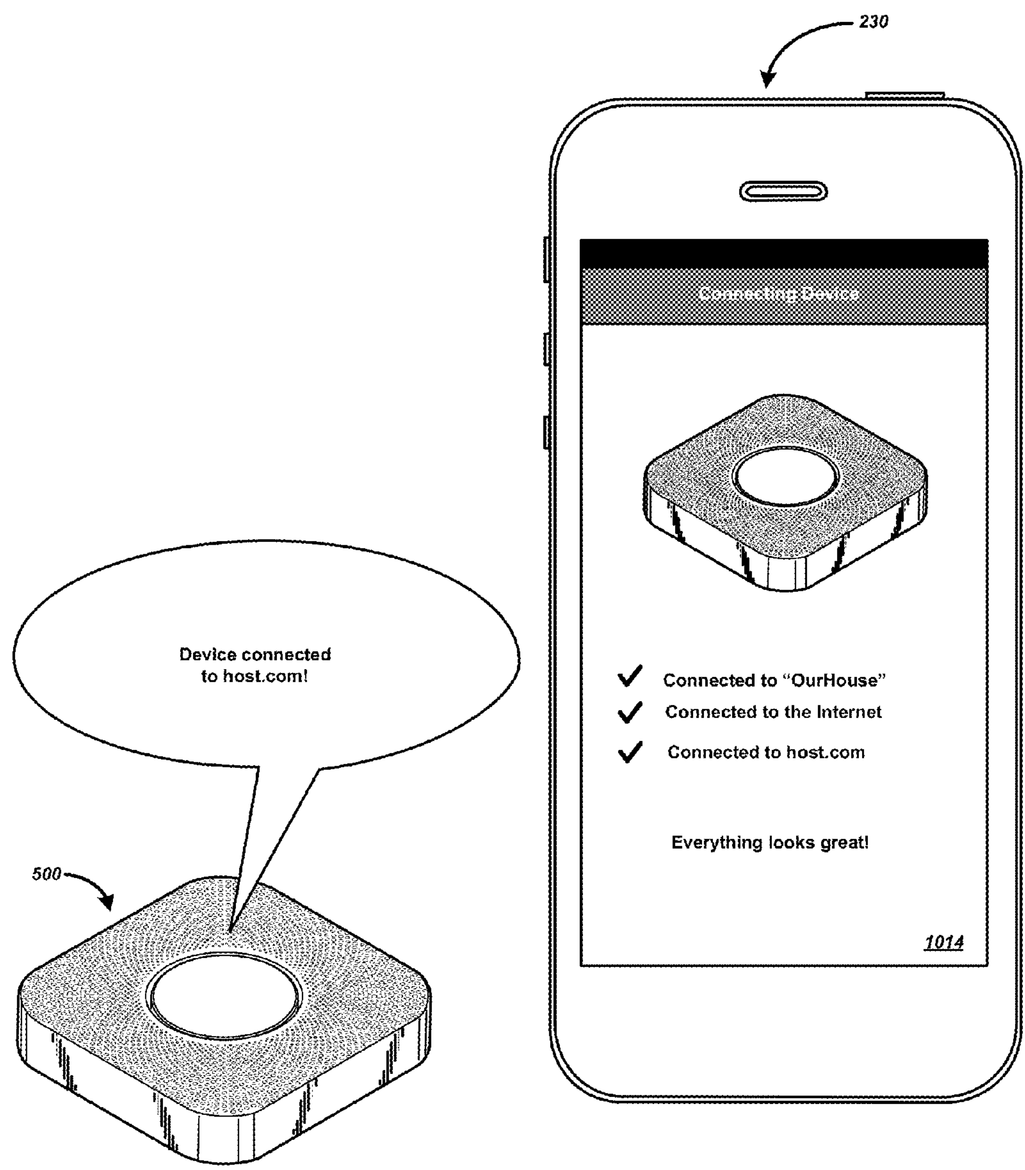
FIG. 22 shows yet another example configuration step of the detector of FIG. 5.

The application 1012 may then display a screen as shown in FIG. 22 in order to provide confirmation that the hazard detector 500 has connected to the "OurHouse" local network, the network 234, and the system 236 via a "host.com" website. The hazard detector 500 may also generate a corresponding audio and/or visual indicator. For example, as shown in FIG. 22, the hazard detector 500 may generate the following audio: "Device connected to nest.com!" Alternatively, the hazard detector 500 may generate other audio and/or visual confirmation of the successful connections. Further, the mobile device 230 itself may generate an audio and/or tactile or vibratory output for confirmation of the successful connections. These confirmations may signify that the hazard detector 500 has been associated with an online management account and the user is able to access or otherwise benefit from the services 306 (see e.g., FIG. 3), e.g., the user may communicate with the hazard detector 500 using a computing device, such as a desktop computer, laptop computer, tablet, or other device, such as the mobile device 230.

Referring now back to FIG. 8, at step 808 of the example method 800, the hazard detector 500 may receive or otherwise detect user-input corresponding to its location within a home or building, such as an end-user inputting information into the mobile device 230 or by manual depression of the lens button 520 that which provides an indication as to where the hazard detector 500 is physically located. In some examples, the hazard detector 500 may transmit the location information to the central server or system 236. As alluded to, the user-input could correspond to location information, such as indication of a room type or room name where hazard detector 500 is currently or instantly being installed. The location information could be stored locally to the hazard detector 500 and/or at the user's online management account, e.g., the system 236, and used to enhance the features of services 306 provided by and to hazard detector 500.

The location information may be used to further configure the hazard detector 500. For example, the location of hazard detector 500 may be used to alter the way alerts and/or alarms are provided and/or how the hazard detector 500 interprets data as acquired by its various sensors. More specifically, for example, the hazard detector 500 may account for the environmental characteristics of a kitchen by adjusting a pre-alarm threshold to make the hazard detector 500 less sensitive to smoke and heat commonly observed in a kitchen environment. Also, for example, the hazard detector 500 may account for increased humidity since higher levels of humidity is a characteristic of a kitchen environment, e.g., higher humidity might develop in the kitchen when water is boiling on the stovetop. Further, for example, the hazard detector 500 may alter an alert or alarm sequence, such as by providing a user more opportunities to preemptively hush an alarm for a known, safe smoke condition. In another example, the hazard detector 500 may be installed in a bedroom. To account for the environmental characteristics of a bedroom, the hazard detector 500 may, automatically based upon a particular algorithm, or manually based upon a particular user-input, become more sensitive to smoke and CO and/or it may increase its alarm volumes for the purpose of waking up sleeping individuals upon detection of a potentially dangerous condition.

Figure 23:
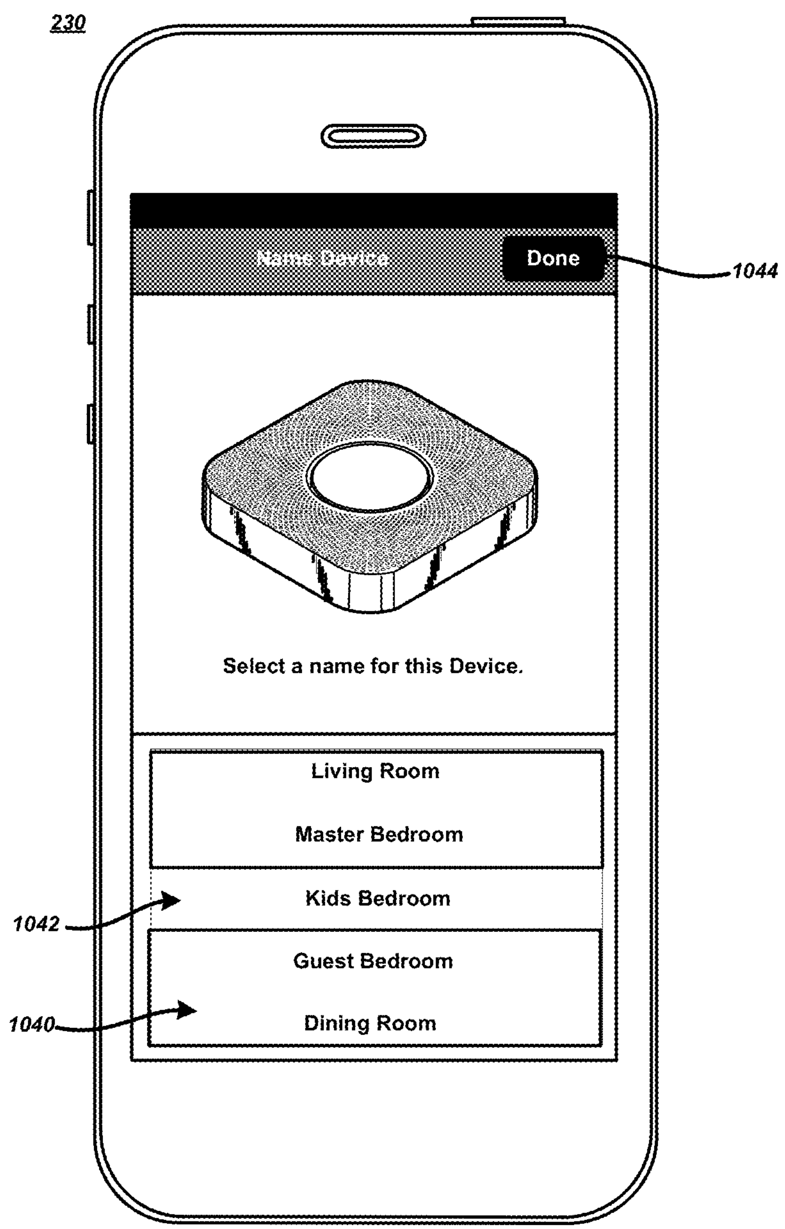
FIG. 23 shows yet another example configuration step of the detector of FIG. 5.

Referring now additionally to FIG. 23, an example of the physical process associated with step 808 is shown in accordance with the principles of the present disclosure. In this example, an interface may be provided by or at the application 1012 on the mobile device 230 to allow or enable a user select a particular installation location for or of the hazard detector 500 by selecting a room type, such as living room, master bedroom, and etc. It is contemplated that the user may perform a slide gesture on a list object 1040 causing the list of room types included on the list object 1040 to scroll up or down, and place one of the room types in a select field 1042. When the desired room type appears in the select field 1042, the user may select a done button 1044 to submit the user-input that indicates the location of the hazard detector 500 within the home. As shown in FIG. 23, the list object 1040 includes the following selectable room types: Living Room, Master Bedroom, Kids Bedroom, Guest Bedroom, and Dining Room. In general though, the list object 1040 may also include different and/or additional selectable room types, e.g., other house rooms, office building rooms, a garage, or mobile home rooms, and so on and so forth. Alternatively, the application 1012 may provide a field, such as the field 1038 as shown in FIG. 21, in which the user can manually enter a room name or room type for the location in which hazard detector 500 is installed or another name for hazard detector 500.

Referring now additionally to FIG. 23, another example of the physical process associated with step 808 is shown in accordance with the principles of the present disclosure. According to this example, the hazard detector 500 may generate audio instructions such as, "Get ready to input a location of the detector." Here, the hazard detector 500 may pause for a moment and then output the audio "Press now for Kitchen." If or when the user presses the lens button 520 soon after hearing the "Press now for Kitchen" instruction, then the hazard detector 500 may set its location to "Kitchen." If, however, the user does not press the lens button 520, the hazard detector 500 may output audio, "Press now for Bedroom." If the user presses the lens button 520 soon after hearing the "Press now for Bedroom" instruction, the hazard detector 500 may set its location to "Bedroom." It is contemplated that this process may continue until the user selects a particular location for installation of the hazard detector 500. Such audible commands are provided for illustrative purposes, and there is an unlimited number of words and word combinations that may be used to communicate the same or different instructions.

Figure 25:
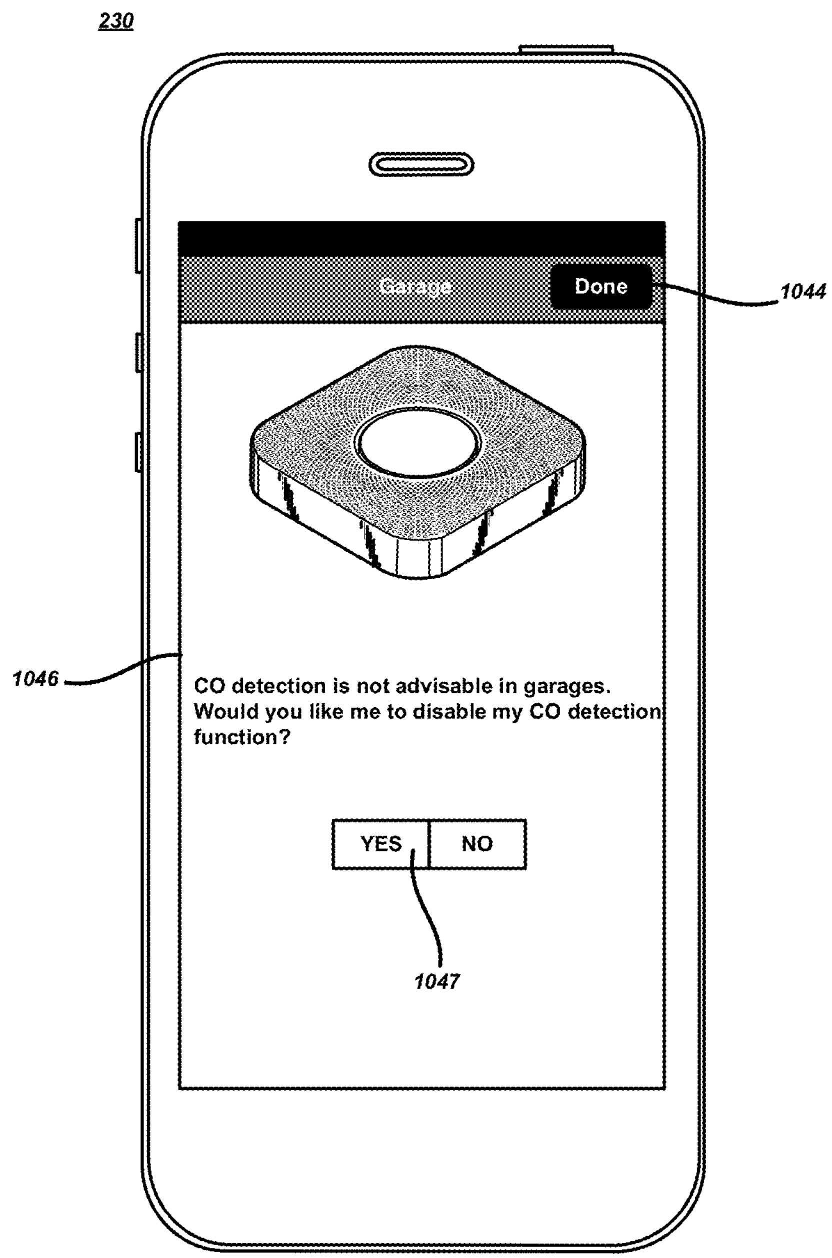
FIG. 25 shows yet another example configuration step of the detector of FIG. 5.

Referring now back to FIG. 8, at step 810 of example method 800, a user may be advised of recommended settings for the hazard detector 500 based upon the identified location of the hazard detector 500. Some features of hazard detector 500 may not be desirable for some locations and, when installed in those locations, the hazard detector 500 can be placed in a limited operation mode in which one or more of those features are disabled. For example, it is contemplated that garages are inadvisable locations in which to place a CO detector. However, it is further contemplated that garages are advisable locations in which to place heat detectors. Accordingly, and referring now additionally to FIG. 25, if a user inputs "Garage" as the location at step 808, then according to step 810, the application 1012 may provide the user with a message 1046, informing the user that CO detection is not advisable in garages and giving the user the option of turning Off the CO detection function via a control element 1047.

Figure 26:
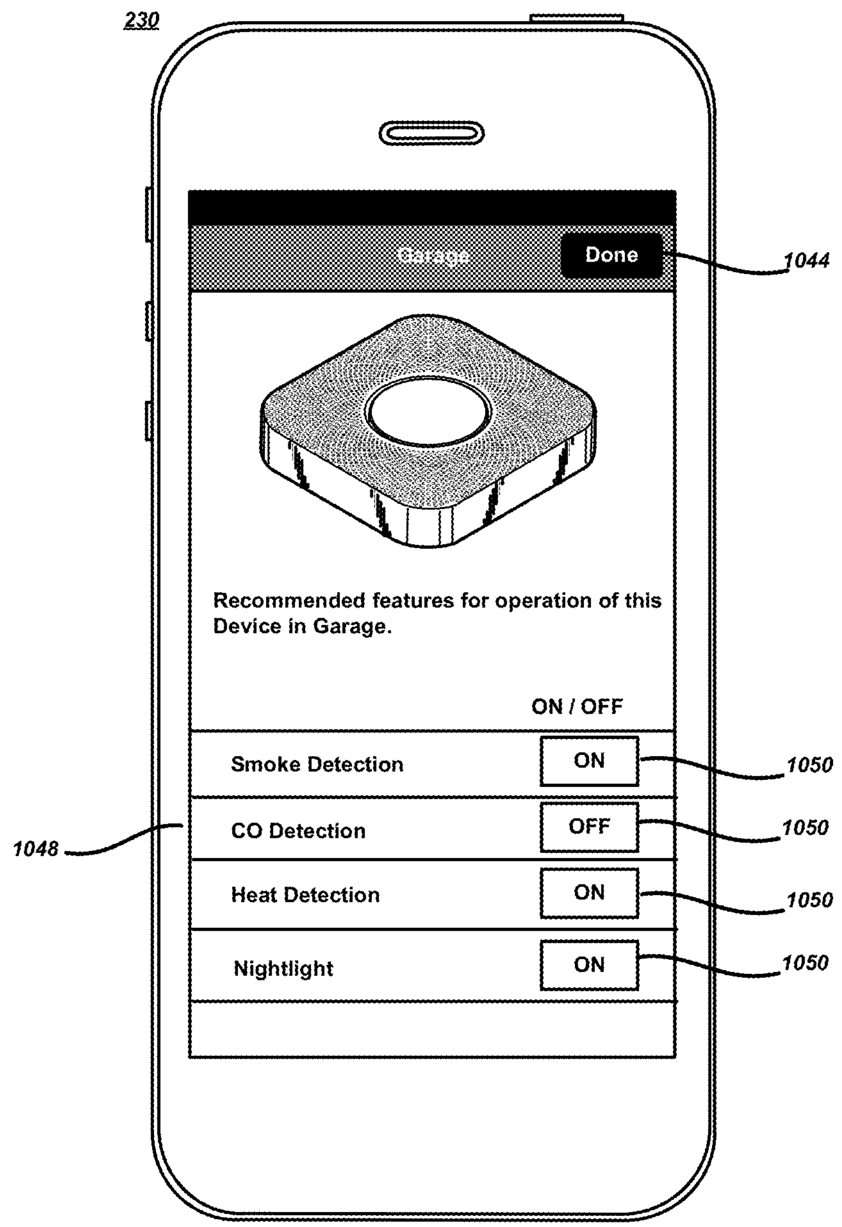
FIG. 26 shows yet another example configuration step of the detector of FIG. 5.

FIG. 26 illustrates another example of the application 1012 providing recommended settings for the hazard detector 500 based upon the identified location of the hazard detector 500. Here, the application 1012 provides a list 1048 of recommended settings for the location of the hazard detector 500. As illustrated, the application 1012 may recommend turning on the smoke detection, heat detection, and nightlight functions, but disabling the CO detection since the hazard detector 500 in this scenario is intended to be installed in a Garage. The user may accept these recommended setting by pressing done button 1044, or the user may change the recommended settings by pressing a particular instance of a control or button 1050 next to each of the listed settings to toggle between OFF and ON, and then press the button 1050 when the settings are to the user's liking.

Figure 27:
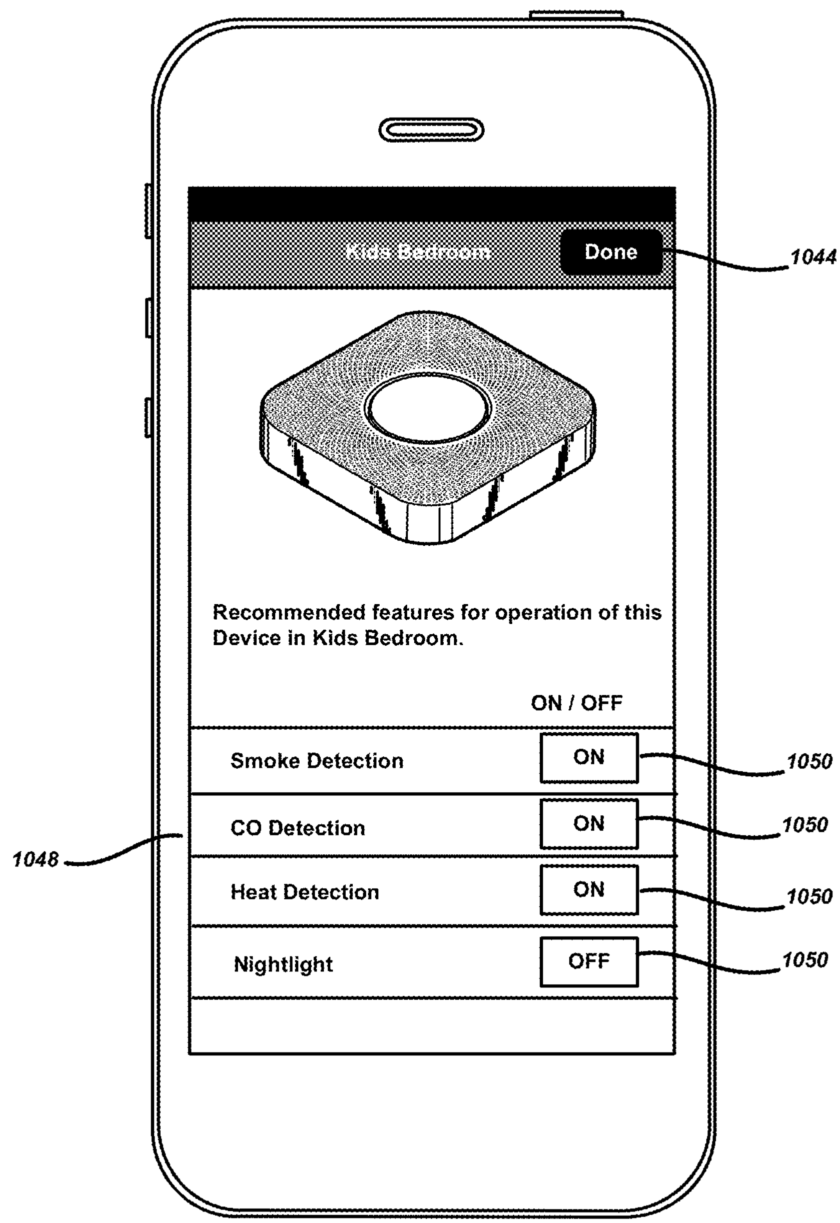
FIG. 27 shows yet another example configuration step of the detector of FIG. 5.

FIG. 27 illustrates yet another example of the application 1012 providing recommended settings for the hazard detector 500 based upon the identified location of the hazard detector 500. In this example, the hazard detector 500 is being installed in a "Kid's Bedroom" when the default setting for the nightlight function is OFF, and ON is the default setting for smoke detection, CO detection, and heat detection. The nightlight is set to OFF so that the light will not disturb people or the child while sleeping. However, for other rooms, such as living rooms and kitchens, the default setting for the nightlight function might be ON.

Referring now back to FIG. 8, at step 812 of the example method 800, responsive to being advised of recommended settings for the hazard detector 500 based on the location of the hazard detector 500, the user may input their selections of which features to turn ON and OFF. As discussed above in connection with FIG. 25, responsive to being advised that CO detection is not recommended in Garages, the user can may press the control element 1047 to answer Yes or No to the question of whether to turn OFF the CO detection function. After selecting Yes or No the user may press the button 1044 to submit the selection. As discussed above in connection with FIGS. 26-27, responsive to being presented with the a list 1048 of recommended functions for a location, a user may press a particular button 1050 to select which features the user wants turned OFF or ON. The user may then press the button 1044 to input the selections.

At step 814 of the example method 800, a test may performed to ensure that the hazard detector 500 is not being or is installed in a bad or non-preferable or non-optimal location, such as where one or more of its sensors are obstructed. In this example, it is contemplated that the hazard detector 500 may execute a self-test where it leverages its ultrasonic sensor(s) to determine its position relative to walls, ceilings, floors, and/or other objects located in the room. For example, the hazard detector 500 may use its ultrasound sensor(s) to "see" if the hazard detector 500 is located too deep in a corner or behind an obstruction, where it does not have unobstructed access to monitor the conditions of a room, including detecting occupancy of the room. In one example, the hazard detector 500 may test to determine whether it is too far in a corner by using its ultrasound sensor to detect whether the perpendicular walls are within a predetermined distance, such as five feet or a couple of meters for example.

Figure 28:
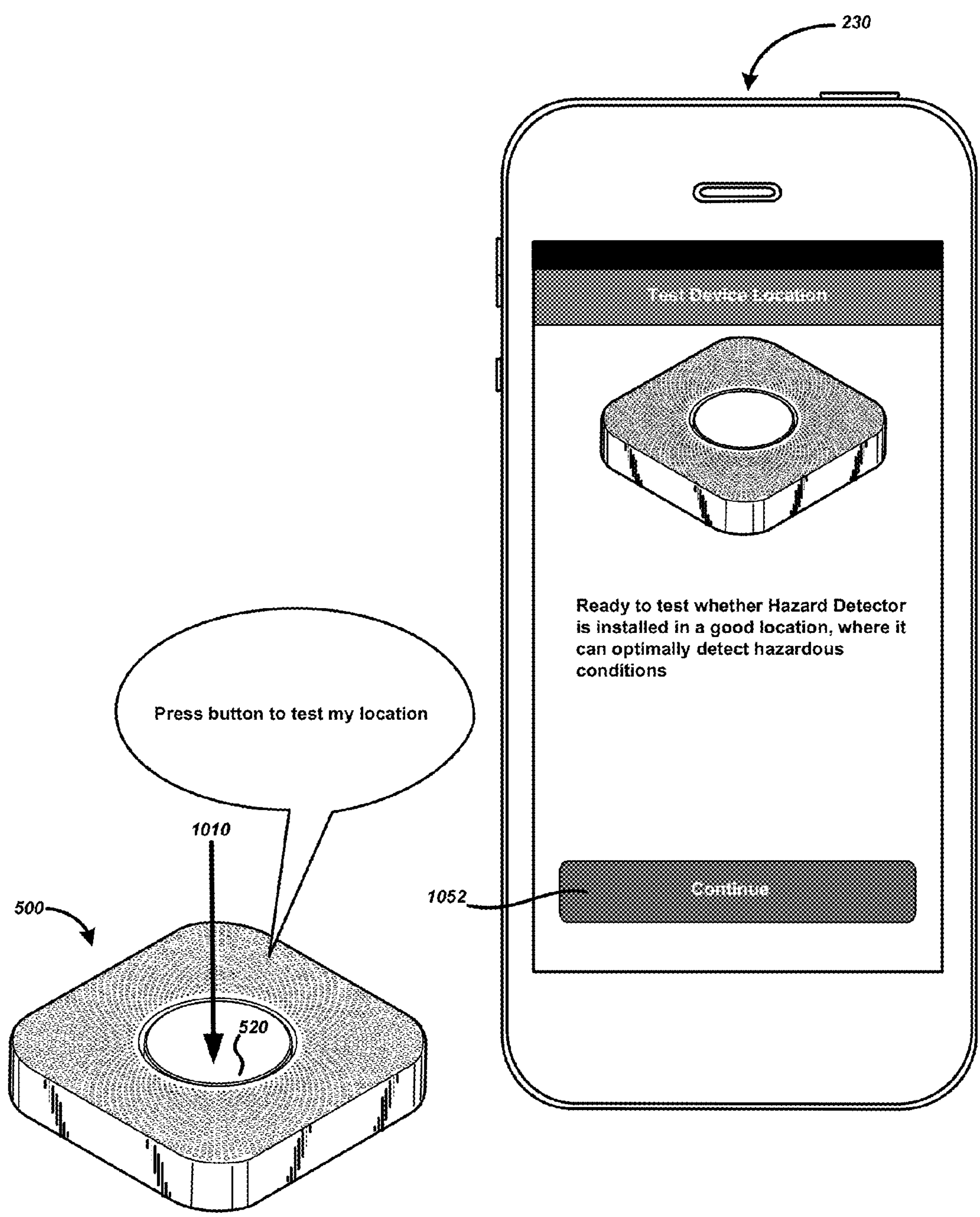
FIG. 28 shows yet another example configuration step of the detector of FIG. 5.

Referring now additionally to FIG. 28, an example of a physical process associated with step 814 is shown in accordance with the principles of the present disclosure. In this example, an interface may be provided at or by the application 1012 on mobile device 230 to explain that the hazard detector 500 is ready to test whether it is installed in a good location, where it can optimally detect hazardous conditions. Here, it is contemplated that the user may press the button 1052 to begin the test. Also, as illustrated in FIG. 28, the hazard detector 500 can output an audible message, "Press button to test my location." In response, a particular individual users may press the lens button 520 in the direction 1010 to begin the test. If the test fails due to hazard detector 500 being position too close to an object for example, such as a wall, the application 1012 may display message, and/or hazard detector 500 may output an audio and/or visual cue or message, indicating that hazard detector 500 may be too close to an object, such as a wall, and also recommend relocation of the hazard detector 500 to another position or location for installation.

Figure 29:
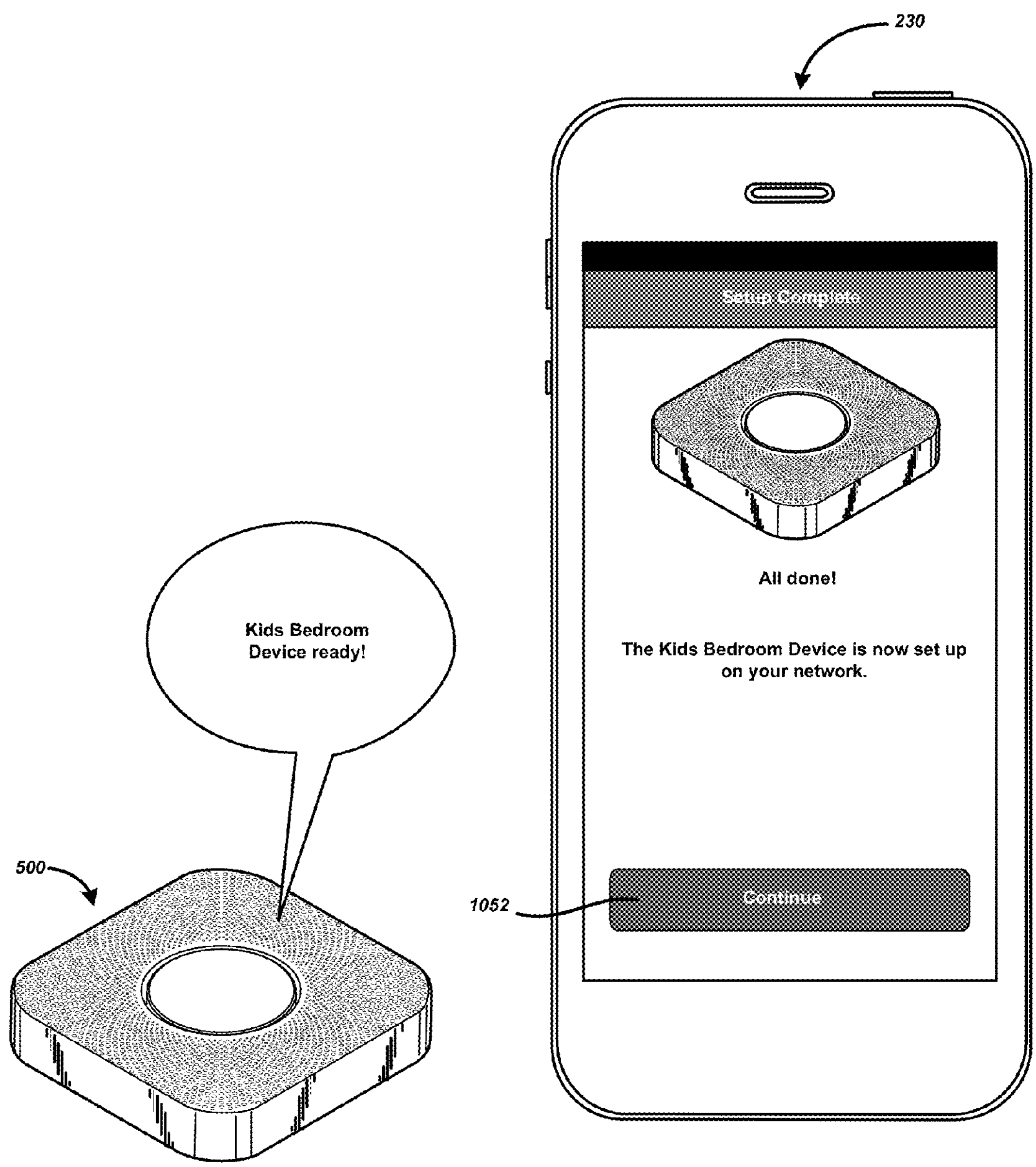
FIG. 29 shows yet another example configuration step of the detector of FIG. 5.

Referring now back to FIG. 8, at step 816 of the example method 800, the system 236 (see FIG. 2) may confirm setup and pairing of the hazard detector 500. For example, at step 816, the application 1012 may provide one or both of an audio and visual cue or confirmation message that confirms the pairing association created at step 804, and the setup selections made at steps 808 and 812, were or was successful. Referring now additionally to FIG. 29, an example of a physical process associated with step 816 is shown in accordance with the principles of the present disclosure. Here, the application 1012 may display or output a screen in order to provide confirmation that the setup for the hazard detector 500 is complete. The hazard detector 500 may also generate a corresponding audio and/or visual indicator. For example, as shown in FIG. 29, the hazard detector 500 may generate the following output when the "Kids Bedroom" is the location selected at step 808: "Kids Bedroom Device Ready." Alternatively, the hazard detector 500 may generate other audio and/or visual confirmation of the successful association. These confirmations may signify that hazard detector 500 has been associated with the selected location at the online management account on the system 236. The user may then tap the continue button 1052 to confirm that the confirmation screen has been viewed. Although additional steps may not be required in order to complete the setup of hazard detector 500, the user may still proceed with additional steps to verify that the hazard detector 500 is functioning properly.

In some examples, the input provided at the application 1012 as discussed in the context of the example method 800 may be accomplished using speech recognition, air gestures, eye tracking and blink detection and/or other input means. Again, as mentioned above, the method 800 may also occur at a webpage as accessed via or by a personal computer or any other computing device. Furthermore, although the communication between hazard detector 500 and the mobile device 230 is described above as occurring over WiFi, other wireless protocols supported by both the hazard detector 500 and the mobile device 230. Also, while a limited number of visual and audio indicators generated by hazard detector 500 were described above, other indicators may also be generated by hazard detector 500 during the example method 800.

According to the principles of the present disclosure, "alarm condition detection and notification" services are provided to detect and warn users of alarm conditions in an environment, such as a home. More particularly, the hazard detector 500 for example may detect alarm conditions based on information obtained from its sensors, and provide corresponding alarms to perceivable to users or customers. In general, alarm conditions may for example be divided into two categories: pre-hazardous conditions and serious hazardous conditions. Serious hazardous conditions may comprise situations where sensor data indicates that conditions in an environment are dangerous to the health and safety of individuals in the environment. Pre-hazardous conditions may however comprise situations where the sensor data is not "strong" enough to support a serious hazardous condition, but the sensor data is enough to suggest that a pre-hazardous condition may exist in the environment, and that it may be beneficial to notify users so they can investigate the condition and assess whether remedial measures are warranted to prevent the pre-hazardous condition from escalating to a serious hazardous condition.

As mentioned, the hazard detector 500 may provide an alarm to users upon determining that an alarm condition exists in an environment. In a smoke-related example, the hazard detector 500 may provide an alarm for smoke indicating an alarm condition for smoke exists in the environment. In one example, the hazard detector 500 may determine that an alarm condition for smoke exists when, based on data obtained from its sensors, it observes that conditions in the environment have reached or exceeded one or more predetermined thresholds, including one or more of a smoke threshold, a humidity threshold, a CO threshold, and a temperature threshold. In a particular example, the hazard detector 500 may determine that an alarm condition for smoke exists when the smoke level in the environment exceeds a threshold trend for smoke, such as 0.5 obscuration for thirty consecutive seconds for example. In another smoke-related example, the hazard detector 500 may determine that an alarm condition for smoke exists when the smoke level in the environment exceeds a threshold trend for smoke and the humidity level of the environment is decreasing. In other examples, the hazard detector 500 may determine that an alarm condition for smoke exists when the CO level of the environment exceeds a threshold value for CO, such as CO>70 instantaneously for example, or when the temperature of the environment exceeds a threshold trend for temperature, such as, temperature of environment increases by 10° F. in last three minutes for example.

In a CO-related example, the hazard detector 500 may provide an alarm indicating an alarm condition for CO exists in the environment. In this example, the hazard detector 500 may determine that an alarm condition for CO exists when, based on data from its sensors, it observes that conditions in the environment have reached or exceeded one or more predetermined thresholds used to determine whether an alarm condition for CO exists. In one example, the hazard detector 500 may determine that an alarm condition for CO exists and then provide a corresponding alarm when its CO sensor observes CO levels above a threshold trend for CO, such as CO concentration exceeds 50 ppm for thirty consecutive seconds, or CO concentration exceeds 300 ppm after a three-minute period, etc. In some example, a power law function, such as a quadratic function may be used to model the threshold trend for CO. In an example quadratic function, time is the independent variable and CO level is the dependent variable. If, at a particular time, the CO level of the environment exceeds the CO level provided by the quadratic function for that particular time, then the hazard detector 500 may determine that an alarm condition for CO exists. Other examples are possible.

In a heat-related example, the hazard detector 500 may provide a pre-alarm indicating a pre-hazardous condition for heat that exists in the environment. In this example, the hazard detector 500 may determine that a pre-alarm condition for heat exists when, based on data from its sensors, it observes that conditions in the environment have reached or exceeded one or more predetermined thresholds used to determine whether a pre-hazardous condition for heat exists. In one example, the hazard detector 500 may determine that a pre-hazardous condition for heat exists and provides a corresponding pre-alarm when its heat sensor observes heat levels above a threshold value for heat, such as when heat exceeds 90° F. In another example, the hazard detector 500 may determine that a pre-hazardous condition for heat exists and then may provide a corresponding pre-alarm when its heat sensor observes heat levels above a threshold trend for heat, such as temperature that has increased by at least 12° F. over sixty seconds.

In yet another example, the hazard detector 500 may determine that a pre-hazardous condition for heat exists and may then provide a corresponding pre-alarm when its heat sensor observes heat levels above a threshold value and a threshold trend for heat, such as temperature that exceeds 90° F. and the temperature has increased by at least 12° F. over sixty seconds. It should be appreciated that a linear function, such as a piecewise linear function, may be used to model the threshold trend for heat. In an example linear function, time is the independent variable and temperature is the dependent variable. If, at a particular time, the temperature of the environment exceeds the temperature provided by the linear function for that particular time, then the hazard detector 500 may determine that a pre-hazardous condition for heat exists.

As discussed throughout, the hazard detector 500 of the present disclosure may provide a pre-alarming or pre-alarm capability, which may also be referred to as a "heads-up" capability, to provide a warning to a user that a pre-hazardous condition has been detected in which there are elevated readings corresponding to a type of hazard(s) being detected, but those readings do not yet rise to levels corresponding to an actual or serious alarm condition. Examples of pre-alarm or heads-up conditions may include, but not limited to, readings for carbon monoxide that are elevated but not high enough to warrant the sounding of a standard emergency carbon monoxide alarm, or readings for smoke levels that are elevated but not high enough to warrant a sounding of a standard emergency smoke alarm.

When a heads-up condition is detected, the hazard detector 500 may sound or output an audible, but not ear-piercing, "pre-alarm" or "heads-up" message that audibly informs those within earshot of the pre-alarm condition. In some examples, a modulated light glow of a concerning color, such as red or yellow, and/or spatiotemporal light pattern output via the light ring 522 of the hazard detector 500 may accompany the audio pre-alarm message. One example of such an audible message that may be provided in the context of a pre-alarm level of smoke for a hazard detector installed in a bedroom may comprise a bell or bell-like sound, followed by an voice message, "Heads-up. There is smoke in the bedroom." In some examples, once the pre-alarm condition has gone away or subsided, such as when for example an individual user has gone to the bedroom and snuffed out a cigarette that was in the ash tray, and that action was successful in clearing up the smoke, the hazard detector 500 may then audibly advise that the pre-alarm condition has cleared, such as "Smoke has cleared in or from the bedroom." In the event the pre-alarm condition escalates into an actual or serious alarm condition, then an ear-piercing alarm my sound, possibly accompanied by an emergency-indicating halo glow output via the light ring 522, such as a flashing red light, also accompanied by, during any regulation-required or regulation-permitted silence intervals between alarming, a voice or audio alarm such as "EMERGENCY. THERE IS SMOKE IN THE BEDROOM, GET OUT NOW." Other examples are possible.

According to some examples, users may "hush" the hazard detector 500 to cause it to stop "pre-alarming" and to continue monitoring the environment. While the hazard detector 500 is "hushed" or quieted, users may investigate whether the indicated pre-hazardous condition indeed exists and take any necessary remedial measures. However, if the pre-hazardous condition persists, the hazard detector 500 may provide another pre-alarm indicating that the pre-hazardous condition still exists. Further, the hazard detector 500 may provide a "regular" or "emergency" or "serious hazardous alarm" indicating a serious hazardous condition exists if the pre-hazardous condition escalates to a serious hazardous condition. In some examples, the thresholds that the hazard detector 500 uses when determining whether a serious hazardous condition exists are set to or at least based on UL Standards for Safety. In general, those thresholds may not be adjusted or modified in a manner similar to of the "pre-alarm" or "heads-up" thresholds as discussed throughout. The present disclosure though is not so limited. For instance, in some examples the thresholds that the hazard detector 500 uses when determining whether a serious hazardous condition exists, those set to or at least based on UL Standards for Safety, may be adjusted or modified in a manner similar to of the "pre-alarm" or "heads-up" thresholds as discussed throughout, possibly based upon implementation-specific details.

According to examples, the pre-alarms indicating pre-hazardous conditions provide details about the pre-hazardous condition. For example, the hazard detector 500 and/or the system 236 may send a message to the mobile device 230 of user stating specifics about the condition. In one particular example, the message may comprise "The CO level in your home has increased twenty-percent in the last two weeks. You might consider having an expert inspect your home to determine the cause." Also for example, the hazard detector 500 and/or other smart devices in the home may make similar audible announcements or display similar written messages, such as for example via user-interface or projection onto a wall or ceiling.

According to examples, thresholds such as smoke thresholds, CO thresholds, heat thresholds, etc., used by the hazard detector 500 to determine whether a pre-alarm condition exists are adjusted or set based at least in part on where the hazard detector 500 is located. For example, the thresholds used by a particular hazard detector 500 located in a kitchen to detect pre-alarm conditions in the kitchen may be different than the thresholds used to by a particular hazard detector 500 located in a bedroom to detect pre-alarm conditions in the bedroom. For example, thresholds used by the hazard detector 500 located in the kitchen may account for smoke levels common to kitchens, thereby making the hazard detector 500 less sensitive to smoke resulting from normal cooking activities that occur in kitchens and less likely to cause an undesired pre-alarm. Reducing undesired pre-alarms is one notable advantage provided by adjusting or setting thresholds based on where the hazard detector 500 is located.

Figure 30:
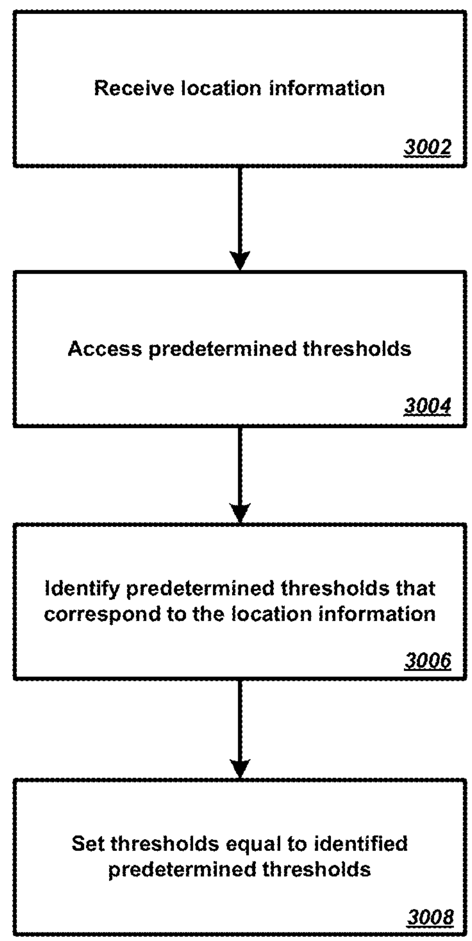
FIG. 30 shows a third example method according to the disclosure.

Referring now to FIG. 30, an example method 3000 of setting one or more thresholds used by a hazard detector to determine whether an pre-alarm condition exists. In this example, the thresholds are set based the location of a particular hazard detector 500 within a home or residence. As indicated at step 3002, the example method 3000 generally begins with the hazard detector 500 receiving location information. In one example, the location information may be provided by an individual during the process of installing the hazard detector 500. For example, a user may provide the hazard detector 500 with user-input that indicates the location of the hazard detector 500 within the home or residence. For example, the user-input may indicate the name or type of the room or area, such as bedroom, kitchen, garage, etc., where the hazard detector 500 is located.

Figure 24:
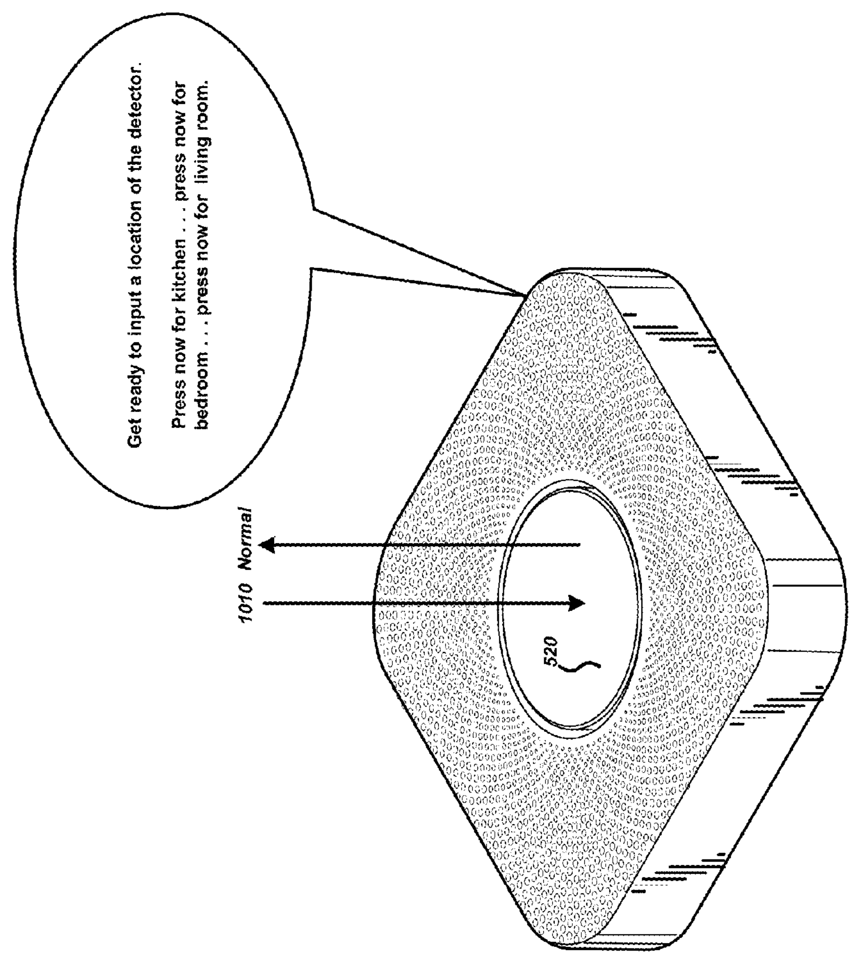
FIG. 24 shows yet another example configuration step of the detector of FIG. 5.

Examples of the hazard detector 500 receiving such user-input that indicates the location of the hazard detector 500 are illustrated in FIGS. 23-24. For example, the application 1012, which is running on the mobile device 230, may provide a user interface that allows a user to input a location for the hazard detector 500. To do so, the user may interact with the list object 1040 causing the list of room types included on the list object 1040 to scroll up or down and place one of the room types in the select field 1042. When the desired room type appears in select field 1042, the user may select the done button 1044 to submit the user-input that indicates the location of the hazard detector within the home, and the mobile device 230 may then transmit the information to hazard detector 500.

At step 3004, predetermined thresholds that correspond to the location of the hazard detector 500 may be accessed. In this example, data may be provided that includes predetermined thresholds that the hazard detector 500 may uses to set detection thresholds or threshold values, which it uses to determine whether pre-alarm conditions for smoke, CO, and heat, among others, exist in the location where it is installed. The predetermined thresholds vary based on location. For example, thresholds for determining that an pre-alarm condition for smoke exists in a nursery may be set to be substantially more sensitive less than the thresholds for determining that a pre-alarm condition for smoke exists in the kitchen. This is consistent with the fact that a parent will likely want to have a heads-up alert even for a little bit of smoke in the nursery whereas they will not want to be bothered by a pre-alarm in the kitchen unless there is substantially more smoke, because some degree of smoke is to be expected in the kitchen.

In some examples, data having predetermined thresholds and corresponding locations is stored locally on the hazard detector 500. For example, the data may be a lookup table stored in memory on the hazard detector 500. Thus, to access predetermined thresholds, according to step 3004 of the example method 3000, the hazard detector 500 may access the lookup table stored in local memory. In other examples, this data may be stored to or on a remote server, such as the system 236. According to these examples, the hazard detector 500 may obtain a pre-alarm threshold by receiving the same from a server via a network communication. For example, the hazard detector 500 may transmit, via a network connection, to a server such as the system 236 for example, a query message that includes the room type inputted by the user. Upon receiving the message, the server may access data having room types and corresponding pre-alarm thresholds to identify the pre-alarm alarm thresholds that correspond to the room type. The server may then populate the identified pre-alarm thresholds in a response message and send that message back to the hazard detector 500. Here, the hazard detector may receive, via the network connection, from the server the response message that includes the pre-alarm threshold that corresponds to the room type. Upon accessing data having predetermined thresholds and corresponding locations according to step 3004, the example method 3000 may proceed to step 3006 for identifying in the accessed data the predetermined thresholds that correspond to the location information.

Referring still to FIG. 30, the method 3000 may then proceed to step 3008 for setting the thresholds of the hazard detector 500 to be equal to the identified predetermined thresholds that correspond to the location of hazard detector 500. According to examples, the hazard detector 500 may set respective thresholds it uses to detect pre-alarm conditions for smoke, CO, and heat equal to the corresponding predetermined thresholds identified according to step 3006. According to further examples, the hazard detector 500 may automatically create a dynamically adjustable pre-alarm based on historical CO data to detect a pre-alarm condition involving CO in a garage, even if the hazard detector 500 is not located in the garage. CO detectors are typically not recommended for garages because of the high frequency of false alarms due to the high levels of CO produced by cars. However, it is contemplated that it may be beneficial to provide CO detection for garages.

To provide said CO-detection for garages, the hazard detector 500 may record a historical log of CO data that it has detected. This log may be stored locally on the hazard detector 500 itself, or it may be stored at the system 236. A processor of the hazard detector 500 or of the system 236 may apply one or more algorithms against the log of CO data to determine whether the data indicates that one or more automobiles are regularly started nearby. For example, the algorithms may detect occasional CO spikes that quickly dissipate and, based on the amount by which the CO level increases and the amount of time it takes for the detected CO to dissipate, and the hazard detector 500 or system 236 may infer that the spike was caused by a car that was started and then driven away. If, after making this inference that a car is regularly started and driven away, the hazard detector 500 may observe an incident where the CO spikes but does not dissipate according to schedule or known profile. Then, the hazard detector 500 may determine that a pre-hazard condition for CO exists, even if the increase CO levels are not high enough to warrant a serious hazardous condition, or even a pre-hazardous condition under usual circumstances.

Referring now back to FIG. 1, as discussed above in connection with the same, FIG. 1 illustrates an example implementation of a particular smart hazard detector, such as the hazard detector 500, that may itself function as a guide during a process of installation of the same at an installation location, and that the installation location of the particular smart hazard detector may play a central role in how various settings of the smart hazard detector are defined and adjusted over time. In particular at step 102, an input may be provided or supplied to a particular smart hazard detector, or a device or system communicatively coupled to or with the smart hazard detector for example, that identifies an installation location within a residence of the smart hazard detector. An example of an installation location may include “Hallway” or “Living Room” or “Garage” of or within a particular residence for instance.

Such a feature or step may in some examples enable a method for configuring a hazard detector having a plurality of features and a default configuration profile that specifies predetermined ones of the plurality of features as enabled or disabled. An example default configuration profile is shown and discussed below in connection with a Table 1, and the subject example method may include or comprise a step 102*a*, i.e., a sub-step of step 102 of FIG. 1 for example, of providing an opportunity for a user to input a designated location for installation of the hazard detector within a residence, in a manner similar to that as discussed throughout.

The method may additionally, or alternatively, include or comprise a step 104*a*, i.e., a sub-step of step 104 of FIG. 1 for example, of identifying at least one feature of the plurality of features to enable or disable based upon the designated location, in response to receiving the designated location, and a step 104*b* of instantiating a command to enable or disable the at least one feature of the plurality of features of the hazard detector, in response to identifying the at least one feature. The phrase “in response to” may in some examples discussed throughout refer to or otherwise designate a step(s) and/or feature(s) of the present disclosure implemented and/or performed automatically, or as part of an automated process, by a computer system or device, such as the hazard detector 500 without explicit, manual user input. Other examples are possible.

Further, as an example, the mentioned plurality of features may include a smoke detection feature and a carbon monoxide detection feature, and the mentioned default configuration profile may include an indication and/or specify both of the smoke detection feature and carbon monoxide detection feature as enabled or activated or placed in an ON or a ready state, etc., where the carbon monoxide detection feature may be disabled by the hazard detector when the mentioned designated location is of a predetermined type of location for which carbon monoxide detection is inadvisable or not recommended or the like. An example of such a type of location may include a garage type of location. Advantageously, when the hazard detector is installed to such a particular type of location, the carbon monoxide detection feature may be disabled or deactivated or placed in an OFF or a standby state, etc., so as to prevent or at least minimize the instantiation of an alarm, such as a “heads-up pre-alarm” for example, due to carbon monoxide levels resultant from the starting/running (e.g., at least temporarily) of a vehicle in a garage for example. In general, a user may be advised that it is recommended to disable the carbon monoxide detection feature of a hazard detector installed in a garage for this and possibly other reasons. Other examples are possible.

The method may additionally, or alternatively, include or comprise a step 104*c* of accessing information pre-stored in a memory of the hazard detector to identify the at least one feature to enable or disable based upon the designated location. Additionally, or alternatively, the method may include or comprise a step 104*d* of accessing information pre-stored in a database remote from the hazard detector to identify the at least one feature to enable or disable based upon the designated location. Advantageously, such an implementation may enable the hazard detector to, when a network connection is available for example, negotiate with a remote server system to identify the at least one feature to enable or disable based upon the designated location. Such information as stored and/or maintained at or by the remote server system may periodically or at least intermittently be refreshed or updated so that in turn the hazard detector may be supplied the most current and up-to-date information as to recommended features to enable/disable, based upon the designated location. In this example, the information pre-stored in the memory of the hazard detector may then too be periodically or at least intermittently be refreshed or updated so that in instances when a network connection is not instantly or currently available. Accordingly, such information as stored and/or maintained at or by the hazard detector may periodically or at least intermittently be refreshed or updated so that in turn the hazard detector may have the most current and up-to-date information as to recommended features to enable/disable. Other examples are possible.

The method may additionally, or alternatively, include or comprise a step 104*e* of providing an opportunity for the user to override a particular setting in the default configuration profile so that an associated feature of the plurality of features is switched between enabled and disabled. In general, with reference to Table 1 below, that which is discussed in further detail below, a user may interact with their smartphone for instance to navigate a website or a mobile application for example to selectively enable/disable particular features of the hazard detector. FIG. 26 as described above shows an example of a user interface that may enable the user to override or change a particular setting in the default configuration profile so that an associated feature of the plurality of features is switched between enabled and disabled. Advantageously, such an implementation may allow the user to even further customize each instance of the hazard detector in their home, based at least in part on where or what location a particular hazard detector is installed, i.e., the designated location. Other examples are possible.

The method may additionally, or alternatively, include or comprise a step 104*f* of outputting, by a speaker system of the hazard detector, an audible request for input of the designated location for installation of the hazard detector, and receiving, via actuation of a mechanical input device of the hazard detector, an indication of the designated location for installation of the hazard detector. FIG. 24 as described above shows an example of such an implementation. Other examples are possible. For instance, the method may additionally, or alternatively, include or comprise a step 104*g* of causing a computing device external to the hazard detector to prompt via user-interface for input of the designated location for installation of the hazard detector, and causing the computing device external to the hazard detector to transmit the designated location to one of the hazard detector and a computing device external to the hazard detector to identify the at least one feature to enable or disable based upon the designated location. FIG. 23 as described above shows an example of such an implementation. Advantageously, such example implementations may allow the user interact directly with the hazard detector to provide input or a specification as to the above mentioned designated location, or when possible, may allow the user interact directly with their smartphone to provide input or a specification as to the above mentioned designated location. Accordingly, a user or customer need not necessarily have a smartphone or even access to a computer to provide input or a specification as to the above-mentioned designated location. Still other examples are possible.

The method may additionally, or alternatively, include or comprise a step 104*h* of receiving a designation of a particular region-specific location of the residence, identifying at least one feature of the plurality of features to enable or disable based upon the designation, and instantiating a command to enable or disable the at least one feature of the plurality of features of the hazard detector. In this example, it is contemplated that the phrase "region-specific" may refer to at least one of a political boundary, a geographical boundary, one or more "subsets" of the same, or any other type or form of demarcation, and etc. For example, a designation of a particular region-specific location of the residence may include "West Coast of the United States" or "California" or "Bay Area" and etc. Other examples may include a postal code, such as 94124, a time zone, such as Pacific Standard Time, a particular street address, and/or any combination thereof. Many other examples are possible, and it is contemplated that such an implementation may advantageously, enable the hazard detector to be served or provided with relevant "region-specific" information that may then be conveyed in some way to a user or customer. For example, information associated with national weather service warnings, Amber Alerts, daylight savings time settings, and etc., may be aggregated by one or more delocalized server systems and then pushed down to the hazard detector and/or a particular smartphone so that a user or customer may be informed of what might be considered particularly relevant information. For example, an audio cue such as "Severe Weather Is Approaching Your Home" may be output by the hazard detector, and at the same time an email or text message or the like might be sent to their smartphone stating the same. Still many other examples are possible.

As mentioned above, the present disclosure is directed to or towards systems, devices, methods, and related computer-program products for providing hazard-detection objectives. Accordingly, the example implementation as discussed in connection with step 104 of FIG. 1 may take many forms. For example, it is contemplated that a hazard detector may include or comprise a plurality of integrated features including one or more alarming functions and one or more home life enhancement functions, and a processing system, in operative communication with the plurality of integrated features, that switches the at least one integrated feature from a first status to one of an enabled status and a disabled status, an indication of which is output as a recommendation via user-interface, in response to a user-based input that designates a particular location within a residence for installation of the hazard detector.

An example of the indication of which is output as a recommendation via user-interface is shown and described above in connection with at least FIG. 25 and FIG. 26. An example processing system is shown and described below in connection with at least FIG. 32 and FIG. 33. Further, it is contemplated that the plurality of integrated features may be selected from, but not limited to, a carbon monoxide detection feature, a motion-activated illumination feature, a doorbell notification feature, an intercom communication feature, a voice command recognition feature, a glass break recognition feature, a distressed voice recognition feature, an occupancy detection feature, and a power outage notification feature. Table 1 below provides a summary of such example features, and among other things illustrates example default or "out-of-box" settings of such features, as well as an example of "recommend" settings of such features itemized on an room-specific (installation) basis:

TABLE 1

| Feature | SK | CO | ML | DL | IC | VR | OA | GB | OD | BC | PO | IAQ |
|---|---|---|---|---|---|---|---|---|---|---|---|---|
| default | ✓ | ✓ | ✓ | ✓ | ✓ | ✓ | X | ✓ | X | ✓ | ✓ | ✓ |
| Location | — | — | — | — | — | — | — | — | — | — | — | — |
| bedroom | ✓ | ✓ | X | X | ✓ | ✓ | X | ✓ | X | ✓ | ✓ | ✓ |
| nursery | ✓ | ✓ | X | X | X | ✓ | X | ✓ | X | X | X | ✓ |
| hall | ✓ | ✓ | ✓ | ✓ | ✓ | ✓ | X | ✓ | X | ✓ | ✓ | ✓ |
| kitchen | ✓ | ✓ | ✓ | ✓ | ✓ | ✓ | X | ✓ | X | ✓ | ✓ | X |
| bath | ✓ | ✓ | ✓ | X | ✓ | ✓ | X | ✓ | X | ✓ | ✓ | ✓ |
| Patio (semi-enclosed) | ✓ | X | ✓ | ✓ | ✓ | ✓ | X | ✓ | ✓ | ✓ | ✓ | X |

TABLE 1-continued

| Feature | SK | CO | ML | DL | IC | VR | OA | GB | OD | BC | PO | IAQ |
|---|---|---|---|---|---|---|---|---|---|---|---|---|
| home theater | ✓ | ✓ | ✓ | ✓ | ✓ | X | X | X | X | ✓ | ✓ | ✓ |
| cigar room | ✓ | ✓ | ✓ | ✓ | ✓ | ✓ | X | ✓ | X | ✓ | ✓ | ✓ |
| laundry | ✓ | ✓ | ✓ | ✓ | ✓ | ✓ | X | ✓ | X | ✓ | ✓ | X |
| gun closet | ✓ | ✓ | ✓ | ✓ | ✓ | ✓ | ✓ | ✓ | X | ✓ | ✓ | ✓ |
| workshop | ✓ | X | ✓ | ✓ | ✓ | ✓ | X | X | X | ✓ | ✓ | X |
| garage | ✓ | X | ✓ | ✓ | ✓ | ✓ | X | ✓ | X | ✓ | ✓ | X |

Table 1 is for example purposes only. In Table 1, "✓" represents "ON" and "X" represent "OFF," and a "default" row shows example default or "out-of-box" settings of features of the hazard detector of the present discussion, e.g., hazard detector 500, that which are itemized in the columns, and the other rows show example "recommended" settings of the itemized features on a room-type-specific basis. With specific reference to the columns, column 1 "SK" represents a smoke detection feature, column 2 "CO" represents a carbon monoxide detection feature, column 3 "ML" represents a motion pathway lighting or "Pathlight" feature, column 4 "DL" represents a doorbell notification feature, column 5 "IC" represents an intercom communication feature, column 6 "VR" represents a voice command recognition feature, column 7 "OA" represents an "alarm if any occupancy" feature, column 8 "GB" represents a glass break microphone feature, column 9 "OD" represents a "disable occupancy detection" feature, column 10 "BC" represents a "notify if baby cry" feature, column 11 "PO" represents a "notify if power outage" feature, and column 12 "IAQ" represents an indoor air quality feature. It will thus be appreciated that such features represent hazard detection features as well as convenience features. This is consistent with the principles of the present disclosure in which it is contemplated that the hazard detector 500 for instance in addition to providing hazard detection capabilities and warnings may also be seamlessly incorporated into a smart home/automation environment. The example features of the hazard detector 500 shown in Table 1 are discussed in further detail in connection with least FIG. 31.

Referring now again back to FIG. 1, as discussed above in connection with the same, FIG. 1 illustrates an example implementation of a particular smart hazard detector, such as the hazard detector 500, that may itself function as a guide during a process of installation of the same at an installation location, and that the installation location of the particular smart hazard detector may play a central role in how various settings of the smart hazard detector are defined and adjusted over time. In particular at step 102, an input may be provided or supplied to a particular smart hazard detector, or a device or system communicatively coupled to or with the smart hazard detector for example, that identifies an installation location within a residence of the smart hazard detector. An example of an installation location may include "Hallway" or "Living Room" or "Garage" of or within a particular residence for instance.

Such a feature or step may in some examples enable a method for configuring a hazard detector having a heads-up pre-alarm capability, a standard emergency alarm capability, and a default configuration profile in which there is a first heads-up pre-alarm threshold for a hazard to be detected and an emergency alarm threshold for the hazard to be detected. An example default configuration/profile is shown and discussed in connection with Table 1 above, and the subject example method may include or comprise a step 102*a*, i.e., a sub-step of step 102 of FIG. 1 for example, of providing an opportunity for a user to input a designated location for installation of the hazard detector within a residence, in a manner similar to that as discussed throughout.

The method may additionally, or alternatively, include or comprise a step 106*a*, i.e., a sub-step of step 106 of FIG. 1 for example, of identifying a second heads-up pre-alarm threshold based upon the designation of the particular location, upon receiving the designated location, and a step 106*b* of instantiating a command to operate the hazard detector according to the second heads-up pre-alarm threshold and the emergency alarm threshold. Other examples are possible. However, in this example and as discussed in detail above, a heads-up pre-alarm is different than an emergency alarm in that a heads-up pre-alarm may be considered more of a gentle warning (e.g., a "beep-beep" followed by a particular audio/visual notification) of the possibility of a dangerous condition or scenario, whereas a standard emergency alarm may be considered more of a serious warning (e.g., an "ear piercing" siren followed by a particular audio/visual notification) that indicates the presence or imminent presence a dangerous condition or scenario.

The method may additionally, or alternatively, include or comprise a step 106*c* of instantiating a command to set the second heads-up pre-alarm threshold to a level greater than the first heads-up pre-alarm threshold when the designated location corresponds to a type of household location predicted to be associated with levels of the hazard to be detected generally greater than one or more other types of household locations. In some examples, the type of household location predicted to be associated with levels of the hazard to be detected generally greater than one or more other types of household locations may be selected from a kitchen type of location and a garage type of location. Other examples are however possible. Advantageously, by raising the pre-alarm threshold in such a manner the hazard detector may be less prone to outputting pre-alarm warnings for a particular type of hazard when it is known that that type of hazard is common or the like, in concentrations that would not necessarily warrant output of a standard emergency alarm. For example, the pre-alarm threshold for a smoke detection feature of a particular hazard detector installed in a kitchen might be "raised" in the example scenario so that smoke from "burnt toast" would not necessarily trigger a heads-up pre-alarm. At the same time, the emergency threshold for the smoke detection feature of the hazard detector installed in the kitchen might be left alone or unchanged so that smoke from an "oil fire," likely to be more substantial than smoke from "burnt toast," would trigger an emergency alarm, assuming one or more associated criterion are determined to be met by the hazard detector. Other examples are possible.

The method may additionally, or alternatively, include or comprise a step 106*d* of instantiating a command to set the second heads-up pre-alarm threshold to a level less than the first heads-up pre-alarm threshold when the designated location corresponds to a type of household location predicted to be frequented by one or more individuals susceptible to irritation by the hazard to be detected. In some examples, the type of household location predicted to be frequented by one or more individuals susceptible to irritation by the hazard to be detected may be selected from a bedroom type of location and a caregiver type of location. Other examples are possible. Advantageously, by lowering the pre-alarm threshold in such a manner the hazard detector may output pre-alarm warnings for a particular type of hazard when it is known that that type of hazard is common in concentrations that might not necessarily trigger a pre-alarm warning if the threshold were not lowered, but those concentrations may or might still affect "at-risk" individuals. For example, the pre-alarm threshold for a smoke detection feature of a particular hazard detector installed in a bedroom of child that has asthma might be "lowered" in the example scenario so that smoke that wafts-in from a kitchen due to "burnt toast" might still trigger a heads-up pre-alarm even though concentration of the smoke in the bedroom might be considered minimal or low. In this way, a parent or guardian might be sufficiently warned so as to be able to address the situation before the child is affected by the smoke, even when there is not much smoke in the air at any particular instance in time. Other examples are possible.

The method may additionally, or alternatively, include or comprise a step 106$e$ of accessing information pre-stored in a database remote from the hazard detector to identify the second heads-up pre-alarm threshold based upon the designation of the particular location. Additionally, or alternatively, the method may include or comprise a step 106$f$ of accessing information pre-stored in a memory of the hazard detector to identify the second heads-up pre-alarm threshold based upon the designation of the particular location. Additionally, or alternatively, the method may include or comprise a step 106$g$, i.e., a sub-step of step 106 of FIG. 1 for example, of periodically or intermittently receiving an update to the second heads-up pre-alarm threshold from a computing system remote from the hazard detector. Advantageously, such an implementation may enable the hazard detector to, when a network connection is available for example, negotiate with a remote server system to identify the second heads-up pre-alarm threshold based upon the designation of the particular location. Such information as stored and/or maintained at or by the remote server system may periodically or at least intermittently be refreshed or updated so that in turn the hazard detector may be supplied the most current and up-to-date information as to a particular "value" of the second heads-up pre-alarm threshold, based upon the designation of the particular location. Accordingly, such information as stored and/or maintained at or by the hazard detector may periodically or at least intermittently be refreshed or updated so that in turn the hazard detector may have the most current and up-to-date information as to a particular "value" of the second heads-up pre-alarm threshold, based upon the designation of the particular location. Other examples are possible.

The method may additionally, or alternatively, include or comprise a step 106$h$ of providing an opportunity for the user to manually modify or adjust the second heads-up pre-alarm threshold. The method may additionally, or alternatively, include or comprise a step 106$i$ of prompting via user-interface for input to modify or adjust the second heads-up pre-alarm threshold, and instantiating a command to increase or decrease the second heads-up pre-alarm threshold based on received user input. It is contemplated that the example user interface of FIG. 26 and/or FIG. 27 may be modified so as to enable such features as discussed in the context of the present disclosure. For example, a "sensitivity" control or button or the like may be positioned or located adjacent or at least near the "CO Detection" ON/OFF button or control as shown in FIG. 26. It is contemplated that an indicator or indication such as "Current threshold setting is CO>=200 ppm instantaneously after 5 min of monitoring, press the 'increase' or 'decrease' control button to increase/decrease the setting in increments of 50 ppm" may be presented. Since the subject hazard detector is installed to a garage type of location, a savvy user or customer might press the "increase" control button until the indicator reads "Current threshold setting is CO>=400 ppm instantaneously after 5 min of monitoring, press 'increase' or 'decrease' control button to increase/decrease concentration setting in increments of 50 ppm." By raising the pre-alarm threshold in this scenario, annoying false alarms due the starting of a vehicle for example might be minimized. It is contemplated that such an action when performed may ultimately enable the hazard detector to self-adjust its pre-alarm threshold setting(s) so the subject pre-alarm threshold of the present example may be raised or elevated or increased accordingly. Advantageously, such an implementation may allow the user to even further customize each instance of the hazard detector in their home, based at least in part on where or what location a particular hazard detector is installed, i.e., based upon the designation of the particular location. Other examples are possible.

As mentioned above, the present disclosure is directed to or towards systems, devices, methods, and related computer-program products for providing hazard-detection objectives. Accordingly, the example implementation as discussed in connection with step 106 of FIG. 1 may take many forms. For example, it is contemplated that a hazard detector may include or comprise at least one hazard detection feature, and a processing system, in operative communication with the at least one hazard detection feature, that adjusts a first heads-up pre-alarm threshold of the at least one hazard detection feature to a second heads-up pre-alarm threshold in response to a user input that identifies a particular installation location of the hazard detector within a residence, so that the at least one hazard detection feature operates according to the second heads-up pre-alarm threshold for a hazard to be detected, and a standard emergency alarm threshold for the hazard to be detected.

In one example, the second heads-up pre-alarm threshold may be adjusted to a level greater than the first heads-up pre-alarm up threshold. In another example, the second heads-up pre-alarm threshold is adjusted to a level less than the first heads-up pre-alarm up threshold. In one example, the at least one hazard detection feature may in include or comprise a carbon monoxide detection feature. In another example, the at least one hazard detection feature may include or comprise a smoke detection feature. Many other examples are possible. Further, it is contemplated that the hazard detector may include or comprise any of a variety of other components or elements.

For example, the hazard detector may include or comprise an output device, such as a speaker and/or microphone system. In this example, it is contemplated that a particular audible alert of first volume intensity may be generated by the output device when a detected magnitude of the hazard is determined to be greater than the second heads-up pre-alarm threshold and less than the emergency alarm threshold, and another particular audible alert of second volume intensity greater than the first volume intensity may be generated by the output device when the detected magnitude of the hazard is determined to be greater than the emergency alarm threshold. Such an implementation is consistent with the above-described differences between heads-up pre-alarms and standard emergency alarms of the present disclosure. In particular, a heads-up pre-alarm is different than a standard emergency alarm in that a heads-up pre-alarm may be considered more of a gentle warning of the possibility of a dangerous condition or scenario, whereas an emergency alarm may be considered more of a serious warning that indicates the presence or imminent presence a dangerous condition or scenario. It is though contemplated that other alarms or alerts may be output by the output device.

For instance, in one example a particular audible alert may be output by the output device when a detected magnitude of the above-mentioned hazard is determined to be increasing, to indicate rising levels of the hazard. An example of such an output may include “CO levels are increasing. Open a window in the bedroom.” Other examples are possible. For instance, in one example a particular audible alert may be output by the when a detected magnitude of the above-mentioned hazard is determined to be decreasing, to indicate falling levels of the hazard. An example of such an output may include “CO levels are decreasing and it has been detected that the window in the bedroom is open. It is OK to now close the window in the bedroom.” Still many other examples are possible.

Referring now again back to FIG. 1, as discussed above in connection with the same, FIG. 1 illustrates an example implementation of a particular smart hazard detector, such as the hazard detector 500, that may itself function as a guide during a process of installation of the same at an installation location, and that the installation location of the particular smart hazard detector may play a central role in how various settings of the smart hazard detector are defined and adjusted over time. With reference to step 108, such an implementation may enable a method for guiding installation of a hazard detector. For example, the method may include or comprise a step 108*a*, i.e., a sub-step of step 108 of FIG. 1 for example, of receiving, by the hazard detector during installation at a particular location within a residence, an input command to test whether an instant placement of the hazard detector would prevent the hazard detector from operating within specification to detect and/or mitigate one or more hazards. The method may additionally, or alternatively, include or comprise a step 108*b* of implementing, by the hazard detector in response to receiving the input command, a test sequence to determine whether the instant placement of the hazard detector would prevent the hazard detector from operating within specification to detect and/or mitigate one or more hazards. The method may additionally, or alternatively, include or comprise a step 108*c* of outputting, by the hazard detector, a particular notification during installation at the particular location when it is determined that the instant placement of the hazard detector would prevent the hazard detector from operating within specification to detect and/or mitigate one or more hazards, based upon readings of at least one component of the hazard detector.

Other examples are possible. In the present example though, the phrase “instant placement” may in some examples refer to a “current” or “present” position and/or orientation of the hazard detector as intended for installation. For example, an individual who is in the process of installing the hazard detector may hold the same in their hand and then place or position the hazard detector to a specific location or spot on a ceiling in a hallway of the residence. At this point though the hazard detector is not secured or otherwise fastened to the ceiling. That though may be done to perfect installation of the hazard detector at the instant placement of the same. Further, the phrase “prevent the hazard detector from operating within specification to detect and/or mitigate one or more hazards” or variations thereof may in some examples refer to a scenario in which at least one function or feature of the hazard detector would not be able to operate or function as intended if the hazard detector were secured or otherwise fastened at a position corresponding to the instant placement of the same. For example, if the hazard detector were worst case scenario placed in a drawer or closet, features such as a carbon monoxide detector, smoke detector, ambient light detector, etc., of the hazard detector may not operate as intended if the hazard detector were secured or otherwise fastened to surface in the drawer. This is because the hazard detector in this example would be installed in a tightly confined space. As another example, if the hazard detector were installed in a ceiling corner, this may violate a recommended and/or mandated placement of the hazard detector to be 6 inches or greater or more from any particular wall surface for example. Still many other examples are possible.

The method may additionally, or alternatively, include or comprise a step 108*d* of determining, based upon readings of a proximity sensor of the hazard detector, that the instant placement of the hazard detector is within a prohibitive distance from one or more wall or ceiling surfaces, and in response to the determining, outputting the particular notification to indicate that the instant placement of the hazard detector would prevent the hazard detector from operating within specification to detect and/or mitigate one or more hazards. In some examples, the proximity sensor may comprise of an ultrasonic sensor. In other example, the proximity sensor may comprise of an LED time-of-flight range finder. Still many other examples are possible. In these examples though, it is contemplated that the proximity sensor may transmit an interrogating pulse, such as once every 10 milliseconds for example, so that the proximity sensor and ultimately the hazard detector may determine if the hazard detector, at a position corresponding to the instant placement of the same, is too close to a surface of one or more walls, for example. If this were the case, it is contemplated that the hazard detector may provide feedback, such as an audible “the hazard detector is placed too close to the wall” and/or a visual “flashing red” or “flashing yellow” sequence, as output by the light ring 522 of the hazard detector. In practice, if the hazard detector were in real-time moved to a distance that is not or no longer too close to a surface of one or more walls, it is contemplated that the hazard detector may provide additional feedback, such as an audible “the hazard detector is no longer too close the wall” and/or a visual “flashing green” sequence or a “steady green” visual cue. Still many other examples are possible.

The method may additionally, or alternatively, include or comprise a step 108*e* of determining, based upon a reading of an orientation sensor of the hazard detector, that an instant spatial orientation of the hazard detector is unsuitable for one or more features of the hazard detector to operate as intended, and in response to the determining, outputting the particular notification to indicate that the instant placement of the hazard detector would prevent the hazard detector from operating within specification to detect and/or mitigate one or more hazards. In some examples, the orientation sensor may comprise of an accelerometer. In some examples, the orientation sensor may comprise of a gyroscope. Still many other examples are possible. In these examples though, it is contemplated that the orientation sensor may detect an instant orientation of the hazard detector, such as +45 degrees as measured with respect to a reference axis or normal as shown in FIG. 24, which might be defined as “0 degrees” when the hazard detector is placed “face-up” on a flat surface. Thus in a typical installation scenario, the hazard detector when positioned to a flat ceiling surface may be determined by the orientation sensor to be at 180 degrees as measured with respect to a reference axis or normal as shown in FIG. 24. The example method though by which the hazard detector or a component thereof quantifies or determines orientation of the hazard detector is an example only. In many instances, the orientation sensor of the hazard detector itself may be calibrated so that no frame of reference as defined with respect to another features or surface of the hazard detector would be needed or necessary.

In some examples, a particular orientation may not be preferable in comparison to other orientations. For example, in some implementation-specific situations or scenarios, it may be more preferred to have the hazard detector when installed to be at 180 degrees (e.g., approximately upside-down), as opposed to +45 degrees or within a tolerance range thereof. Further, similar to the above-example, it is contemplated that the hazard detector may provide feedback, such as an audible "the hazard detector is currently placed at a non-optimal angle" and/or a visual "flashing red" or "flashing yellow" sequence, as output by the light ring 522 of the hazard detector. In practice, if the hazard detector were in real-time moved or manipulated to a more optimal or preferred orientation, it is contemplated that the hazard detector may provide additional feedback, such as an audible "the hazard detector is currently placed at an appropriate angle" and/or a visual "flashing green" sequence or a "steady green" visual cue. Still many other examples are possible.

The method may additionally, or alternatively, include or comprise a step **108*f* of determining that an instant wireless signal strength detected by the hazard detector is within an unacceptable range, and in response to the determining, outputting the particular notification to indicate that the instant placement of the hazard detector would prevent the hazard detector from operating within specification to detect and/or mitigate one or more hazards. In some examples, a WiFi module or radio of the hazard detector may determine that signal strength is too low or too intermittent or the like for the hazard detector to establish a reliable communication link with a local network or the like. Here, it is contemplated that the hazard detector may provide feedback, such as an audible "the hazard detector cannot connect to the home network" and/or a visual "flashing red" or "flashing yellow" sequence, as output by the light ring 522** of the hazard detector. In practice, if the hazard detector were in real-time moved or manipulated to a more optimal orientation, it is contemplated that the hazard detector may provide additional feedback, such as an audible "signal strength is good and the hazard detector is now connected to the home network" and/or a visual "flashing green" sequence or a "steady green" visual cue. Still many other examples are possible.

The method may additionally, or alternatively, include or comprise a step **108*g* of determining that a particular hazard detection feature of the hazard detector is operating within an unacceptable range due to instant or current readings being outside of an acceptable range, and in response to the determining, outputting the particular notification to indicate that the instant placement of the hazard detector would prevent the hazard detector from operating within specification to detect and/or mitigate one or more hazards. In some examples, the particular hazard detection feature may comprise of a carbon monoxide detection feature. In some examples, the particular hazard detection feature may comprise of a smoke detection feature. In some examples, the particular hazard detection feature may comprise of an ambient light sensor detection feature. In some examples, the particular hazard detection feature may comprise of an ambient temperature detection feature. Still many other examples are possible. In these examples though, if the particular hazard detection feature cannot function properly due to sensor or sensory overload, an obstruction, or the like, the hazard detector may provide feedback, such as an audible "the temperature sensor of the hazard detector is not functioning properly, is the hazard detector placed in direct sunlight?" and/or a visual "flashing red" or "flashing yellow" sequence, as output by the light ring 522** of the hazard detector. In practice, if the hazard detector were in real-time moved or manipulated to a more optimal orientation or position, it is contemplated that the hazard detector may provide additional feedback, such as an audible "the temperature sensor of the hazard detector is now functioning properly and/or a visual "flashing green" sequence or a "steady green" visual cue. Still many other examples are possible.

As mentioned above, the present disclosure is directed to or towards systems, devices, methods, and related computer-program products for providing hazard-detection objectives. Accordingly, the example implementation as discussed in connection with step 108 of FIG. 1 may take many forms. For example, it is contemplated that a hazard detector may include or comprise at least one component to test during installation of the hazard detector at a particular location whether an instant placement of the hazard detector would prevent the hazard detector from operating within specification to detect and/or mitigate one or more hazards, and a processing system, in operative communication with the at least one component, that determines, based upon readings of the at least one component, whether an instant placement of the hazard detector during installation thereof would prevent the hazard detector from operating within specification to detect and/or mitigate one or more hazards, and when it is determined that the instant placement of the hazard detector would prevent the hazard detector from operating within specification to detect and/or mitigate one or more hazards, causes a notification alert to be output to guide a user during installation of the hazard detector to a suitable installation location for the hazard detector. In this example, it is contemplated that the at least one component may take many forms, examples of which are discussed here and also in further detail in connection with at least FIG. 31.

For instance, in one example the at least one component may include or comprise an ultrasound sensor that determines a distance of the hazard detector from at least one surface in proximity to the hazard detector based on reflections of interrogating ultrasonic waves. As another example, the at least one component may include or comprise a time-of-flight LED component that determines a distance of the hazard detector from at least one surface in proximity to the hazard detector based on reflections of interrogating optical waves. As yet another example, the at least one component may include or comprise a video camera that determines a distance of the hazard detector from at least one surface in proximity to the hazard detector based on image segmentation and surface recognition. In such implementation-specific examples, the notification alert may be output by the hazard detector when it is determined that the distance of the hazard detector from the at least one surface is less than or equal to a predetermined and regulated distance. Such a distance may be an authority mandated distance, such as 12 inches or greater from a wall surface for example. Other examples are possible and may be specific to region-specific or country-specific, possibly mandated, requirements.

As another example, the at least one component may include or comprise a GPS component that determines whether the particular location is of a type prohibitive for installation of the hazard detector. In this example, the notification alert may be output by the hazard detector when it is determined that the particular location is a prohibited or non-recommended type for installation of the hazard detector, such as a garage or shed for example. For instance, the GPS component may be able to resolve, possibly in tandem with one or more other component of the hazard detector such as a WiFi module or radio that might be able to derive via triangulation approximate position or location of the hazard detector within the residence, that the hazard detector an intended installation location of the hazard detector is a garage or shed for example. Here, based on that determination, the hazard detector might output an audible "the garage is not an optimal location of installation, the hallway adjacent the garage might be a better choice" and/or a visual "flashing red" or "flashing yellow" sequence, as output by the light ring 522 of the hazard detector. In the example scenario, if the hazard detector were in real-time moved to "the hallway adjacent the garage" for installation thereto, it is contemplated that the hazard detector may provide additional feedback, such as an audible "thank you for deciding to install at the recommended location" and/or a visual "flashing green" sequence or a "steady green" visual cue. Still many other examples are possible.

As yet another example, the hazard detector may include or comprise various other components, such as a communication interface that receives from a camera system external to the hazard detector an indication of whether the instant placement of the hazard detector would prevent the hazard detector from operating within specification to detect and/or mitigate one or more hazards. In this example, notification alert may be output by the hazard detector when it is determined, based upon the indication, that the instant placement of the hazard detector would prevent the hazard detector from operating within specification to detect and/or mitigate one or more hazards. For example, the camera system may detect that the hazard detector is being installed in a closet and then transmit a particular signal to the hazard detector to prompt the hazard detector to output an audible "the closet is not an optimal location for installation of your hazard detector, the ceiling in the bedroom is, but do not install the hazard detector so that it is within 6 inches of any wall surface" and/or a visual "flashing red" or "flashing yellow" sequence, as output by the light ring 522 of the hazard detector. In the example scenario, if the hazard detector were in real-time moved to "the ceiling in the bedroom is" for installation thereto, it is contemplated that the hazard detector may provide additional feedback, such as an audible "thank you for deciding to install at the recommended location" and/or a visual "flashing green" sequence or a "steady green" visual cue. Still many other examples are possible.

Referring now again back to FIG. 1, as discussed above in connection with the same, FIG. 1 illustrates an example implementation of a particular smart hazard detector, such as the hazard detector 500, that may itself function as a guide during a process of installation of the same at an installation location, and that the installation location of the particular smart hazard detector may play a central role in how various settings of the smart hazard detector are defined and adjusted over time. With reference to step 110, such an implementation may enable a method for adjusting pre-alarm thresholds of a hazard detector that is installed to a particular location within a residence and that has a heads-up pre-alarm capability and a standard emergency alarm capability. For example, the method may include or comprise a step 110*a*, i.e., a sub-step of step 110 of FIG. 1 for example, of analyzing data as detected by a particular sensor of the hazard detector over a particular time period to identify a reoccurring trend in which hazard levels are sufficient to exceed a pre-alarm threshold but insufficient to exceed an emergency alarm threshold, and a step 110*b* of raising the pre-alarm threshold to a particular level upon detection of onset of a subsequent instance of the reoccurring trend so that the hazard detector is less prone to instantiate a pre-alarm alert for detected instances of the reoccurring trend, but does instantiate a pre-alarm alert in absence of the reoccurring trend and when detected hazard levels are sufficient to exceed the pre-alarm threshold but insufficient to exceed the emergency alarm threshold.

Other examples are possible. In the present example though, the particular time period may correspond to one of a particular day time period, a particular week time period, a particular month time period, and a particular year time period. Further, historical data as acquired by the particular sensor of the hazard detector may be analyzed to identify a reoccurring or recurring trend in the data that may be representative of and/or reflect on a particular user-activity or the like for instance. For example, upon an analysis of the historical data as acquired by the particular sensor of the hazard detector, it may be determined that every morning Monday-Friday carbon monoxide levels moderately increase generally sometime between 6:30 AM to 7:00 AM, and then dissipate relatively quickly. In this example, it is contemplated that an initial pre-alarm threshold for carbon monoxide level may be set low enough so that levels associated with the reoccurring trend may trigger a pre-alarm alert, but do not trigger an emergency alarm. Here, the hazard detector may, in response to a command, raise or increase the pre-alarm threshold to a particular level so that the reoccurring trend does not trigger a pre-alarm alert. When the reoccurring trend though is not detected by the hazard detector and carbon monoxide levels exceed the initial pre-alarm threshold, the levels may still trigger a pre-alarm alert.

The method may additionally, or alternatively, include or comprise a step 110*c*, i.e., a sub-step of step 110 of FIG. 1 for example, of correlating occurrence of the reoccurring trend with a particular sensor reading of another particular sensor of the hazard detector, and raising the pre-alarm threshold to the particular level upon detection of onset of the subsequent instance of the reoccurring trend and when an instant sensor reading of the another particular sensor correspond to the particular sensor reading. In this example, historical data as acquired by another particular sensor of the hazard detector may too or in tandem be examined or analyzed, possibility during or concurrently to step 110*a*, to determine whether another detectable event typically coincides with occurrence of the reoccurring trend. For example, historical data as acquired by an ambient light sensor of the hazard detector may indicate that a general increase in light intensity or brightness, such as due to the opening of a garage door, typically coincides with occurrence of the reoccurring trend, a carbon monoxide trend in this example. In this example, detection by the hazard detector of the reoccurring trend and a general increase in light intensity or brightness may trigger the hazard detector to raise the pre-alarm threshold to the particular level. Other examples are possible.

The method may additionally, or alternatively, include or comprise a step 110*d* of correlating occurrence of the reoccurring trend with a particular hazard level as detected by a particular sensor of another hazard detector that is installed to another particular location within the residence, and raising the pre-alarm threshold to the particular level upon detection of onset of the subsequent instance of the reoccurring trend and when an instant hazard level as detected by the particular sensor of the another hazard detector is greater than or equal to the particular hazard level. In this example, historical data as acquired by a particular sensor of another hazard detector may too be examined or analyzed, possibility during step 110*a*, to determine whether another detectable event typically coincides with occurrence of the reoccurring trend. For example, historical data as acquired by an occupancy sensor of the another hazard detector may indicate that presence of an individual in a living room typically coincides with occurrence of the reoccurring trend that is detected by the hazard detector installed to a garage. In this example, this may correspond to the individual waiting for their car to warm-up in the garage, and detection by the hazard detector of the reoccurring trend, a carbon monoxide trend in this example, together with an affirmative occupancy sensor reading of the another hazard detector may trigger the hazard detector to raise the pre-alarm threshold to the particular level. Other examples are possible.

The method may additionally, or alternatively, include or comprise a step 110*e* of correlating occurrence of the reoccurring trend with a particular status of a particular element of a home automation system installed at the residence, and raising the pre-alarm threshold to the particular level upon detection of onset of the subsequent instance of the reoccurring trend and when an instant status of the particular element of the home automation system corresponds to the particular status. In this example, the hazard detector may be communicatively coupled to a home automation gateway device, and historical data as acquired by the home automation gateway device may too be examined or analyzed, possibility during step 110*a*, to determine whether another detectable event typically coincides with occurrence of the reoccurring trend. For example, historical data as acquired by the home automation gateway device may indicate that the opening of a garage door typically coincides with occurrence of the reoccurring trend, a carbon monoxide trend in this example. In this example, detection by the hazard detector of the reoccurring trend and opening of the garage door may trigger the hazard detector to raise the pre-alarm threshold to the particular level. Other examples are possible.

The method may additionally, or alternatively, include or comprise a step 110*f* of correlating occurrence of the reoccurring trend with a particular time period of day, and raising the pre-alarm threshold to the particular level upon detection of onset of the subsequent instance of the reoccurring trend and when an instant time of day is determined by the hazard detector to correspond with the particular time period of day. The method may additionally, or alternatively, include or comprise a step 110*g* of correlating occurrence of the reoccurring trend with a particular time period of year, and raising the pre-alarm threshold to the particular level upon detection of onset of the subsequent instance of the reoccurring trend and when an instant time of day is determined by the hazard detector to correspond with the particular time period of year. In these examples, it is contemplated that a temporal aspect such as time of day and/or time of year may play into the decision by the hazard detector to raise the pre-alarm threshold.

For example, upon an analysis of the historical data as acquired by the particular sensor of the hazard detector, it may be determined that every morning Monday-Friday carbon monoxide levels moderately increase generally sometime between 6:30 AM to 7:00 AM, and then dissipate relatively quickly. As another example, upon an analysis of the historical data as acquired by the particular sensor of the hazard detector, it may be determined that every morning M-F only during the winter months carbon monoxide levels moderately increase generally sometime between 6:30 AM to 7:00 AM, and then dissipate relatively quickly. In these examples, detection by the hazard detector of the reoccurring trend during the time period between 6:30 AM to 7:00 AM, and possibly during a particular winter month such as January, may trigger the hazard detector to raise the pre-alarm threshold to the particular level. Other examples are possible.

As mentioned above, the present disclosure is directed to or towards systems, devices, methods, and related computer-program products for providing hazard-detection objectives. Accordingly, the example implementation as discussed in connection with step 110 of FIG. 1 may take many forms. For example, it is contemplated that a hazard detector that is installed to a particular location within a residence and that has a heads-up pre-alarm capability and a standard emergency alarm capability may include or comprise at least one sensor, and a processing system, in operative communication with the least one sensor, that raises a pre-alarm threshold associated with the at least one sensor to a particular level in response to detection, by the at least one sensor, of onset of an instance of a recurring trend so that the hazard detector is less prone to instantiate a pre-alarm alert for detected instances of the recurring trend, but does instantiate a pre-alarm alert in absence of the recurring trend and when hazard levels detected by the at least one sensor are sufficient to exceed the pre-alarm threshold but insufficient to exceed an emergency alarm threshold associated with the at least one sensor. Such a feature may be beneficial and/or advantages for reasons similar to that discussed above in connection with at steps 110*a-g*. Still other examples are possible as may be understood upon inspection of the present application in its entirety.

Figure 31:
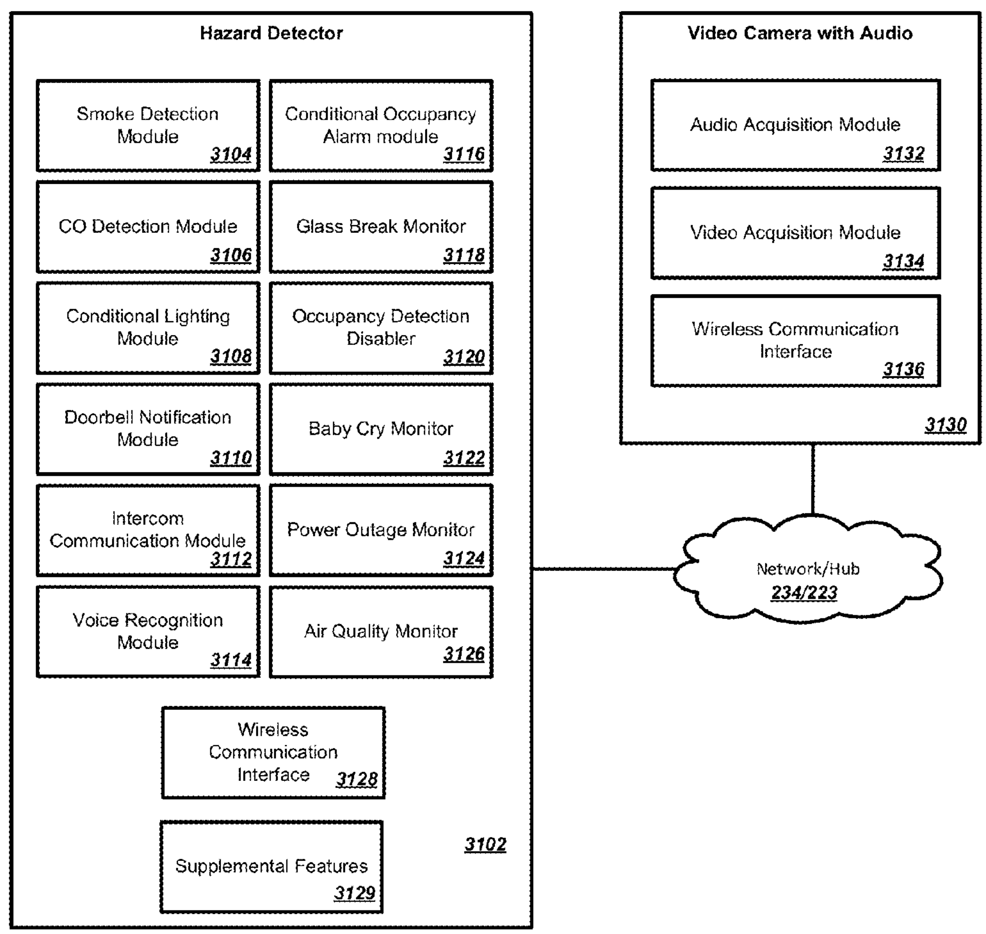
FIG. 31 shows an example system that includes the detector of FIG. 5.

Referring now to FIG. 31, an embodiment of system 3100 that includes a hazard detector 3102 having various components that can be enabled or disabled separately depending on the operating environment of the hazard detector 3102 is shown. In general, the hazard detector 3102 may correspond to the hazard detector 500 as shown and described above. The hazard detector 3102 may include a smoke detection module 3104, a carbon monoxide detection module 3106, a conditional lighting module 3108, a doorbell notification module 3110, an intercom communication module 3112, a voice recognition module 3114, a conditional occupancy alarm module 3116, a glass break monitor 3118, an occupancy detection disabler 3120, a baby cry monitor 3122, a power outage monitor 3124, an air quality monitor 3126, and a wireless communication interface 3128. One or more of such components may be implemented using one or more processors of the hazard detector 3102 and/or one or more sensors of the hazard detector 3102.

The smoke detection module 3104 may represent one or more sensors configured to detect smoke in the environment of the hazard detector 3102. The smoke detection module 3104 may be configured to determine when smoke levels in the ambient environment of the hazard detector has risen above one or more threshold values. For instance, the smoke detection module 3104 may determine when the smoke level in the ambient environment has reached a pre-alarm level (e.g., a "heads-up") and also when it has reached an alarm (emergency) level. The smoke detection module 3104 may be enabled or disabled depending on the type of location in which hazard detector 3102 has been specified as installed.

The carbon monoxide detection module 3106 may represent one or more sensors configured to detect carbon monoxide in the environment of the hazard detector 3102. The carbon monoxide detection module 3106 may be configured to determine when carbon monoxide levels in the ambient environment of the hazard detector has risen above one or more threshold values. For instance, the carbon monoxide detection module 3106 may determine when the carbon monoxide level in the ambient environment has reached a pre-alarm level (e.g., a "heads-up") and also when it has reached an alarm (emergency) level. The carbon monoxide detection module 3106 may be enabled or disabled depending on the type of location in which hazard detector 3102 has been specified as installed. As an example, if hazard detector 3102 is installed within a garage, it may be desirable for carbon monoxide detection module 3106 to be disabled to prevent pre-alarms based on a vehicle's emissions.

The conditional lighting module 3108, which may also be referred to as a path light feature, may output lighting (e.g., via light ring 522) under certain conditions, such as when motion is detected in the ambient environment of the hazard detector 3102 and the brightness level detected by a light sensor of the hazard detector 3102 indicates the ambient brightness level is below a stored threshold value. The conditional lighting module 3108 may therefore illuminate a light of the hazard detector 3102 when a user is moving in the vicinity of the hazard detector 3102 in the dark. The conditional lighting module 3108 may be enabled or disabled depending on the type of location in which hazard detector 3102 has been specified as installed. As an example, if hazard detector 3102 is installed within a bedroom, it may be desirable for conditional lighting module 3108 to be disabled such that movements of a person while asleep do not trigger the conditional lighting module 3108 to activate the light of the hazard detector 3102.

The doorbell notification module 3110 and the intercom communication module 3112 may, respectively, be coupled either directly or indirectly via a home automation gateway system, to enable the hazard detector 3102 to output via speaker system a notification (e.g., doorbell sound) when a particular doorbell actuator is pressed, and to enable the hazard detector 3102 to function as a two-way communication system via a microphone/speaker system incorporated into the intercom communication module 3112. The voice recognition module 3114 in contrast may be configured to receive affirmative voice commands via one or more microphones of the hazard detector 3102. For instance, commands may be received to enable or disable various other modules of the hazard detector 3102. As an example, a user may be able to state "disable conditional lighting module." Such a command may disable the illumination of a light of the hazard detector when motion is detected and the ambient brightness levels are below threshold value.

The voice recognition module 3114 and/or the baby cry monitor 3122 may also be able to perform distressed voice recognition. Such distressed voice recognition may be the ability to identify stress in a human voice in the ambient environment of the hazard detector. Such detection may be useful for determining when an emergency is present in the vicinity of the hazard detector, if a baby is crying, and etc. The voice recognition module 3114 may be enabled or disabled depending on the type of location in which the hazard detector 3102 has been specified as installed. As an example, if the hazard detector 3102 is installed within a home theatre (or other place where a television is typically present), it may be desirable for the voice recognition module 3114 to be disabled (or at least the distressed voice recognition is disabled) such that human voice from a television program (e.g., a scary movie) does not trigger an action by voice recognition module 3114.

The conditional occupancy alarm module 3116 may monitor for undesired human presence, such as in a home security scenario, and when an undesired human presence is detected the conditional occupancy alarm module 3116 may command the hazard detector to output an emergency alarm and possible contact a third party, such as 911 for example. In some examples, the occupancy detection disabler 3120 may enable/disable occupancy detection functionality of the hazard detector 3102. The glass Break monitor 3118 may be configured to monitor for the sound of glass breaking in the ambient environment of hazard detector 3102. The glass break monitor 3118 may receive audio via one or more microphones of the hazard detector 3102. The glass break monitor 3118 may be triggered to alert one or more other devices if glass is detected as breaking, possibly signaling a break-in or vandalism. The glass break monitor 3118 may be enabled or disabled depending on the type of location in which the hazard detector 3102 has been specified as installed. As an example, if the hazard detector 3102 is installed within a home theatre (or other place where a television is typically present), it may be desirable for the glass break monitor 3118 to be disabled such that sound from a television program (e.g., an action movie) does not trigger an action by the glass break monitor 3118.

The baby cry monitor 3122 may be configured to monitor for the sound of a baby crying in the ambient environment of the hazard detector 3102. The baby cry monitor 3122 may receive audio via one or more microphones of hazard detector 3102. The baby cry monitor 3122 may be triggered to alert one or more other devices if a baby is determined to be crying in the vicinity of the hazard detector. The baby cry monitor 3122 may be enabled or disabled depending on the type of location which hazard detector 3102 has been specified as installed. As an example, if the hazard detector 3102 is installed within a nursery, it may be desirable for the baby cry monitor 3122 to be disabled such that a baby crying where it is usually located (e.g., his or her crib) does not trigger an action by the baby cry monitor 3122.

The power outage monitor 3124 may be configured to monitor for the hazard detector 3102 losing power from the electrical power source of a structure, which is typically 120 VAC or 240 VAC. The power outage monitor 3124 may be configured to determine when power is no longer available via the structures wired power source to the hazard detector 3102. The power outage monitor 3124 may confirm the power loss via one or more additional arrangements, such as by detecting the decrease in artificial lighting at around the same time power was lost or, for example, by receiving a message from another smart home device indicative of power being lost. The power outage monitor 3124 may be enabled or disabled depending on the type of location which the hazard detector 3102 has been specified as installed. As an example, if the hazard detector 3102 is installed on a circuit that loses power frequently, it may be desirable for the power outage monitor 3124 to be disabled such that a temporary power loss does not trigger an action by the power outage monitor 3124.

The air quality monitor 3126 may be configured to monitor the air quality in the vicinity of the hazard detector 3102. The air quality monitor 3126 may monitor the ambient air quality for various contaminants, such as volatile organic compounds, carbon monoxide, excessive carbon dioxide, ammonium, etc. The air quality monitor 3126 may be configured to notify one or more devices when various stored threshold values are met by measurements of the ambient air. The air quality monitor 3126 may be enabled or disabled depending on the type of location which the hazard detector 3102 has been specified as installed. As an example, if the hazard detector 3102 is installed in a kitchen, it may be desirable for the air quality monitor 3126 to be disabled such that burning food does not trigger an action by the air quality monitor 3126.

The supplemental features module 3129 may include one or more features to at least enable the hazard detector 3102 to output a particular notification during installation of the hazard detector 3102 at the particular location, when it is determined that an instant placement of the hazard detector may prevent the hazard detector 3102 from operating within specification to detect and/or mitigate one or more hazards. An example of such a feature may include, but is not limited to, a proximity sensor such as an ultrasonic sensor and an LED time-of-flight range finder for example, an orientation sensor such as an accelerometer and gyroscope for example, a wireless signal strength module for example, a carbon monoxide detection feature, a smoke detection feature, an ambient light sensor detection feature, and an ambient temperature detection feature for example. Another example of such a feature includes a video camera that determines a distance of the hazard detector 3102 from at least one surface in proximity to the hazard detector based on image segmentation and surface recognition. Another example of such a feature includes a GPS component that determines whether a particular location of installation of the hazard detector 3102 is of a type prohibitive for installation of the hazard detector.

Also shown in FIG. 31 is a video camera 3130 that is separate and external from the hazard detector 3102. The video camera 3130 camera includes an audio acquisition module 3132 to acquire or capture audio, a video acquisition module 3134 to acquire or capture video, and a communication interface 3136 to transfer audio and/or video to the communication interface 3128 of the hazard detector 3102, possibly along with an indication of whether an instant placement of the hazard detector 3102 might prevent the hazard detector 3102 from operating within specification to detect and/or mitigate one or more hazards in a manner as discussed throughout.

Figure 32:
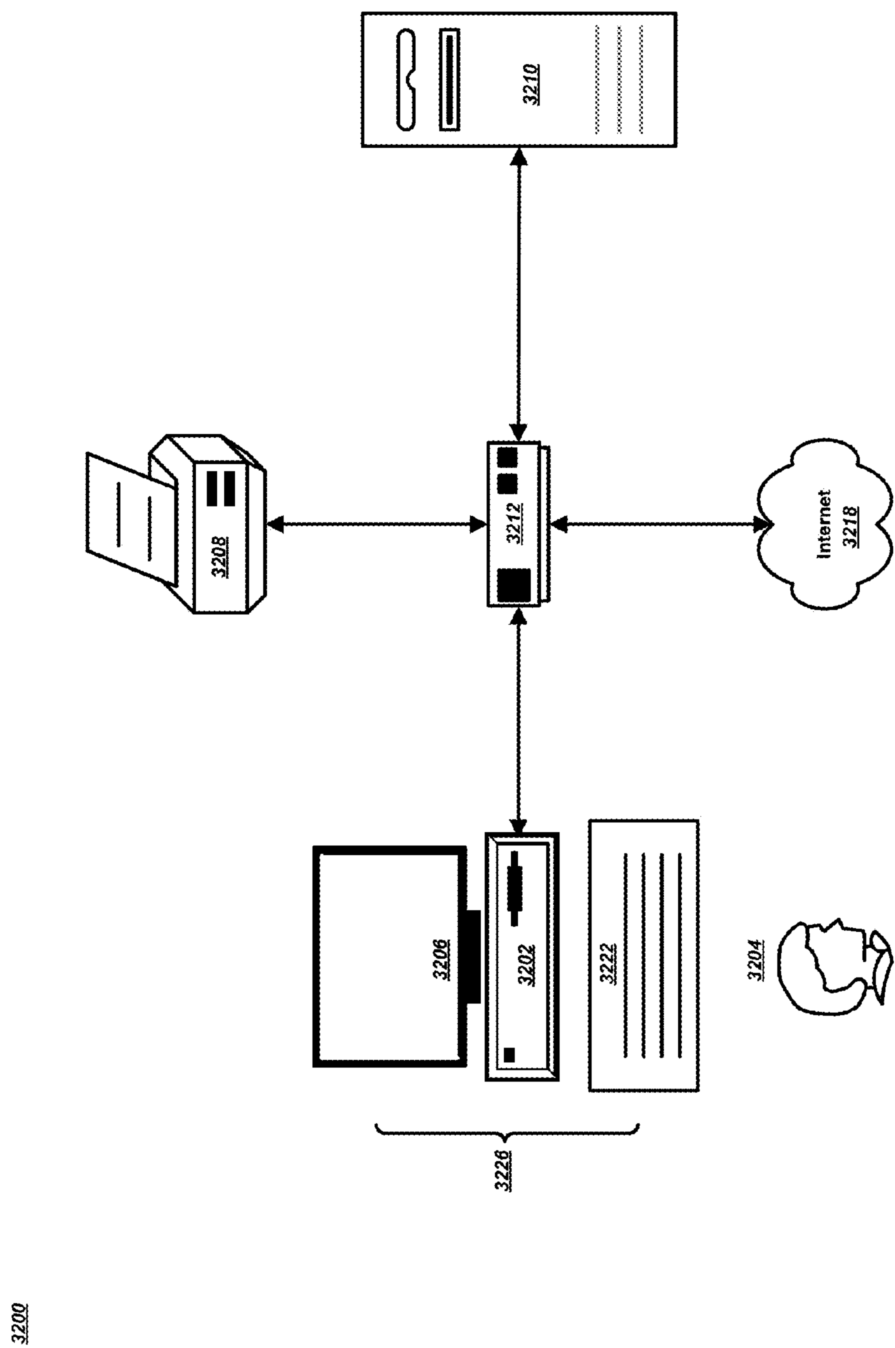
FIG. 32 shows an example computing environment according to the disclosure.

Referring now to FIG. 32, an exemplary environment with which examples may be implemented is shown with a computer system 3200 that can be used by a user 3204 to remotely control, for example, one or more of the sensor-equipped smart home devices according to one or more of the examples. The computer system or server 3210 can alternatively be used for carrying out one or more of the server-based processing paradigms described hereinabove or as a processing device in a larger distributed virtualized computing scheme for carrying out the described processing paradigms, or for any of a variety of other purposes consistent with the present teachings. The computer system 3200 can include a computer 3202, keyboard 3222, a network router 3212, a printer 3208, and a monitor 3206. The monitor 3206, computer 3202 and keyboard 3222 are part of a computer system 3226, which can be a laptop computer, desktop computer, handheld computer, mainframe computer, etc. The monitor 3206 can be a CRT, flat screen, etc.

A user 3204 can input commands into the computer 3202 using various input devices, such as a mouse, keyboard 3222, track ball, touch screen, etc. If the computer system 3200 comprises a mainframe, a user 3204 can access the computer 3202 using, for example, a terminal or terminal interface. Additionally, the computer system 3226 may be connected to a printer 3208 and a server 3210 using a network router 3212, which may connect to the Internet 3218 or a WAN. While element 3218 is labeled "Internet," it is contemplated that element 3218 may incorporate or exhibit any number of features or elements of various wireless and/or hardwired packet-based communication networks such as, for example, a WAN (Wide Area Network) network, a HAN (Home Area Network) network, a LAN (Local Area Network) network, a WLAN (Wireless Local Area Network) network, a cellular communications network, or any other type of communication network configured such that data may be transferred between and among respective elements of the environment 200.

The server 3210 may, for example, be used to store additional software programs and data. In one example, software implementing the systems and methods described herein can be stored on a storage medium in the server 3210. Thus, the software can be run from the storage medium in the server 3210. In another example, software implementing the systems and methods described herein can be stored on a storage medium in the computer 3202. Thus, the software can be run from the storage medium in the computer system 3226. Therefore, in this example, the software can be used whether or not computer 3202 is connected to network router 3212. Printer 3208 may be connected directly to computer 3202, in which case, the computer system 3226 can print whether or not it is connected to network router 3212.

Figure 33:
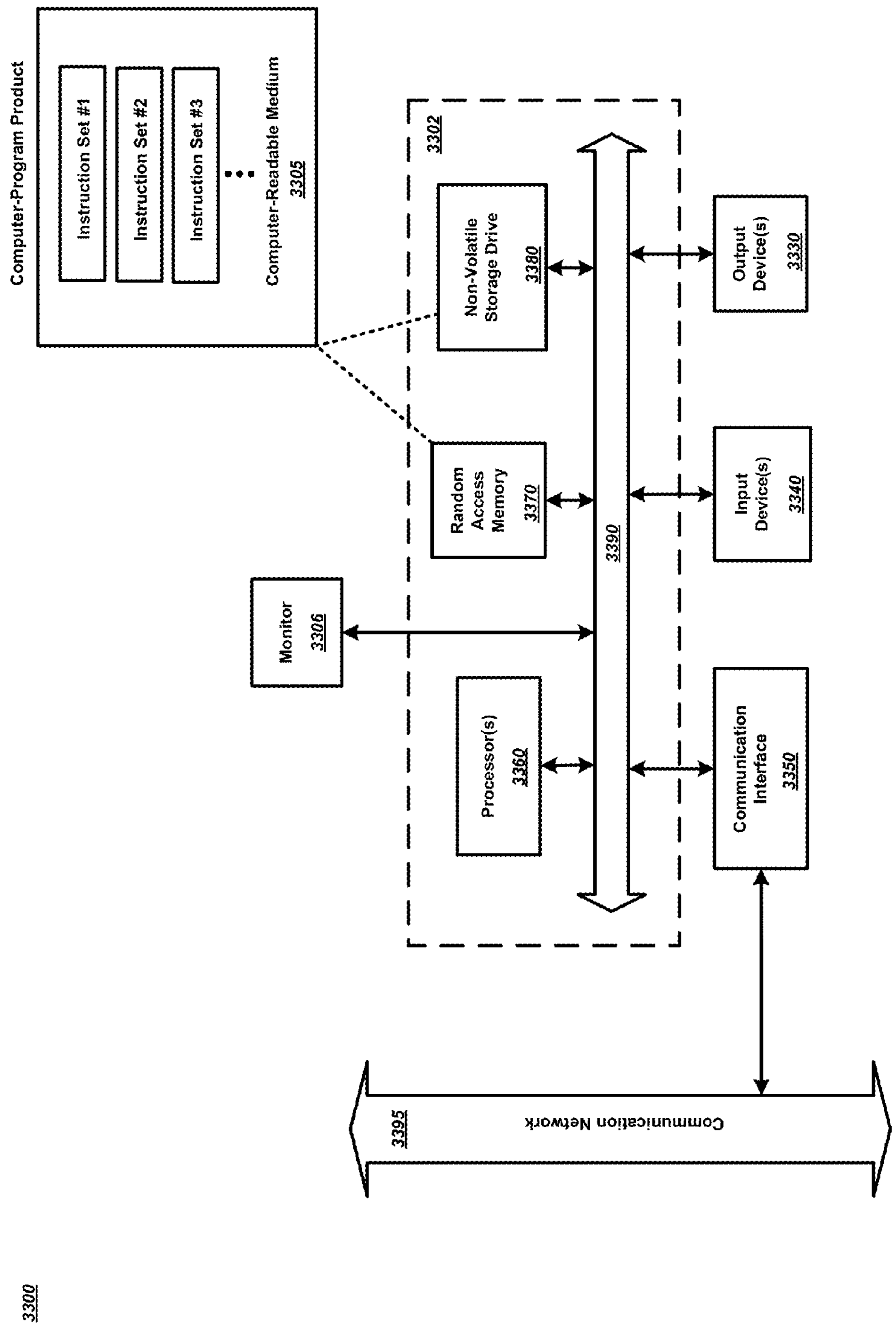
FIG. 33 shows an example computing system or device according to the disclosure.

Referring now to FIG. 33, an example of a special-purpose computer system 3300 is shown. For example, one or more intelligent components, the processing engine 308 and components thereof may be a special-purpose computer system 3300. The above methods may be implemented by computer-program products that direct a computer system to perform the actions of the above-described methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof. After loading the computer-program products on a general purpose computer system 3626, it is transformed into the special-purpose computer system 3300.

Special-purpose computer system 3300 comprises a computer 3302, a monitor 3306 coupled to computer 3302, one or more additional user output devices 3330 (optional) coupled to computer 3302, one or more user-input devices 3340 (e.g., keyboard, mouse, track ball, touch screen) coupled to computer 3302, an optional communications interface 3350 coupled to computer 3302, a computer-program product 3305 stored in a tangible computer-readable memory in computer 3302. Computer-program product 3305 directs the special-purpose computer system 3300 to perform the above-described methods. Computer 3302 may include one or more processors 3360 that communicate with a number of peripheral devices via a bus subsystem 3390. These peripheral devices may include user output device(s) 3330, user-input device(s) 3340, communications interface 3350, and a storage subsystem, such as random access memory (RAM) 3370 and non-volatile storage drive 3380 (e.g., disk drive, optical drive, solid state drive), which are forms of tangible computer-readable memory.

Computer-program product 3305 may be stored in non-volatile storage drive 3380 or another computer-readable medium accessible to computer 3302 and loaded into memory 3370. Each processor 3360 may comprise a microprocessor, such as a microprocessor from Intel® or Advanced Micro Devices, Inc.®, or the like. To support the computer-program product 3305, the computer 3302 runs an operating system that handles the communications of the computer-program product 3305 with the above-noted components, as well as the communications between the above-noted components in support of the computer-program product 3305. Exemplary operating systems include Windows® or the like from Microsoft Corporation, Solaris® from Sun Microsystems, LINUX, UNIX, and the like.

User-input devices 3340 include all possible types of devices and mechanisms to input information to computer 3302. These may include a keyboard, a keypad, a mouse, a scanner, a digital drawing pad, a touch screen incorporated into the display, audio input devices such as voice recognition systems, microphones, and other types of input devices. In various examples, user-input devices 3340 are typically embodied as a computer mouse, a trackball, a track pad, a joystick, wireless remote, a drawing tablet, a voice command system. User-input devices 3340 typically allow a user to select objects, icons, text and the like that appear on the monitor 3306 via a command such as a click of a button or the like. User output devices 3330 include all possible types of devices and mechanisms to output information from computer 3302. These may include a display (e.g., monitor 3306), printers, non-visual displays such as audio output devices, etc.

Communications interface 3350 provides an interface to other communication networks and devices and may serve as an interface to receive data from and transmit data to other systems, WANs and/or the Internet 3318. Examples of communications interface 3350 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 3350 may be coupled to a computer network, to a FireWire® bus, or the like. In other examples, communications interface 3350 may be physically integrated on the motherboard of computer 3302, and/or may be a software program, or the like.

RAM 3370 and non-volatile storage drive 3380 are examples of tangible computer-readable media configured to store data such as computer-program product examples of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 3370 and non-volatile storage drive 3380 may be configured to store the basic programming and data constructs that provide the functionality of various examples of the present invention, as described above.

Software instruction sets that provide the functionality of the present disclosure may be stored in RAM 3370 and non-volatile storage drive 3380. These instruction sets or code may be executed by the processor(s) 3360. RAM 3370 and non-volatile storage drive 3380 may also provide a repository to store data and data structures used in accordance with the present invention. RAM 3370 and non-volatile storage drive 3380 may include a number of memories including a main random access memory (RAM) to store instructions and data during program execution and a read-only memory (ROM) in which fixed instructions are stored. RAM 3370 and non-volatile storage drive 3380 may include a file storage subsystem providing persistent (non-volatile) storage of program and/or data files. RAM 3370 and non-volatile storage drive 3380 may also include removable storage systems, such as removable flash memory.

Bus subsystem 3390 provides a mechanism to allow the various components and subsystems of computer 3302 to communicate with each other as intended. Although bus subsystem 3390 is shown schematically as a single bus, alternative examples of the bus subsystem may utilize multiple busses or communication paths within the computer 3302.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium," equivalently "nontransitory storage medium," may represent one or more persistent memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

Various modifications may be made without departing from the spirit and scope of the invention. Indeed, various user interfaces for operating hazard detectors, HVACSs and other devices have been provided yet the designs are meant to be illustrative and not limiting as to the scope of the overall invention. While methods and systems have been described for receiving hazard detection and hazard detector status information, it is contemplated that these methods may be applied to receive and/or communicate other information. It is to be further appreciated that the term hazard detector, as used throughout, can include hazard detectors having direct wired connection with hazard response systems, and can further include hazard detectors that do not connect directly with the hazard response systems, but that provide alerts concerning detected potential hazard conditions.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those of skill with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations may be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the example aspects or features described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:

receiving, by a hazard detector, sensor or feature readings representative of at least one of position and orientation of the hazard detector as placed to a surface at a location within a structure;

determining, by the hazard detector, that the hazard detector is in at least one of an inadvisable position and an inadvisable orientation as placed to the surface at the location within the structure based on the readings; and generating, by the hazard detector, a signal representative of a user-perceptible cue to indicate that the hazard detector is in at least one of the inadvisable position and the inadvisable orientation as placed to the surface at the location within the structure.

2. The method of claim 1, further comprising:

outputting, by the hazard detector, at least one of an audio cue and a visual cue based on the signal representative of the user-perceptible cue to indicate that the hazard detector is in at least one of the inadvisable position and the inadvisable orientation as placed to the surface at the location within the structure.

3. The method of claim 1, further comprising:

transmitting, by the hazard detector, the signal representative of the user-perceptible cue to a mobile device for presentation of a message thereby to indicate that the hazard detector is in at least one of the inadvisable position and the inadvisable orientation as placed to the surface at the location within the structure.

4. The method of claim 1, further comprising:

determining that the hazard detector is within a prohibitive distance from one or more other surfaces at the location within the structure based on readings of a proximity sensor of the hazard detector.

5. The method of claim 4, wherein the proximity sensor is selected from an ultrasonic sensor and an LED (Light Emitting Diode) time-of-flight range finder.

6. The method of claim 1, further comprising:

determining that the hazard detector is in an unacceptable spatial orientation as placed to the surface at the location within the structure based on readings of an orientation sensor of the hazard detector.

7. The method of claim 1, further comprising:

determining that a wireless signal strength detected by the hazard detector is within an unacceptable range based on the readings.

8. The method of claim 1, further comprising:

determining that at least one of a carbon monoxide detection feature, a smoke detection feature, an ALS (Ambient Light Sensor) detection feature, and an ambient temperature detection feature of the hazard detector is operating within an unacceptable range based on the readings.

9. A hazard detector, comprising:

at least one sensor or feature;

at least one processor, operatively coupled to the at least one sensor or feature; and a memory operatively coupled with and readable by the at least one processor, and having stored therein processor-readable instructions that when executed by the at least one processor cause the at least one processor to:

receive readings from the at least one sensor or feature representative of at least one of position and orientation of the hazard detector as placed to a surface at a location within a structure;

determine based on the readings that the hazard detector is in at least one of an inadvisable position and an inadvisable orientation as placed to the surface at the location within the structure; and generate a signal representative of a user-perceptible cue to indicate that the hazard detector is in at least one of the inadvisable position and the inadvisable orientation as placed to the surface at the location within the structure.

10. The hazard detector of claim 9, further comprising at least one output device to output at least one of an audio cue and a visual cue based on the signal representative of the user-perceptible cue to indicate that the hazard detector is in at least one of the inadvisable position and the inadvisable orientation as placed to the surface at the location within the structure.

11. The hazard detector of claim 9, further comprising a wireless network interface to transmit the signal representative of the user-perceptible cue to a mobile device for presentation of a message thereby to indicate that the hazard detector is in at least one of the inadvisable position and the inadvisable orientation as placed to the surface at the location within the structure.

12. The hazard detector of claim 9, wherein the memory having stored therein processor-readable instructions that when executed by the at least one processor cause the at least one processor to:

determine that at least one of a carbon monoxide detection feature, a smoke detection feature, an ALS (Ambient Light Sensor) detection feature, and an ambient temperature detection feature of the hazard detector is operating within an unacceptable range based on the readings.

13. The hazard detector of claim 9, wherein the memory having stored therein processor-readable instructions that, when executed by the at least one processor, cause the at least one processor to:

determine that the hazard detector is within a prohibitive distance from one or more other surfaces at the location within the structure based on readings of a proximity sensor of the hazard detector;

determine that the hazard detector is in an unacceptable spatial orientation as placed to the surface at the location within the structure based on readings of an orientation sensor of the hazard detector; and determine that a wireless signal strength detected by the hazard detector is within an unacceptable range based on the readings.

14. A hazard detector, comprising:

means for receiving sensor or feature readings representative of at least one of position and orientation of the hazard detector as placed to a surface at a location within a structure;

means for determining that the hazard detector is in at least one of an inadvisable position and an inadvisable orientation as placed to the surface at the location within the structure based on the readings; and means for generating a signal representative of a user-perceptible cue to indicate that the hazard detector is in at least one of the inadvisable position and the inadvisable orientation as placed to the surface at the location within the structure.

15. The hazard detector of claim 14, further comprising:

means for outputting at least one of an audio cue and a visual cue based on the signal representative of the user-perceptible cue to indicate that the hazard detector is in at least one of the inadvisable position and the inadvisable orientation as placed to the surface at the location within the structure.

16. The hazard detector of claim 14, further comprising:

means for transmitting the signal representative of the user-perceptible cue to a mobile device for presentation of a message thereby to indicate that the hazard detector is in at least one of the inadvisable position and the inadvisable orientation as placed to the surface at the location within the structure.

17. The hazard detector of claim 14, further comprising:

means for determining that the hazard detector is within a prohibitive distance from one or more other surfaces at the location within the structure based on the readings.

18. The hazard detector of claim 14, further comprising:

means for determining that the hazard detector is in an unacceptable spatial orientation as placed to the surface at the location within the structure based on the readings.

19. The hazard detector of claim 14, further comprising:

means for determining that a wireless signal strength detected by the hazard detector is within an unacceptable range based on the readings.

20. The hazard detector of claim 14, further comprising:

means for determining that at least one of a carbon monoxide detection feature, a smoke detection feature, an ALS (Ambient Light Sensor) detection feature, and an ambient temperature detection feature of the hazard detector is operating within an unacceptable range based on the readings.

* * * * *